United States Patent
Pogue et al.

(10) Patent No.: US 10,232,041 B2
(45) Date of Patent: *Mar. 19, 2019

(54) COMBINATION OF LENALIDOMIDE AND POLYPEPTIDE CONSTRUCT, AND USES THEREOF

(71) Applicant: Teva Pharmaceuticals Australia Pty Ltd, Macquarie Park, NSW (AU)

(72) Inventors: Sarah L. Pogue, Frazer, PA (US); David S. Wilson, Frazer, PA (US); Anthony Gerard Doyle, Drummoyne (AU); Collette Jane Behrens, Macquarie Park (AU)

(73) Assignee: TEVA PHARMACEUTICALS PTY LTD, Macquarie Park (AU)

( * ) Notice: Subject to any disclaimer, the term of this patent is extended or adjusted under 35 U.S.C. 154(b) by 13 days.

This patent is subject to a terminal disclaimer.

(21) Appl. No.: 15/420,152

(22) Filed: Jan. 31, 2017

(65) Prior Publication Data

US 2017/0202962 A1    Jul. 20, 2017

Related U.S. Application Data

(63) Continuation of application No. 14/701,628, filed on May 1, 2015, now Pat. No. 9,636,334.

(60) Provisional application No. 61/986,913, filed on May 1, 2014.

(51) Int. Cl.
| | |
|---|---|
| *A61K 39/395* | (2006.01) |
| *A61K 38/21* | (2006.01) |
| *A61K 31/454* | (2006.01) |
| *C07K 16/28* | (2006.01) |
| *C07K 14/56* | (2006.01) |
| *A61K 45/06* | (2006.01) |
| *C07K 16/30* | (2006.01) |
| *A61K 47/68* | (2017.01) |
| *A61K 39/00* | (2006.01) |

(52) U.S. Cl.
CPC ...... *A61K 39/39558* (2013.01); *A61K 31/454* (2013.01); *A61K 38/212* (2013.01); *A61K 45/06* (2013.01); *A61K 47/6813* (2017.08); *A61K 47/6867* (2017.08); *C07K 14/56* (2013.01); *C07K 16/28* (2013.01); *C07K 16/2896* (2013.01); *C07K 16/3061* (2013.01); *A61K 2039/505* (2013.01); *C07K 2317/515* (2013.01); *C07K 2317/56* (2013.01); *C07K 2319/035* (2013.01); *C07K 2319/33* (2013.01)

(58) Field of Classification Search
CPC ............... A61K 31/454; A61K 38/212; A61K 39/39558; C07K 14/56; C07K 16/2896; C07K 16/28

See application file for complete search history.

(56) References Cited

U.S. PATENT DOCUMENTS

| | | |
|---|---|---|
| 4,908,431 A | 3/1990 | Colman et al. |
| 5,055,289 A | 10/1991 | Frincke et al. |
| 5,225,539 A | 7/1993 | Winter |
| 5,545,405 A | 8/1996 | Page |
| 5,558,864 A | 9/1996 | Bendig et al. |
| 5,565,332 A | 10/1996 | Hoogenboom et al. |
| 5,585,089 A | 12/1996 | Queen et al. |
| 5,650,150 A | 7/1997 | Gillies |
| 5,677,171 A | 10/1997 | Hudziak et al. |
| 5,693,761 A | 12/1997 | Queen et al. |
| 5,770,195 A | 6/1998 | Hudziak et al. |
| 5,772,997 A | 6/1998 | Hudziak et al. |
| 5,795,965 A | 8/1998 | Tsuchiya et al. |
| 5,837,821 A | 11/1998 | Wu |
| 5,840,299 A | 11/1998 | Bendig et al. |
| 5,844,093 A | 12/1998 | Kettleborough et al. |
| 5,976,531 A | 11/1999 | Mezes et al. |
| 5,977,322 A | 11/1999 | Marks et al. |
| 6,054,297 A | 4/2000 | Carter et al. |
| 6,180,370 B1 | 1/2001 | Queen et al. |
| 6,217,866 B1 | 4/2001 | Sela et al. |
| 6,248,516 B1 | 6/2001 | Winter et al. |
| 6,277,375 B1 | 8/2001 | Ward |
| 6,300,064 B1 | 10/2001 | Knappik et al. |
| 6,417,337 B1 | 7/2002 | Anderson et al. |
| 6,512,097 B1 | 1/2003 | Marks et al. |
| 6,569,430 B1 | 5/2003 | Waldmann et al. |
| 6,602,684 B1 | 8/2003 | Umana et al. |
| 6,800,735 B2 | 10/2004 | Whitty et al. |

(Continued)

FOREIGN PATENT DOCUMENTS

| | | |
|---|---|---|
| CN | 101045156 A | 10/2007 |
| EP | 0706799 A2 | 4/1996 |

(Continued)

OTHER PUBLICATIONS

Yoshinaga et al., J Biol Chem 143:593-601 (Year: 2008).*
Morabirto et al., "Peripheral blood CD38 expression predicts time to progression in B-cell chronic lymphocytic leukemia after first-line therapy with high-does chlorambucil", Haematologica, vol. 87, No. 2, Feb. 2002, pp. 217-218.
Igawa, et al., "Engineering the variable region of therapeutic IgG antibodies", MASS, Landes Bioscience, US, vol. 3, No. 3, May 1, 2011, p. 243-252.

(Continued)

*Primary Examiner* — Jessica H Roark
(74) *Attorney, Agent, or Firm* — Baker & Hostetler LLP

(57) ABSTRACT

Methods for cancer treatment include administering to a cancer patient an anti-CD38 antibody-attenuated human IFN alpha-2b construct and lenalidomide or pomalidomide. Tumors that may be treated according to these methods include tumors which comprise CD-38 expressing tumor cells, including B-cell lymphoma, multiple myeloma, non-Hodgkin's lymphoma, chronic myelogenous leukemia, chronic lymphocytic leukemia, and acute lymphocytic leukemia.

21 Claims, 9 Drawing Sheets

Specification includes a Sequence Listing.

(56) References Cited

U.S. PATENT DOCUMENTS

| | | |
|---|---|---|
| 6,821,505 B2 | 11/2004 | Ward |
| 6,872,392 B2 | 3/2005 | Nakamura et al. |
| 6,872,568 B1 | 3/2005 | Ni et al. |
| 6,903,203 B2 | 6/2005 | Copley et al. |
| 7,083,784 B2 | 8/2006 | Dall'Acqua et al. |
| 7,091,321 B2 | 8/2006 | Gillies et al. |
| 7,166,697 B1 | 1/2007 | Galanis et al. |
| 7,202,346 B2 | 4/2007 | Payne et al. |
| 7,217,797 B2 | 5/2007 | Hinton et al. |
| 7,252,994 B2 | 8/2007 | Chuntharapai et al. |
| 7,312,318 B2 | 12/2007 | Hansen et al. |
| 7,317,089 B2 | 1/2008 | Kikly |
| 7,326,681 B2 | 2/2008 | Gerngross |
| 7,355,015 B1 | 4/2008 | Dickson et al. |
| 7,371,819 B2 | 5/2008 | Escary |
| 7,388,081 B2 | 6/2008 | Seki et al. |
| 7,456,257 B2 | 11/2008 | Jones et al. |
| 7,521,047 B2 | 4/2009 | Nagy et al. |
| 7,566,771 B1 | 7/2009 | Adair et al. |
| 7,666,422 B2 | 2/2010 | Siegall et al. |
| 7,670,595 B2 | 3/2010 | Gillies et al. |
| 7,700,742 B2 | 4/2010 | Cohen et al. |
| 7,709,610 B2 | 5/2010 | Williams et al. |
| 7,723,485 B2 | 5/2010 | Junutula et al. |
| 7,732,572 B2 | 6/2010 | Cox, III |
| 7,732,578 B2 | 6/2010 | Foote |
| 7,776,330 B2 | 8/2010 | Yazaki et al. |
| 7,790,415 B2 | 9/2010 | Gillies et al. |
| 7,829,673 B2 | 11/2010 | De Weers et al. |
| 7,919,078 B2 | 4/2011 | Schreiber et al. |
| 7,943,744 B2 | 5/2011 | Frendeus et al. |
| 8,039,593 B2 | 10/2011 | Kuan et al. |
| 8,088,896 B2 | 1/2012 | Tesar et al. |
| 8,119,775 B2 | 2/2012 | Moretta et al. |
| 8,124,738 B2 | 2/2012 | Terret et al. |
| 8,153,765 B2 | 4/2012 | Park et al. |
| 8,187,601 B2 | 5/2012 | Weng et al. |
| 8,980,267 B2 | 3/2015 | Grewal et al. |
| 9,139,634 B2 | 9/2015 | Morrison et al. |
| 9,636,334 B2 * | 5/2017 | Pogue ................ A61K 31/454 |
| 2002/0142358 A1 | 10/2002 | Mikayama et al. |
| 2002/0164788 A1 | 11/2002 | Ellis et al. |
| 2002/0193569 A1 | 12/2002 | Hanna |
| 2003/0211100 A1 | 11/2003 | Bedian et al. |
| 2003/0211553 A1 | 11/2003 | Logtenberg et al. |
| 2004/0006215 A1 | 1/2004 | Keler et al. |
| 2004/0071696 A1 | 4/2004 | Adams et al. |
| 2006/0083736 A1 | 4/2006 | Law et al. |
| 2006/0269516 A1 | 11/2006 | Presta et al. |
| 2007/0098718 A1 | 5/2007 | Long et al. |
| 2008/0166352 A1 | 7/2008 | Siu et al. |
| 2009/0068175 A1 | 3/2009 | Lazar et al. |
| 2009/0076249 A1 | 3/2009 | De Weers et al. |
| 2009/0092599 A1 | 4/2009 | Lazar et al. |
| 2009/0123950 A1 | 5/2009 | Tesar |
| 2009/0142340 A1 | 6/2009 | Lazar et al. |
| 2009/0175863 A1 | 7/2009 | Kraus et al. |
| 2009/0202568 A1 | 8/2009 | Eriksson et al. |
| 2009/0304710 A1 | 12/2009 | Park et al. |
| 2010/0104557 A1 | 4/2010 | Bernett et al. |
| 2010/0172868 A1 | 7/2010 | Morrison et al. |
| 2010/0189689 A1 | 7/2010 | Chang et al. |
| 2010/0189729 A1 | 7/2010 | Hoerr et al. |
| 2010/0285004 A1 | 11/2010 | Tesar et al. |
| 2011/0104112 A1 | 5/2011 | Morrison et al. |
| 2012/0201827 A1 | 8/2012 | Elias |
| 2013/0302318 A1 | 11/2013 | Rojkjaer |
| 2014/0248238 A1 | 9/2014 | Wilson, Jr. |
| 2015/0203560 A1 | 7/2015 | Grewal et al. |
| 2015/0313965 A1 | 11/2015 | Pogue et al. |
| 2016/0068612 A1 | 3/2016 | Clarke |
| 2016/0122410 A1 | 5/2016 | Behrens |

FOREIGN PATENT DOCUMENTS

| | | |
|---|---|---|
| WO | 90/05144 A1 | 5/1990 |
| WO | 97/00271 A1 | 1/1997 |
| WO | 97/24137 A1 | 7/1997 |
| WO | 00/40265 A1 | 7/2000 |
| WO | 0042072 | 7/2000 |
| WO | 0197844 | 12/2001 |
| WO | 2005103083 | 11/2005 |
| WO | 2006099875 | 9/2006 |
| WO | 2006125640 | 11/2006 |
| WO | 2007042309 | 4/2007 |
| WO | 2008006554 | 1/2008 |
| WO | 2008037257 | 4/2008 |
| WO | 2008047242 | 4/2008 |
| WO | 2008124086 | 10/2008 |
| WO | 2008/145139 A1 | 12/2008 |
| WO | 2009017823 | 2/2009 |
| WO | 2010/105290 A1 | 9/2010 |
| WO | 2011154453 | 12/2011 |
| WO | 2012/041800 A1 | 4/2012 |
| WO | 2012/083370 A1 | 6/2012 |
| WO | 2012092612 | 7/2012 |
| WO | 2013059885 | 5/2013 |
| WO | 2013/107791 A1 | 7/2013 |
| WO | 2014/028502 A1 | 2/2014 |
| WO | 2014178820 | 11/2014 |

OTHER PUBLICATIONS

Lesinski, et al., "IFN-a Bortezomib Overcome Bcl-2 and Mcl-1 Overexpression in Melanoma Cells by Stimulating the Extrinsic Pathway of Apoptosis", Cancer Res., 68(20), pp. 8351-8360, 2008.

Laubach, et al., "Daratumumab granted breakthrough drug status", Expert Opinion on Investigational Drugs, vol. 23, No. 4, Feb. 2014, pp. 445-452.

Ku, et al., "Alternate Protein Frameworks for Molecular Recognition", Proc. Natl. Acad. Sci. USA, vol. 92, pp. 6552-6556, Jul. 1995.

Kossman, et al., "A Phase I Trial of Humanized Monoclonal Antibody HuM195 (anti-DC33) with Low-Dose Interleukin 2 in Acute Myelogenous Leukemia", Clin. Can. Res., vol. 5, Oct. 1999, pp. 2748-2755.

Koltchev, et al., "Synergy of Interferons and Bortezomib: Advantages of Combination Treatments in Facilitating Apoptosis in Muliple Myeloma Cells", PBL Interferon Source, 2010.

Kodama, et al., "Mutated SEA-D227 A-conjgated antibodies greatly enhance antitumor activity against MUC1-expressing bile duct carcinoma", Cancer Immunology, Immnotherapy, vol. 50, No. 10, Dec. 2001, pp. 539-548.

Jorge Cortes et al: "Immune modulation of minimal residual disease in early chronic phase chronic myelogenous leukemia : A randomized trial of frontline high-dose imatinib mesylate with or without pegylated interferon alpha-2b and granulocyte-macrophage colony-stimulatin", 1-15, Cancer., vol. 117, No. 3, Sep. 30, 2010, pp. 572-580.

J. P. Laubach et al: "CD38-Targeted Immunochemotherapy in Refractory Multiple Myeloma: A New Horizon", Clinical Cancer Research, vol. 21, No. 12, Apr. 15, 2015, pp. 2660-2662.

Israeli, et al., "Molecular Cloning of a Complementary DNA Encoding a Prostate-specific Membrane Antigen", Can. Res., vol. 53, Jan. 15, 1993, pp. 227-230.

International Search Report dated Nov. 23, 2015, in PCT/IB2015/001600.

International Search Report and Written Opinion issued in related application PCT/AU2015/050654 dated Dec. 3, 2015.

Ibrahim, et al., "CD38 Expression as an Important Prognostic Factor in B-Cell Chronic Lymphocytic Leukemia", Blood, vol. 98, No. 1, Jul. 2001, pp. 181-186.

Hoon, et al., "Molecular Cloning of a Human Monoclonal Antibody Reactive to Ganglioside Gm3 Antigen on Human Cancers", Can. Res. vol. 53, Nov. 1, 1993, pp. 5244-5250.

Honegger, et al., "Yet another numbering Scheme for Immunoglobulin Variable Domains: An Automatic Modeling and Analysis Tool", J. Mol. Biology, 309, pp. 657-670, 2001.

(56) References Cited

OTHER PUBLICATIONS

Hellstroem, et al., "Monoclonal Mouse Antibodies Raised Against Human Lung Carcinoma", Can. Res., vol. 46, Aug. 1986, pp. 3917-3923.
Hamers-Casterman, et al., "Naturally occurring antibodies devoid of light chains", Nature, vol. 363, Jun. 3, 1993, pp. 446-448.
H. Ludwig et al: "Thaiidomide-dexamethasone compared with melphalan-prednisolone in elderly patients with multiple myeloma", Blood, vol. 113, No. 15, Oct. 27, 2008, pp. 3435-3442.
Giudicelli, et al., "IMGT, The International Immunogene Tics database", Nucleic Acids Research, vol. 25, No. 1, pp. 206-211, 1997.
Ghetie, et al., Anti-CD19 Inhibits the Growth of Human B-Cell Tumor Lines in Vitro and of Daudi Cells in SCIO Mice by Inducing Cell Cycle Arrest, Blood, vol. 83, No. 5, Mar. 1994, pp. 1329-1336.
Ghasriani et al., JBC, vol. 288, Jan. 4, 2013, No. 1, pp. 247-254.
Frey et al., Antibody-based Targeting of Interferon-Alpha to the Tumor Neovasculature: a Critical Evaluation; Royal Society of Chemistry, Integr. Biol., vol. 3, pp. 468-478, 2011.
Frederic Millot et al: "Results of a phase II trial testing interferon-alpha 2b and cytarabine in children and adolescents with chronic myelogenous leukemia", Pediatric Blood and Cancer, vol. 47, No. 5, 1 Jan. 2006, pp. 555-559.
Francisco, et al., "Agonistic Properties and in Vivo Antitumor Activity of the Anti-CD40 Antibody SGN-14", Can. Res., vol. 60, Jun. 15, 2000, pp. 3225-3231.
Edleman, et al., "The Covalent Stucture of an Entire yG Immunoglobulin Molecule", Biochemisty, vol. 63, pp. 78-85, Mar. 1969.
de Weers, et al., "Daratumumab, a Novel Therapeutic Human CD38 Monoclonal Antibody, Induces Killing of Multiple Myeloma and other Hematological Tumors", J. Immunol., 2011, 186:1840-1848.
Chothia, et al., "Conformations of Immunoglobulin Hypervariable Regions", Nature, vol. 342 pp. 877-883, Dec. 1989.
Chothia et al., "Canonical Structures for the Hypervariable Regions of Immunoglobulins" J. Mol. Biol., No. 196, pp. 901-917, 1987.
Bork, et al., "Go hunting in sequence databases but watch out for traps", Trends in Genetics, Oct. 1996, vol. 12, No. 10, pp. 425-427.
Bork, "Powers and Pitfalls in Sequence Analysis: The 70% Hurdle", Genome Research, 2000, 10:398-400.
Bonardi, et al., "Delivery of Saporin to Human B-Cell Lymphoma Using Bispecffic Antibody: Targeting via DC22 byt not CD19, CD37, or Immunoglobulin Results in Efficient Killing", Can. Res., vol. 53, Jul. 1991, pp. 3015-3021.
Ausiello, et al., "Functional topography of discrete domains of human CD38", Tissue Antigens, 2000, 56:539-547.
A. Aviles et al: "Randomized clinical trial of zoledronic acid in multiple myeloma patients undergoing high-dose chemotherapy and stem-cell transplantation", Current Oncology, vol. 20, No. 1, Feb. 1, 2013, the whole document.
Chothia, et al., "Canonical Structures for the Hypervariable Regions of Immunoglobulins", J. Mol. Biol., (1987), No. 196, pp. 901-917.
Chothia, et al., "Conformations of immunoglobulin hypervariable regions", Nature, vol. 342, Dec. 1989, pp. 877-883.
Edelman, et al., "The Covalent Structure of an Entire yG Immunoglobulin Molecule", Biochemistry, vol. 63, 1969, pp. 78-85.
Giudicelli, et al., "IMGT, the international ImMunoGeneTics database", Nucleic Acids Research, 1997, vol. 25, No. 1, pp. 206-211.
Honegger, et al., "Yet another numbering scheme for immunoglobulin variable domains: An automatic modeling and analysis tool", J. Mol. Biol., (2001) 309, 657-670.
International Search Report and Written Opinion from related application PCT/AU2012/001323 dated Mar. 13, 2013.
International Search Report and Written Opinion from related application PCT/US2013/038659 dated Feb. 12, 2014.
International Search Report and Written Opinion issued in related application PCT/IB2015/001600 dated Nov. 23, 2015.
Koltchev, et al., "Synergy of Interferons and Bortezomib: Advantages of Combination Treatments in Facilitating Apoptosis in Multiple Myeloma Cells", 2010, PBL InterferonSource.
Ku, et al., "Alternate protein frameworks for molecular recognition", Proc. Natl. Acad. Sci. USA, vol. 92, Jul. 1995, pp. 6552-6556.
Laubach, et al., "Daratumumab granted breakthrough drug status", Expert Opin. Investig. Drugs, 2014, 23 (4):445-452.
Lesinski, et al., "IFN-a Bortezomib Overcome Bcl-2 and Mcl-1 Overexpression in Melanoma Cells by Stimulating the Extrinsic Pathway of Apoptosis", Cancer Res., Oct. 2008; 68:(20), pp. 8351-8360.
Padlan, et al., "Identification of specificity-determining residues in antibodies", FASEB Journal, vol. 9, Jan. 1995, pp. 133-139.
Piehler, et al., "New structural and functional aspects of the Type 1 interferon-receptor interaction revealed by comprehensive mutational analysis of the binding interface", vol. 275, No. 51, Dec. 2000, pp. 40425-40433.
Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", J. Biological Chemistry, vol. 278, No. 5, Jan. 2003, pp. 3466-3473.
Igawa et al. "Engineering the variable region of therapeutic IgG antibodies", MABS, Landes Bioscience, US, vol. 3, No. 3, May 1, 2011, p. 243-252.
Richardson, et al., Br. J. Haematol., 2011; 154:745-54.
De Weers, et al., J. Immunol. 2011; 186:1840-48.
Tse, et al., Clin. Cancer Res., 2006; 12(4):1373-82.
Ausiello, et al., Tissue Antigens, 2000; 56:539-47.
Pollack, et al., Cancer Chemother. Pharmacol. 2007; 60:423-35.
Yu, et al., "Coexpression of Different Antigenic Markers on Moieties that Bear CA 125 Determinants", Can. Res., vol. 51, Jan. 15, 1991, pp. 468-475.
Yokota, et al., "Rapid Tumor Penetration of a Signle-Chain Fv and Comparison with other Immunoglobulin Forms", Can. Res., vol. 52, Jun. 15, 1992, pp. 3402-3408.
Wells, 1990, Biochemistry 29:8509-8517.
Wahl, et al., "The Anti-CD30 Monoclonal Antibody SGN-30 Promotes Growth Arrest and DNA Fragmentation in Vitro and Afects Antibumor Activity in Models of Hodgkin's Disease", Can. Res., vol. 62, Jul. 1, 2002, pp. 3736-3742.
Vijayasaradhi, et al., "The Melanoma Antigen gp75 is the Human Homologue of the Mouse b (Brown) Locus Gene Product", J. Exp. Med., vol. 171, Apr. 1990, pp. 1375-1380.
van Hof, et al., "Biodistribution of Indium-Labeled Engineered Human Antibody CTMO1 in Ovarian Cancer Patients: Influence of Protein Dose", Can. Res., vol. 56, Nov. 15, 1996, pp. 5179-5185.
Van Der Veer Michael S et al: "Towards effective immunotherapy of myeloma: enhanced elimination of myeloma cells by combination of lenalidomide with the human CD38 monoclonal antibody daratumumab", Haematolo, Ferrata Storti Foundation, Italy, vol. 96, No. 2, Feb. 1, 2011 (Feb. 1, 2011), pp. 284-290.
Tse, et al., "CR011, a Fully Human Monoclonal Antibody-Auristatin E Conjugate, for the Treatment of Melanoma", Clin. Cancer Res., 2006; 12(4):1373-1382.
Trail, et al., "Effect of Linker Variation on the Stability, Porency, and Efficacy of Carcinoma-reactive BR64-Doxorubicin Immunoconjugates", Can. Res., vol. 57, Jan. 1, 1997, pp. 100-105.
Thalidomide-dexamethasone compared with melphalan-prednisolone in elderly patients with multiple myeloma, Heinz Ludwig, 1 Roman Hajek,2 Elena Tóthova,3 Johannes Drach,4 Zdenek Adam,2 Boris Labar,5 Miklos Egyed,6, 3435-3442, 113/15, Blood 113:3435-42 (2009).
Tailor, et al., "Nucleotide sequence of human prostatic acid phosphatase determined from a full-length cDNA clone", Nucleic Acids Research, vol. 18, No. 16, Jul. 11, 1990, p. 4928.
Sievers, et al., "Selective Ablation of Acute Myeloid Leukemia Using Antibody-Targeted Chemotherapy: a Phase I Study of Anti-CD33 Calichaemicin Immunoconjugate", Blood, vol. 93, No. 11, Jun. 1, 1999, pp. 3678-3784.
Sgouros, et al., "Modeling and Dosimetry of Monoclonal Antibody M195 (Anti-CD33) in Acute Myelogenous Leukemia", J. Nucl. Med., vol. 34, No. 3, Mar. 1993, pp. 422-430.
Rossi et al., "Preclinical Studies on Targeted Delivery of Multiple IFNa2b to HLA-DR in Diverse Hemotologic Cancers" Lymphoid Neoplasia, Blood Journal, vol. 118, No. 7, Aug. 18, 2011.

(56) References Cited

OTHER PUBLICATIONS

Rosenblum, et al., "Recombinant Immunotoxins Directed against c-erb-3/HER2/neu Oncogene Product: In Vitro Cytotoxicity, Pharmacokinetics, and in Vivo Efficacy Studies in Xenograft Models", Clin. Can. Res., vol. 5, Apr. 1999, pp. 865-874.

Richardson, et al., "Monoclonal Antibodies in the Treatment of Multiple Myeloma", British Journal of Haematology, 2011, 154:745-754.

Reff, et al., "Depletion of B Cells In Vivo by a Chimeric Mouse Human Monoclonal Antibody to CD20", Blood, vol. 83, No. 2, Jan. 15, 1994, pp. 435-445.

Pollack et al., Treatment parameters Modulating Regression of Human Melanoma Xenografts by an Antibody-drug conjugate (CR011-vcMMAE) targeting GPNMB, Cancer Chemother Pharmacol, 60, pp. 423-435, 2007.

Peterson, et al., "Effect of Multiple, Repeated Doses of Radioimmunotherapy on Target Antigen Expression (Breast MUC-1 Mucin) in Breast Carcinomas", Can. Res., vol. 57, Mar. 15, 1997, pp. 1103-1108.

Pavlinkova, et al., "Radioimmunotherapy of Human Colon Cancer Xenografts Using a Dimeric Single-Chain Fv Antibody Construct", vol. 5, Sep. 1999, pp. 2613-2619.

Padlan, et al., "Identification of Specificity-Determining Residues in Antibodies" FASEB Journal, vol. 9, pp. 133-139, Jan. 1999.

Ngo, et al., "Computational Complexity, Proteub Structure Prediction, and the Levinthal Paradox", The Protein Folding Problem and Tertiary Structure Prediction, 1994, pp. 492-495.

Mittelman, et al., "Active Specific Immunotherapy in Patients with Melanoma", J. Clin. Invest., vol. 86, Dec. 1990, pp. 2136-2144.

Mason, et al., "Value of Monoclonal Anti-CD22 (p135) Antibodies for the Detection of Normal and Neoplastic B Lymphoid Cells", Blood, vol. 69, No. 3, Mar. 1987, pp. 836-840.

Maier, et al., "Requirements for the Internalization of a Murine Monoclonal Antibody Directed against the HER-2/neu Gene Product c-erB-2", Can. Res., vol. 51, Oct. 1, 2991, pp. 5361-5369.

* cited by examiner

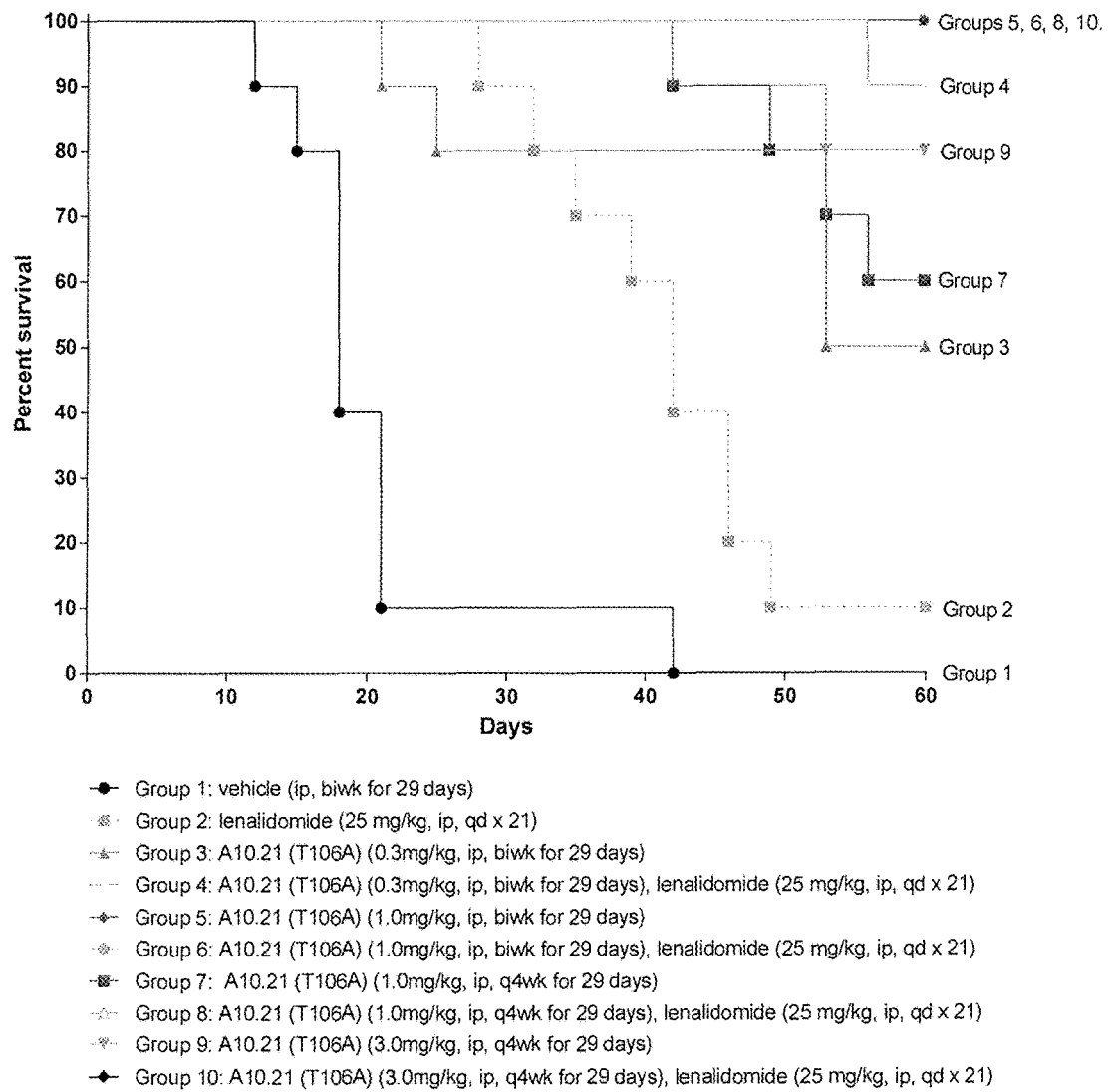

- Group 1: vehicle (ip, biwk for 29 days)
- Group 2: lenalidomide (25 mg/kg, ip, qd x 21)
- Group 3: A10.21 (T106A) (0.3mg/kg, ip, biwk for 29 days)
- Group 4: A10.21 (T106A) (0.3mg/kg, ip, biwk for 29 days), lenalidomide (25 mg/kg, ip, qd x 21)
- Group 5: A10.21 (T106A) (1.0mg/kg, ip, biwk for 29 days)
- Group 6: A10.21 (T106A) (1.0mg/kg, ip, biwk for 29 days), lenalidomide (25 mg/kg, ip, qd x 21)
- Group 7: A10.21 (T106A) (1.0mg/kg, ip, q4wk for 29 days)
- Group 8: A10.21 (T106A) (1.0mg/kg, ip, q4wk for 29 days), lenalidomide (25 mg/kg, ip, qd x 21)
- Group 9: A10.21 (T106A) (3.0mg/kg, ip, q4wk for 29 days)
- Group 10: A10.21 (T106A) (3.0mg/kg, ip, q4wk for 29 days), lenalidomide (25 mg/kg, ip, qd x 21)

Fig. 4

COMBINATION OF LENALIDOMIDE AND POLYPEPTIDE CONSTRUCT, AND USES THEREOF

CROSS REFERENCE TO RELATED APPLICATIONS

This application is a continuation of U.S. patent application Ser. No. 14/701,628 filed on May 1, 2015, which claims priority to U.S. Provisional Application No. 61/986,913 filed on May 1, 2014, each of which are incorporated by reference herein in their entirety and for all purposes.

REFERENCE TO A SEQUENCE LISTING

This application includes a Sequence Listing submitted electronically as a text file SEQ_LST_Lenalidomide_ST25.TXT, created on May 1, 2015 with a size of 284,000 bytes. The Sequence Listing is incorporated by reference herein.

FIELD

This disclosure relates generally to the field of cancer treatment. More specifically, this disclosure relates to a cancer therapy that synergistically combines lenalidomide or pomalidomide with an anti-CD38 antibody-attenuated interferon alpha-2b construct. The combination therapy substantially enhances tumor growth inhibition or delay relative to the tumor growth inhibition or delay exhibited by administration of either lenalidomide, pomalidomide, or the construct alone. In addition, the combination therapy may overcome lenalidomide resistance or pomalidomide resistance.

BACKGROUND

Various publications, including patents, published patent applications, technical articles, scholarly articles, and gene or protein accession numbers are cited throughout the specification. Each of these materials is incorporated by reference herein, in its entirety and for all purposes.

CD38 is a 46 kDa type II transmembrane glycoprotein that is involved in transmembrane signaling and cell adhesion. It is also known as cyclic ADP ribose hydrolase because it can transform $NAD^+$ and $NADP^+$ into cADPR, ADPR and NAADP, depending on extracellular pH. These products induce $Ca^{2+}$-mobilization inside the cell, which can lead to tyrosine phosphorylation and activation of the cell. CD38 is also a receptor that can interact with a ligand, CD31. Activation of receptor via CD31 leads to intracellular events including $Ca^{2+}$ mobilization, cell activation, proliferation, differentiation and migration.

CD38 is expressed at high levels on the surface of multiple myeloma cells, in most cases of T- and B-lineage acute lymphoblastic leukemias (ALL), some acute myelocytic leukemias, follicular center cell lymphomas and T lymphoblastic lymphomas. CD38 is also expressed on B-lineage chronic lymphoblastic leukemia (B-CLL) cells. In some cases, B-CLL patients presenting with a CD38+ clone are characterized by an unfavorable clinical course with a more advanced stage of disease, poor responsiveness to chemotherapy and shorter survival time.

Interferons, and in particular IFN-alpha, are able to increase apoptosis and decrease proliferation of certain cancer cells. IFN-alpha has been approved by the FDA for the treatment of several cancers including melanoma, renal cell carcinoma, B cell lymphoma, multiple myeloma, chronic myelogenous leukemia (CML) and hairy cell leukemia. A direct effect of IFN-alpha on the tumor cells is mediated by the IFN-alpha binding directly to the type I IFN receptor on those cells and stimulating apoptosis, terminal differentiation and/or reduced proliferation. Further, amongst the indirect effects of IFN-alpha on non-cancer cells is the ability of IFN-alpha to stimulate the immune system, which may produce an additional anti-cancer effect by causing the immune system to reject the tumor. IFN-alpha also exhibits the ability to inhibit tumor angiogenesis and, thus, may inhibit tumor growth by metabolic starvation.

The direct anti-tumor activities of IFN-alpha are mediated by type I interferon receptors on the surface of the cancer cells which, when stimulated, initiate various signal transduction pathways leading to reduced proliferation and/or the induction of terminal differentiation or apoptosis. The type I interferon receptor is, however, also present on most non-cancerous cells. Activation of the type I receptor on non-cancerous cells by IFN-alpha causes the expression of numerous pro-inflammatory cytokines and chemokines, leading to undesirable systemic toxicity. Such toxicity may cause severe flu-like symptoms, which prevents the dosing to a subject of IFN-alpha at levels that exert the maximum anti-proliferative and pro-apoptotic activity on the cancer cells.

In general, IFN may be targeted to cancer cells, for example, by linking it with a targeting antibody or targeting fragment thereof. While this approach may result in an increase in activity of the IFN against cancer cells, it does not completely address the issue of undesired activity of the IFN on healthy cells. Fusing IFN-alpha to the C-terminus of the heavy chain of an IgG may, for example, prolong the half-life of the IFN alpha, which may prolong undesirable adverse events. Accordingly, there exists a need to improve the systemic toxicity profile of interferon while retaining one or more of its anti-tumor effects.

Both lenalidomide and pomalidomide are small molecule immune modulators, and derivatives of the anti-multiple myeloma drug thalidomide. Both lenalidomide and pomalidomide are used in the treatment and maintenance of certain cancers, including multiple myeloma and lymphoma. In many cases, tumors which are initially sensitive to lenalidomide or pomalidomide become resistant or refractory to these agents. In other cases, tumors do not respond to lenalidomide or pomalidomide therapy. There is a need in the art to overcome lenalidomide or pomalidomide-resistance or to enhance lenalidomide or pomalidomide activity, and potentially provide therapies whereby non-responsive patients may come to respond to lenalidomide or pomalidomide therapy.

SUMMARY

The disclosure features methods for treating tumors. The methods may comprise administering to a subject having a tumor an anti-CD38 antibody-attenuated IFN alpha-2b construct in an amount effective for treating the tumor and lenalidomide in an amount effective for treating the tumor. The methods may comprise administering to a subject having a tumor an anti-CD38 antibody-attenuated IFN alpha-2b construct in an amount effective for treating the tumor and pomalidomide in an amount effective for treating the tumor. The construct may enhance the anti-tumor activity of the lenalidomide or may enhance the anti-tumor activity of the pomalidomide, and/or the lenalidomide or pomalidomide may enhance the anti-tumor activity of the construct. The effective amount preferably is an amount at which both agents synergize to substantially inhibit and/or delay tumor growth when compared to tumor growth following the administration of only lenalidomide or pomalidomide or construct. The administration eliminate established tumors, and/or inhibit tumor re-establishment. The subject may be any mammal, preferably is a primate, and most preferably is a human being. Preferably, the amount of the construct and the amount of lenalidomide or pomalidomide are sufficient for the construct and the lenalidomide or pomalidomide to synergize in their therapeutic effect. Each of the construct and the lenalidomide or pomalidomide may be comprised in a composition which comprises a pharmaceutically acceptable carrier, although the construct and lenalidomide or pomalidomide may be comprised in separate compositions. The construct and the lenalidomide or pomalidomide may be administered substantially at the same time, or may be administered sequentially. Administration may be intravenously (e.g., construct), or orally (e.g., lenalidomide or pomalidomide) and may be at the direction of a medical practitioner. It is believed that the construct remains in circulation longer than lenalidomide or pomalidomide does, such that a therapeutic regimen may comprise more frequent administration of lenalidomide or pomalidomide relative to the administration of the construct. In accordance with such methods, the construct may comprise any anti-CD38 antibody and any attenuated interferon alpha-2b molecule described or exemplified herein.

The tumor will comprise CD-38-expressing tumor cells. The tumor may comprise a B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia or acute lymphocytic leukemia. Any such tumor may be sensitive to lenalidomide or pomalidomide alone or resistant to lenalidomide or pomalidomide alone, such that the combination therapy produces a therapeutic benefit to the subject. Multiple myeloma is highly preferred. The disclosure also features use of an anti-CD38 antibody-attenuated IFN alpha-2b construct and lenalidomide or pomalidomide as a combination therapy in the treatment of B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia, or acute lymphocytic leukemia.

The anti-CD38 antibody-attenuated IFN alpha-2b construct is preferably a fusion protein comprising an anti-CD38 antibody portion comprising a heavy chain and a light chain, and an attenuated IFN alpha-2b portion, preferably with the C-terminus of the anti-CD38 antibody heavy chain fused to the N-terminus of the attenuated IFN alpha-2b directly by a peptide bond. In some aspects, the C-terminus of the anti-CD38 antibody heavy chain is fused to the N-terminus of the attenuated IFN alpha-2b via a linker peptide of five or more amino acids and, accordingly, the construct further comprises a linking peptide.

The anti-CD38 antibody portion of the construct may comprise a heavy chain variable region comprising the amino acid sequence of SEQ ID NO: 17 and a light chain variable region comprising the amino acid sequence of SEQ ID NO: 21, optionally with the proviso that SEQ ID NO: 17 excludes the amino acid sequence of SEQ ID NO: 24 and SEQ ID NO: 21 excludes the amino acid sequence of SEQ ID NO: 25. The heavy chain variable region and light chain variable region pairs may be chosen from the pairs set forth in any of Tables 1-4 of this disclosure.

In some aspects, the anti-CD38 antibody portion of the construct comprises a heavy chain variable region comprising the amino acid sequence of SEQ ID NO: 18 and a light chain variable region comprising the amino acid sequence of SEQ ID NO: 22. The anti-CD38 antibody may comprise a heavy chain variable region comprising the amino acid sequence of SEQ ID NO: 19 and a light chain variable region comprising the amino acid sequence of SEQ ID NO: 21, optionally with the proviso that SEQ ID NO: 21 excludes the amino acid sequence of SEQ ID NO: 25. In some aspects, the anti-CD38 antibody portion of the construct comprises a heavy chain variable region comprising the amino acid sequence of SEQ ID NO: 20 and a light chain variable region comprising the amino acid sequence of SEQ ID NO: 23.

The anti-CD38 antibody portion of the construct may comprise a heavy chain variable region comprising the amino acid sequence of SEQ ID NO: 26, SEQ ID NO: 27, or SEQ ID NO: 28. The anti-CD38 antibody portion of the construct may comprise a light chain variable region comprising the amino acid sequence of SEQ ID NO: 29 or SEQ ID NO: 30. Any of SEQ ID NOs: 26, 27, or 28 may be paired with any of SEQ ID NOs: 29 or 30. In highly preferred aspects, the anti-CD38 antibody portion of the construct may comprise a heavy chain variable region comprising the amino acid sequence of SEQ ID NO: 27 and a light chain variable region comprising the amino acid sequence of SEQ ID NO: 29.

In some aspects, the anti-CD38 antibody-attenuated interferon alpha-2b construct comprises an anti CD-38 antibody heavy chain-attenuated aglycosylated interferon alpha-2b fusion polypeptide comprising the amino acid sequence of SEQ ID NO: 216, and an anti-CD38 antibody light chain which comprises a variable region comprising the amino acid sequence of SEQ ID NO: 29. In some aspects, the light chain has the amino acid sequence of SEQ ID NO: 217 (variable and constant regions).

The anti-CD38 antibody portion of the construct may comprise a human IgG1 constant region. In some preferred aspects, the anti-CD38 antibody portion of the construct may comprise a human IgG4 constant region. It is preferred that the antibody comprise an IgG4 constant region or an IgG1 constant region engineered to abolish FcR binding to avoid antibody-mediated effector functions, which is believed to provide an advantage in avoiding non-specific Fc receptor-mediated antibody binding and subsequent IFN-mediated toxicity on non-antibody-targeted cells.

The human IgG1 constant region may optionally comprise a tyrosine at position 252, a threonine at position 254, and a glutamic acid at position 256 according to the EU numbering system. The human IgG4 constant region may optionally comprise a proline at position 228 according to the EU numbering system, and optionally further comprises a tyrosine at position 252, a threonine at position 254, and a glutamic acid at position 256 according to the EU numbering system. The anti-CD38 antibody portion of the construct may comprise a Fab.

The attenuated interferon alpha-2b portion of the construct may be an attenuated human interferon alpha-2b. The attenuated interferon alpha-2b portion of the construct may comprise the amino acid sequence of any one of SEQ ID NO: 3, SEQ ID NO: 5, SEQ ID NO: 6, SEQ ID NO: 7, SEQ ID NO: 8, SEQ ID NO: 211, SEQ ID NO: 212, SEQ ID NO: 213, SEQ ID NO: 214, or SEQ ID NO: 215. The attenuated interferon alpha-2b portion of the construct may include a 23 amino acid N-terminal truncation (SEQ ID NO: 4). The attenuated interferon alpha-2b portion of the construct preferably includes a 23 amino acid N-terminal truncation with an A145D substitution (SEQ ID NO: 5) or A145G substitution (SEQ ID NO: 7). The attenuated interferon alpha-2b portion of the construct may be aglycosylated, for example, a truncated (23 amino acid N-terminal truncation) human interferon alpha-2b with an amino acid deletion or substitution at position 106, which preferably is a T106A substitution, but may comprise other suitable substitutions to remove the glycosylation site (SEQ ID NO: 214). In some preferred aspects, the attenuated interferon alpha-2b portion of the construct includes the T106A substitution and the A145D substitution (SEQ ID NO: 212) or the A145G substitution (SEQ ID NO: 213). In some aspects, the attenuated interferon alpha-2b portion of the construct includes a deletion of T106 (SEQ ID NO: 215).

In highly preferred aspects of the method, the method is used to treat multiple myeloma in a human subject. In some aspects, the methods comprise administering to the subject lenalidomide and an anti-CD38 antibody-attenuated IFN alpha-2b construct comprising a heavy chain variable region comprising the amino acid sequence of SEQ ID NO: 27 and a light chain variable region comprising the amino acid sequence of SEQ ID NO: 29, and an IgG4 constant region, and comprising an attenuated IFN alpha-2b molecule comprising the amino acid sequence of SEQ ID NO: 212 or SEQ ID NO: 213. In some aspects, the methods comprise administering to the subject pomalidomide and an anti-CD38 antibody-attenuated IFN alpha-2b construct comprising a heavy chain variable region comprising the amino acid sequence of SEQ ID NO: 27 and a light chain variable region comprising the amino acid sequence of SEQ ID NO: 29, and an IgG4 constant region, and comprising an attenuated IFN alpha-2b molecule comprising the amino acid sequence of SEQ ID NO: 212 or SEQ ID NO: 213.

Also provided is a combination of lenalidomide or pomalidomide and an anti-CD38 antibody-attenuated interferon alpha-2b construct for use in the treatment of any one of B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia or acute lymphocytic leukemia. Also provided is a combination of lenalidomide and an anti-CD38 antibody-attenuated interferon alpha-2b construct for use in the treatment of any one of B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia or acute lymphocytic leukemia. Also provided is a combination of pomalidomide and an anti-CD38 antibody-attenuated interferon alpha-2b construct for use in the treatment of any one of B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia or acute lymphocytic leukemia.

BRIEF DESCRIPTION OF THE DRAWINGS

FIG. 4 shows the effects on survival (Kaplan-Meier graph) of the combination of suboptimal dose levels or dosing intervals of an anti-CD38 antibody fused to attenuated aglycosylated interferon-alpha 2b and lenalidomide in SCID mice implanted with the human myeloma cell line NCI-H929.

DETAILED DESCRIPTION

Figure 1:
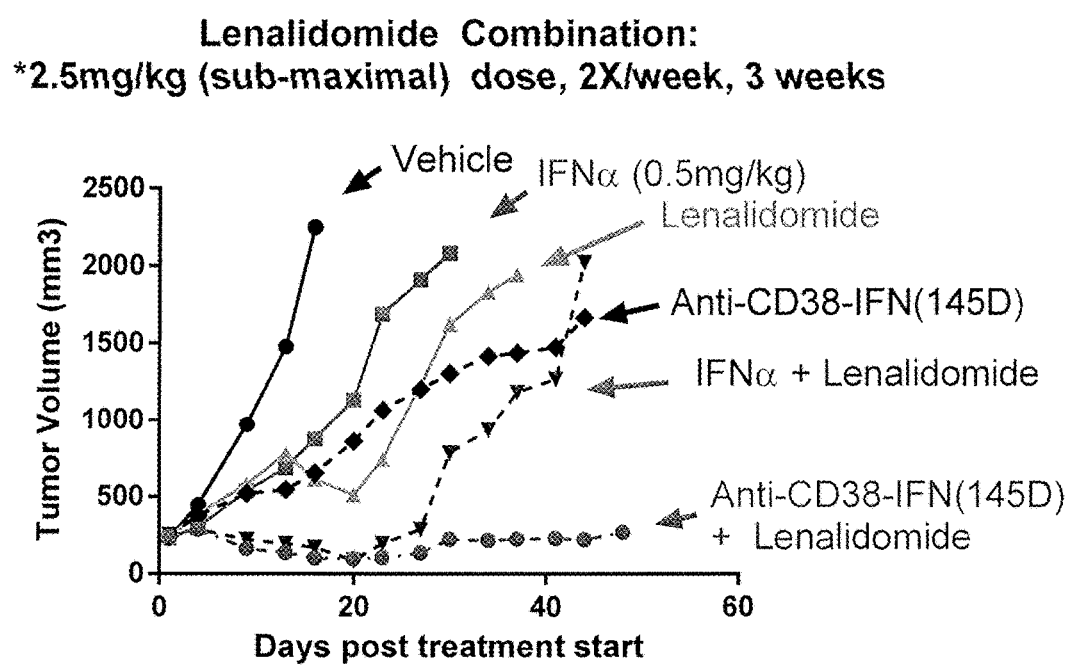
FIG. 1 shows median tumor volume in SCID mice with a multiple myeloma tumor xenograft as a function of time following treatment with either a vehicle control, a free-non-attenuated interferon-alpha 2b (IFN-alpha), a construct including an anti-CD38 antibody fused to attenuated interferon alpha 2b (145D) alone, lenalidomide alone, a combination of free-non-attenuated interferon-alpha and lenalidomide, or a combination of the anti-CD38-attenuated interferon alpha fusion construct and lenalidomide. The anti-CD38 antibody-attenuated interferon alpha fusion construct was administered in a dose that generated sub-maximal tumor inhibition. The wild type interferon was administered at a dose of 0.5 mg/kg, which is equivalent in molar quantity to the amount of interferon administered as a component of the anti-CD38-attenuated interferon alpha 2b construct. Lenalidomide was administered daily for 21 days at 25 mg/kg via intraperitoneal injection.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

The terms subject and patient are used interchangeably and include any mammals, including companion and farm mammals, as well as rodents, including mice, rabbits, and rats, and other rodents. Non-human primates, such as Cynomolgus monkeys, are more preferred, and human beings are highly preferred.

A molecule such as an antibody has been "isolated" if it has been altered and/or removed from its natural environment by human intervention.

As used herein, the singular forms "a," "an," and "the" include plural referents unless expressly stated otherwise.

As used herein, the term "resistance" in any respect of a cancer, tumor, malignancy, or pre-malignancy described herein refers to the cancer, tumor, malignancy, or pre-malignancy being refractory to, or failing to completely respond to or be eliminated by treatment with lenalidomide or pomalidomide, and/or to treatment with treatment with the CD38-attenuated IFN alpha 2b construct. The resistance may occur at the beginning of treatment or may take hold during treatment following a period of positive responsiveness.

"Synergy" or as used herein with respect to the tumor-treating effects of the combination of lenalidomide or pomalidomide and an anti-CD38 antibody-attenuated-interferon alpha-2b construct (e.g., synergistic tumor treatment), comprises tumor growth inhibition, including tumor suppression, tumor growth or re-growth delay, and/or substantial elimination of established tumors, and including inhibition of re-establishment of the tumor following cessation of the treatment, that is significantly greater in terms of the amount, degree, extent of inhibition, and/or rate, and/or significantly longer significantly longer in terms of the time of inhibited re-establishment relative to the tumor-treating effects of lenalidomide or pomalidomide or the anti-CD38 antibody-attenuated-interferon alpha-2b construct alone, or relative to an additive tumor treating effect of the agents in isolation. Thus, a "synergistically effective amount" of lenalidomide or pomalidomide or a "synergistically effective amount" of an anti-CD38 antibody-attenuated-interferon alpha-2b construct is an amount at which "synergy" of the lenalidomide or pomalidomide and an anti-CD38 antibody-attenuated-interferon alpha-2b construct occurs, including an amount at which both agents synergize to substantially inhibit, delay, or suppress tumor growth, substantially eliminate established tumors, and/or substantially inhibit, delay, or suppress tumor re-establishment.

An anti-CD38 antibody-attenuated interferon alpha 2b construct comprises an antibody that specifically binds to CD38 which is joined to an attenuated interferon (IFN) alpha-2b. The antibody may be joined to the IFN alpha-2b by conjugation, cross-linking, or by fusion via a linker or via a peptide bond between the antibody and the IFN molecule.

It has been observed in accordance with the disclosure that an anti-CD38 antibody-attenuated-interferon alpha-2b construct can synergize with lenalidomide or pomalidomide to inhibit tumor growth and, in some cases, eliminate established multiple myeloma tumors in vivo. This synergy was superior to a mere additive effect. For example, it was further observed that the majority of tumors treated with this combination did not re-establish during or following cessation of the treatment, whereas tumors treated with either a suboptimal dose of lenalidomide or pomalidomide or a suboptimal dosage of the anti-CD38 antibody-attenuated IFN alpha2b construct alone re-established during treatment and continued to grow in volume following treatment cessation. It was further observed that this combination could overcome a pre-existing or induced resistance of the tumor to lenalidomide. Accordingly, the disclosure features combination therapies for cancer treatment, and preferably for multiple myeloma treatment. The disclosure features combination therapy systems comprising an anti-CD38 antibody-attenuated interferon alpha-2b construct and lenalidomide or pomalidomide, compositions comprising an anti-CD38 antibody-attenuated interferon alpha-2b construct and lenalidomide or pomalidomide, methods for treating cancer by administering an anti-CD38 antibody-attenuated interferon alpha-2b construct and lenalidomide or pomalidomide to a cancer patient, and kits comprising an anti-CD38 antibody-attenuated interferon alpha-2b construct and lenalidomide or pomalidomide and instructions for using the construct and lenalidomide or pomalidomide as a combination therapy in a method for treating cancer. The disclosure also features methods for enhancing the anti-tumor activity of lenalidomide or pomalidomide treatment, by combining lenalidomide treatment with an treatment with an anti-CD38 antibody-attenuated interferon alpha-2b construct. Alternatively or in addition, the disclosure features methods for enhancing treatment with an anti-CD38 antibody-attenuated interferon alpha-2b construct by combining with lenalidomide or pomalidomide treatment. Methods described herein may be carried out in vitro, ex vivo, in vivo, or in situ.

In one aspect, the disclosure features a combination therapy comprising an anti-CD38 antibody-attenuated IFN-alpha 2b construct and lenalidomide or pomalidomide. The anti-CD38 antibody-attenuated IFN-alpha 2b construct and the lenalidomide or pomalidomide are preferably in an amount effective for treating a tumor. In some aspects, the anti-CD38 antibody-attenuated IFN-alpha 2b construct and the lenalidomide or pomalidomide are in a synergistically effective amount for treating a tumor. The tumor may be B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia, or acute lymphocytic leukemia. In some aspects, a combination therapy comprises a composition comprising an anti-CD38 antibody-attenuated IFN-alpha 2b construct and a pharmaceutically acceptable carrier and a composition comprising lenalidomide or pomalidomide and a pharmaceutically acceptable carrier.

As part of the construct, the anti-CD38 antibody may be a monoclonal antibody, and more preferably is a full-length monoclonal antibody comprising a variable region heavy chain and a variable region light chain. In some aspects, an anti-CD38 antibody may comprise derivatives or fragments or portions of antibodies that retain the CD38-binding specificity, and also preferably retain most or all of the affinity, of the parent antibody molecule (e.g., for CD38). For example, derivatives may comprise at least one variable region (either a heavy chain or light chain variable region). Other examples of suitable antibody derivatives and fragments include, without limitation, antibodies with polyepitopic specificity, bispecific antibodies, multi-specific antibodies, diabodies, single-chain molecules, as well as FAb, F(Ab')2, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or dimers, light chain monomers or dimers, dimers consisting of one heavy and one light chain, and other multimers. Single chain Fv antibodies may be multivalent. All antibody isotypes may be used to produce antibody derivatives, fragments, and portions. Antibody derivatives, fragments, and/or portions may be recombinantly produced and expressed by any cell type, prokaryotic or eukaryotic.

For use in the treatment of humans, non-human derived antibodies may be structurally altered to be less antigenic upon administration to a human patient, including by deimmunization, chimerization or humanization or superhumanization. In some aspects, the antibodies are humanized antibodies. Humanized antibodies are those wherein the amino acids directly involved in antigen binding, e.g., the complementarity determining regions (CDR), and in some cases the framework regions (FR), or portions thereof, of the heavy and/or light chains are not of human origin, while the rest of the amino acids in the antibody are human or otherwise of human origin, e.g., a human antibody scaffold. Humanized antibodies also include antibodies in which one or more residues of the human protein are modified by one or more amino acid substitutions and/or one or more FR residues of the human protein are replaced by corresponding non-human residues. Humanized antibodies may also comprise residues which are found in neither the human antibody or in the non-human antibody. A humanized antibody may be a super-humanized antibody, e.g., as described in U.S. Pat. No. 7,732,578. The antibodies may be humanized chimeric antibodies. Humanized antibodies also include antibodies with constant region sequences, e.g., variable region framework sequences, that are artificial consensus sequences based on multiple human antibodies.

In highly preferred aspects, the anti-CD38 antibodies are fully human. Fully human antibodies are those where the whole molecule is human or otherwise of human origin, or includes an amino acid sequence identical to or substantially identical to human antibody sequences. Fully human antibodies include those obtained from a human V gene library, for example, where human genes encoding variable regions of antibodies are recombinantly expressed. Fully human antibodies may be expressed in other organisms (e.g., mice and xenomouse technology) or cells from other organisms transformed with genes encoding human antibodies. Fully human antibodies may nevertheless include amino acid residues not encoded by human sequences, e.g., mutations introduced by random or site directed mutations.

The anti-CD38 antibodies may be full length antibodies of any class, for example, IgG1, IgG2 or IgG4. In particular embodiments the anti-CD38 antibodies are full-length IgG4 antibodies. The constant domains of such antibodies are preferably human. The variable regions of such antibodies may be of non-human origin, or preferably are human in origin or are humanized. Antibody fragments may also be used in place of the full length antibodies.

In some aspects, the anti-CD38 antibodies may comprise non-immunoglobulin derived protein frameworks. For example, reference may be made to (Ku & Schutz, Proc. Natl. Acad. Sci. USA 92: 6552-6556, 1995) which describes a four-helix bundle protein cytochrome b562 having two loops randomized to create CDRs, which have been selected for antigen binding.

Natural sequence variations may exist among heavy and light chains and the genes encoding them, and therefore, persons having ordinary skill in the art would expect to find some level of variation within the amino acid sequences, or the genes encoding them, of the antibodies described and exemplified herein. Encompassed within the term antibody are sequence variants which maintain CD38 binding specificity and which preferably substantially maintain the affinity of the parent antibody. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the disclosure. The antibodies thus include variants having single or multiple amino acid substitutions, deletions, additions, or replacements that retain the biological properties (e.g., binding specificity and binding affinity) of the parent antibodies. The variants are preferably conservative, but may be non-conservative.

Amino acid positions assigned to complementarity determining regions (CDRs) and framework regions (FRs) may be defined according to Kabat Sequences of Proteins of Immunological Interest, National Institutes of Health, Bethesda, Md., 1987 and 1991 (also referred to herein as the Kabat numbering system). In addition, the amino acid positions assigned to CDRs and FRs may be defined according to the Enhanced Chothia Numbering Scheme (www-.bioinfo.org.uk/mdex.html). The heavy chain constant region of an antibody can be defined by the EU numbering system (Edelman, G M et al. (1969)., Proc. Natl. Acad. USA, 63, 78-85).

According to the numbering system of Kabat, VH FRs and CDRs may be positioned as follows: residues 1-30 (FR1), 31-35 (CDR1), 36-49 (FR2), 50-65 (CDR2), 66-94 (FR3), 95-102 (CDR3) and 103-113 (FR4), and VL FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). In some instances, variable regions may increase in length and according to the Kabat numbering system some amino acids may be designated by a number followed by a letter. This specification is not limited to FWRs and CDRs as defined by the Kabat numbering system, but includes all numbering systems, including the canonical numbering system or of Chothia et al. (1987) J. Mol. Biol. 196:901-17; Chothia et al. (1989) Nature 342:877-83; and/or Al-Lazikani et al. (1997) J. Mol. Biol. 273:927-48; the numbering system of Honnegher et al. (2001) J. Mol. Biol., 309:657-70; or the IMGT system discussed in Giudicelli et al., (1997) Nucleic Acids Res. 25:206-11. In some aspects, the CDRs are defined according to the Kabat numbering system.

In some particular aspects, for any of the heavy chain CDR2 subdomains described herein, according to the Kabat numbering system, the five C-terminal amino acids may not participate directly in antigen binding, and accordingly, it will be understood that any one or more of these five C-terminal amino acids may be substituted with another naturally-occurring amino acid without substantially adversely affecting antigen binding. In some aspects, for any of the light chain CDR1 subdomains described herein, according to the Kabat numbering system, the four N-terminal amino acids may not participate directly in antigen binding, and accordingly, it will be understood that any one or more of these four amino acids may be substituted with another naturally-occurring amino acid without substantially adversely affecting antigen binding. For example, as described by Padlan et al. (1995) FASEB J. 9:133-139, the five C terminal amino acids of heavy chain CDR2 and/or the four N-terminal amino acids of light chain CDR1 may not participate in antigen binding. In some aspects, both the heavy chain CDR2 and the light chain CDR1 do not directly participate in antigen binding.

In some aspects, chemical analogues of amino acids may be used in the antibodies described and/or exemplified herein. The use of chemical analogues of amino acids is useful, for example, for stabilizing the molecules such as if required to be administered to a subject. The analogues of the amino acids contemplated herein include, but are not limited to, modifications of side chains, incorporation of unnatural amino acids and/or their derivatives during peptide, polypeptide or protein synthesis and the use of cross-linkers and other methods which impose conformational constraints on the proteinaceous molecule or their analogues.

The anti-CD38 antibodies may comprise post-translational modifications or moieties, which may impact antibody activity or stability. These modifications or moieties include, but are not limited to, methylated, acetylated, glycosylated, sulfated, phosphorylated, carboxylated, and amidated moieties and other moieties that are well known in the art. Moieties include any chemical group or combinations of groups commonly found on immunoglobulin molecules in nature or otherwise added to antibodies by recombinant expression systems, including prokaryotic and eukaryotic expression systems.

Examples of side chain modifications contemplated by the disclosure include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivation, for example, to a corresponding amide. Sulphydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate.

Crosslinkers may be used, for example, to stabilize 3D conformations of the anti-CD38 antibodies and anti-CD38 antibody-attenuated interferon alpha-2b constructs, using homo-bifunctional crosslinkers such as the bifunctional imido esters having $(CH_2)n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In some aspects, the antibodies may be derivatized by known protecting/blocking groups to prevent proteolytic cleavage or enhance activity or stability.

The anti-CD38 antibodies may be affinity matured, or may comprise amino acid changes that decrease immunogenicity, for example, by removing predicted MHC class II-binding motifs. The therapeutic utility of the antibodies described herein may be further enhanced by modulating their functional characteristics, such as antibody-dependent cell-mediated cytotoxicity (ADCC), complement-dependent cytotoxicity (CDC), serum half-life, biodistribution and binding to Fc receptors or the combination of any of these. This modulation can be achieved by protein-engineering, glyco-engineering or chemical methods. Depending on the therapeutic application required, it could be advantageous to either increase or decrease any of these activities. An example of glyco-engineering used the Potelligent® method as described in Shinkawa T. et al. (2003) J. Biol. Chem. 278: 3466-73.

The anti-CD38 antibodies may include modifications that modulate its serum half-life and biodistribution, including modifications that modulate the antibody's interaction with the neonatal Fc receptor (FcRn), a receptor with a key role in protecting IgG from catabolism, and maintaining high serum antibody concentration. Serum half-life modulating modifications may occur in the Fc region of IgG1 or IgG4, including the triple substitution of M252Y/S254T/T256E (Numbering according to the EU numbering system (Edelman, G. M. et al. (1969) Proc. Natl. Acad. USA 63, 78-85)), (e.g., SEQ ID NO: 13, SEQ ID NO: 14, SEQ ID NO: 15, SEQ ID NO: 16), as described in U.S. Pat. No. 7,083,784. Other substitutions may occur at positions 250 and 428, see e.g., U.S. Pat. No. 7,217,797, as well as at positions 307, 380 and 434, see, e.g., WO 00/42072. Examples of constant domain amino acid substitutions which modulate binding to Fc receptors and subsequent function mediated by these receptors, including FcRn binding and serum half-life, are described in U.S. Publ. Nos. 2009/0142340, 2009/0068175, and 2009/0092599. Naked antibodies may have the heavy chain C-terminal lysine omitted or removed to reduce heterogeneity. The substitution of S228P (EU numbering) in the human IgG4 can stabilize antibody Fab-arm exchange in vivo (Labrin et al. (2009) Nature Biotechnology 27:8; 767-773).

The glycans linked to antibody molecules are known to influence interactions of antibody with Fc receptors and glycan receptors and thereby influence antibody activity, including serum half-life. Hence, certain glycoforms that modulate desired antibody activities can confer therapeutic advantage. Methods for generating engineered glycoforms include but are not limited to those described in U.S. Pat. Nos. 6,602,684, 7,326,681, and 7,388,081 and PCT Publ. No. WO 08/006554. Alternatively, the antibody sequences may be modified to remove relevant glycoform-attachment sites.

The anti-CD38 antibodies preferably have a binding affinity for an epitope on CD38 that includes a dissociation constant (Kd) of less than about $1 \times 10^{-4}$ M. In some embodiments, the Kd is less than about $1 \times 10^{-5}$ M. In still other embodiments, the Kd is less than about $1 \times 10^{-6}$ M. In other embodiments, the Kd is less than about $1 \times 10^{-7}$ M. In other embodiments, the Kd is less than about $1 \times 10^{-8}$ M. In other embodiments, the Kd is less than about $1 \times 10^{-9}$ M. In other embodiments, the Kd is less than about $1 \times 10^{-10}$ M. In still other embodiments, the Kd is less than about $1\times10^{-11}$ M. In some embodiments, the Kd is less than about $1\times10^{-12}$ M. In other embodiments, the Kd is less than about $1\times10^{-13}$ M. In other embodiments, the Kd is less than about $1\times10^{-14}$ M. In still other embodiments, the Kd is less than about $1\times10^{-15}$ M. Affinity values refer to those obtained by standard methodologies, including surface plasmon resonance such as Biacore™ analyses or analysis using an Octet® Red 96 (Forte Bio) Dip-and-Read system.

The anti-CD38 antibodies are preferably capable of binding to CD38-positive cells. The antibody may bind to a CD38-positive cell with an $EC_{50}$ value of less than about 100 nM. The antibody may bind to a CD38-positive cell with an $EC_{50}$ value of less than about 75 nM. The antibody may bind to a CD38-positive cell with an $EC_{50}$ value of less than about 50 nM. The antibody may bind to a CD38-positive cell with an $EC_{50}$ value of less than about 30 nM. The antibody may bind to a CD38-positive cell with an $EC_{50}$ value of less than about 25 nM. The antibody may bind to a CD38-positive cell with an $EC_{50}$ value of less than about 20 nM. The antibody may bind to a CD38-positive cell with an $EC_{50}$ value of less than about 18 nM. The antibody may bind to a CD38-positive cell with an $EC_{50}$ value of less than about 15 nM. The antibody may bind to a CD38-positive cell with an $EC_{50}$ value of less than about 13 nM. The antibody may bind to a CD38-positive cell with an $EC_{50}$ value of less than about 10 nM.

An anti-CD38 antibody may comprise a heavy chain comprising the amino acid sequence of SEQ ID NO: 17, SEQ ID NO: 18, SEQ ID NO: 19, or SEQ ID NO: 20. An antibody may comprise a light chain comprising the amino acid sequence of SEQ ID NO: 21, SEQ ID NO: 22, or SEQ ID NO: 23. In some aspects, the heavy chain amino acid sequence of SEQ ID NO: 17 excludes the amino acid sequence of SEQ ID NO: 24. In some aspects, the light chain amino acid sequence of SEQ ID NO: 21 excludes the amino acid sequence of SEQ ID NO: 25. Variants of such anti-CD38 antibodies can be engineered and expressed such that the antibodies have reduced immunogenicity, enhanced stability, and enhanced half life in circulation without a significant loss of specificity or affinity of the antibody to the CD38 antigen. These variant antibodies can be fused to an attenuated interferon.

In some aspects, the anti-CD38 antibody comprises particular heavy and light chain pairs. Any of the heavy chains having the amino acid sequences of SEQ ID NO: 17 may be paired with any light chains having the amino acid sequences of SEQ ID NO: 21. Any of the heavy chains having the amino acid sequences of SEQ ID NO: 18 may be paired with any light chains having the amino acid sequences of SEQ ID NO: 22. Any of the heavy chains having the amino acid sequences of SEQ ID NO: 19 may be paired with any light chains having the amino acid sequences of SEQ ID NO: 21. Any of the heavy chains having the amino acid sequences of SEQ ID NO: 20 may be paired with any light chains having the amino acid sequences of SEQ ID NO: 23.

In some preferred aspects, the anti-CD38 antibody comprises a heavy and light chain pair of Table 1, Table 2, or Table 3. In more preferred aspects, the anti-CD38 antibody comprises a heavy and light chain pair of Table 4. In more preferred aspects, the anti-CD38 antibody comprises a heavy chain variable region comprising the amino acid sequence of SEQ ID NO: 27 and a light chain variable region comprising the amino acid sequence of SEQ ID NO: 29.

TABLE 1

Heavy and Light Chain Variable Region Pairs

| Antibody Name | Variable Heavy SEQ ID NO: (amino acid) | Variable Light SEQ ID NO: (amino acid) |
|---|---|---|
| A02.10 | 208 | 25 |
| A02.11 | 209 | 25 |
| A02.112 | 43 | 77 |
| A02.12 | 43 | 77 |
| A02.13 | 44 | 77 |
| A02.16 | 43 | 104 |
| A02.17 | 43 | 105 |
| A02.18 | 43 | 85 |
| A02.19 | 43 | 86 |
| A02.2 | 24 | 77 |
| A02.20 | 43 | 87 |
| A02.21 | 43 | 88 |
| A02.22 | 43 | 89 |
| A02.23 | 43 | 90 |
| A02.24 | 43 | 91 |
| A02.25 | 43 | 92 |
| A02.26 | 43 | 93 |
| A02.27 | 43 | 94 |
| A02.28 | 43 | 95 |
| A02.29 | 43 | 96 |
| A02.3 | 206 | 77 |
| A02.30 | 43 | 97 |
| A02.31 | 43 | 98 |
| A02.32 | 43 | 99 |
| A02.33 | 43 | 100 |
| A02.43 | 43 | 101 |
| A02.35 | 43 | 102 |
| A02.36 | 43 | 103 |
| A02.37 | 43 | 78 |
| A02.38 | 43 | 123 |
| A02.39 | 43 | 122 |
| A02.4 | 207 | 77 |
| A02.40 | 131 | 77 |
| A02.41 | 130 | 77 |
| A02.43 | 130 | 123 |
| A02.44 | 131 | 122 |
| A02.46 | 43 | 79 |
| A02.47 | 43 | 80 |
| A02.48 | 43 | 81 |
| A02.49 | 43 | 82 |
| A02.5 | 208 | 77 |
| A02.50 | 43 | 83 |
| A02.51 | 43 | 84 |
| A02.52 | 43 | 106 |
| A02.53 | 43 | 107 |
| A02.54 | 43 | 108 |
| A02.55 | 43 | 109 |
| A02.56 | 43 | 110 |
| A02.57 | 43 | 111 |
| A02.58 | 43 | 112 |
| A02.59 | 43 | 113 |
| A02.6 | 209 | 77 |
| A02.60 | 43 | 114 |
| A02.61 | 43 | 115 |
| A02.62 | 43 | 116 |
| A02.63 | 43 | 117 |
| A02.64 | 43 | 118 |
| A02.65 | 43 | 119 |
| A02.66 | 43 | 102 |
| A02.67 | 43 | 121 |
| A02.8 | 206 | 25 |
| A02.9 | 207 | 25 |
| X02.10 | 208 | 25 |
| X02.100 | 24 | 70 |
| X02.101 | 24 | 71 |
| X02.102 | 24 | 72 |
| X02.103 | 24 | 73 |
| X02.104 | 24 | 74 |
| X02.105 | 24 | 75 |
| X02.106 | 24 | 76 |
| X02.107 | 24 | 77 |
| X02.108 | 41 | 25 |
| X02.11 | 209 | 25 |
| X02.110 | 42 | 25 |

TABLE 1-continued

Heavy and Light Chain Variable Region Pairs

| Antibody Name | Variable Heavy SEQ ID NO: (amino acid) | Variable Light SEQ ID NO: (amino acid) |
|---|---|---|
| X02.114 | 33 | 124 |
| X02.115 | 33 | 125 |
| X02.116 | 33 | 126 |
| X02.117 | 33 | 127 |
| X02.118 | 43 | 128 |
| X02.119 | 43 | 129 |
| X02.120 | 45 | 128 |
| X02.121 | 46 | 128 |
| X02.122 | 47 | 128 |
| X02.123 | 48 | 128 |
| X02.124 | 45 | 129 |
| X02.125 | 46 | 129 |
| X02.126 | 47 | 129 |
| X02.127 | 48 | 129 |
| X02.68 | 210 | 25 |
| X02.69 | 31 | 25 |
| X02.70 | 32 | 25 |
| X02.71 | 33 | 25 |
| X02.72 | 34 | 25 |
| X02.73 | 35 | 25 |
| X02.74 | 36 | 25 |
| X02.75 | 37 | 25 |
| X02.76 | 38 | 25 |
| X02.77 | 39 | 25 |
| X02.78 | 40 | 25 |
| X02.8 | 206 | 25 |
| X02.80 | 24 | 50 |
| X02.81 | 24 | 51 |
| X02.82 | 24 | 52 |
| X02.83 | 24 | 53 |
| X02.84 | 24 | 54 |
| X02.85 | 24 | 55 |
| X02.86 | 24 | 56 |
| X02.87 | 24 | 57 |
| X02.88 | 24 | 58 |
| X02.89 | 24 | 59 |
| X02.9 | 207 | 25 |
| X02.90 | 24 | 60 |
| X02.91 | 24 | 61 |
| X02.92 | 24 | 62 |
| X02.93 | 24 | 63 |
| X02.94 | 24 | 64 |
| X02.95 | 24 | 65 |
| X02.96 | 24 | 66 |
| X02.97 | 24 | 67 |
| X02.98 | 24 | 68 |
| X02.99 | 24 | 69 |

TABLE 2

Heavy and Light Chain Variable Region Pairs

| Antibody Name | Variable Heavy SEQ ID NO: (amino acid) | Variable Light SEQ ID NO: (amino acid) |
|---|---|---|
| A10.1 | 139 | 167 |
| A10.10 | 147 | 167 |
| A10.11 | 148 | 167 |
| A10.12 | 149 | 167 |
| A10.13 | 150 | 167 |
| A10.14 | 151 | 167 |
| A10.15 | 152 | 167 |
| A10.16 | 153 | 167 |
| A10.17 | 27 | 171 |
| A10.18 | 27 | 172 |
| A10.19 | 27 | 173 |
| A10.2 | 140 | 167 |
| A10.20 | 27 | 174 |
| A10.21 | 27 | 29 |
| A10.22 | 27 | 175 |

TABLE 2-continued

Heavy and Light Chain Variable Region Pairs

| Antibody Name | Variable Heavy SEQ ID NO: (amino acid) | Variable Light SEQ ID NO: (amino acid) |
|---|---|---|
| A10.23 | 27 | 176 |
| A10.24 | 27 | 177 |
| A10.25 | 27 | 178 |
| A10.26 | 27 | 179 |
| A10.27 | 27 | 180 |
| A10.28 | 27 | 181 |
| A10.29 | 27 | 182 |
| A10.3 | 28 | 167 |
| A10.30 | 27 | 183 |
| A10.31 | 27 | 184 |
| A10.32 | 27 | 185 |
| A10.35 | 154 | 167 |
| A10.36 | 27 | 186 |
| A10.38 | 26 | 167 |
| A10.39 | 26 | 171 |
| A10.4 | 141 | 167 |
| A10.40 | 26 | 172 |
| A10.41 | 26 | 173 |
| A10.42 | 26 | 174 |
| A10.43 | 26 | 29 |
| A10.44 | 26 | 175 |
| A10.45 | 26 | 176 |
| A10.46 | 26 | 177 |
| A10.47 | 26 | 178 |
| A10.48 | 26 | 179 |
| A10.49 | 26 | 180 |
| A10.5 | 142 | 167 |
| A10.50 | 26 | 181 |
| A10.51 | 26 | 182 |
| A10.52 | 26 | 183 |
| A10.53 | 26 | 184 |
| A10.54 | 26 | 185 |
| A10.57 | 26 | 186 |
| A10.59 | 27 | 167 |
| A10.6 | 143 | 167 |
| A10.7 | 144 | 167 |
| A10.8 | 145 | 167 |
| A10.9 | 146 | 167 |
| A10A2.0 (chimeric) | 132 | 163 |
| A10A2.1 | 133 | 164 |
| A10A2.10 | 134 | 166 |
| A10A2.11 | 134 | 167 |
| A10A2.12 | 134 | 168 |
| A10A2.13 | 134 | 169 |
| A10A2.14 | 134 | 170 |
| A10A2.15 | 135 | 164 |
| A10A2.16 | 135 | 165 |
| A10A2.17 | 135 | 166 |
| A10A2.18 | 135 | 167 |
| A10A2.19 | 135 | 168 |
| A10A2.2 | 133 | 165 |
| A10A2.20 | 135 | 169 |
| A10A2.21 | 135 | 170 |
| A10A2.22 | 26 | 164 |
| A10A2.23 | 26 | 165 |
| A10A2.24 | 26 | 166 |
| A10A2.25 | 26 | 167 |
| A10A2.26 | 26 | 168 |
| A10A2.27 | 26 | 169 |
| A10A2.28 | 26 | 170 |
| A10A2.29 | 136 | 164 |
| A10A2.3 | 133 | 166 |
| A10A2.30 | 136 | 165 |
| A10A2.31 | 136 | 166 |
| A10A2.32 | 136 | 167 |
| A10A2.33 | 136 | 168 |
| A10A2.34 | 136 | 169 |
| A10A2.35 | 136 | 170 |
| A10A2.36 | 137 | 164 |
| A10A2.37 | 137 | 165 |
| A10A2.38 | 137 | 166 |
| A10A2.39 | 137 | 167 |
| A10A2.4 | 133 | 167 |

TABLE 2-continued

Heavy and Light Chain Variable Region Pairs

| Antibody Name | Variable Heavy SEQ ID NO: (amino acid) | Variable Light SEQ ID NO: (amino acid) |
|---|---|---|
| A10A2.40 | 154 | 168 |
| A10A2.41 | 137 | 169 |
| A10A2.42 | 137 | 170 |
| A10A2.43 | 137 | 164 |
| A10A2.44 | 138 | 165 |
| A10A2.45 | 138 | 166 |
| A10A2.46 | 138 | 167 |
| A10A2.47 | 138 | 168 |
| A10A2.48 | 138 | 169 |
| A10A2.49 | 138 | 170 |
| A10A2.5 | 133 | 168 |
| A10A2.50 | 27 | 164 |
| A10A2.51 | 27 | 165 |
| A10A2.52 | 27 | 166 |
| A10A2.53 | 27 | 167 |
| A10A2.54 | 27 | 168 |
| A10A2.55 | 27 | 169 |
| A10A2.56 | 27 | 170 |
| A10A2.6 | 133 | 169 |
| A10A2.7 | 133 | 170 |
| A10A2.8 | 134 | 164 |
| A10A2.9 | 134 | 165 |
| X10.100 | 155 | 30 |
| X10.101 | 156 | 30 |
| X10.102 | 157 | 30 |
| X10.103 | 158 | 30 |
| X10.104 | 159 | 30 |
| X10.105 | 160 | 30 |
| X10.106 | 161 | 30 |
| X10.107 | 162 | 30 |
| X10.108 | 155 | 189 |
| X10.109 | 156 | 189 |
| X10.110 | 157 | 189 |
| X10.111 | 158 | 189 |
| X10.112 | 159 | 189 |
| X10.113 | 160 | 189 |
| X10.114 | 161 | 189 |
| X10.115 | 162 | 189 |
| X10.116 | 155 | 190 |
| X10.117 | 156 | 190 |
| X10.118 | 157 | 190 |
| X10.119 | 158 | 190 |
| X10.120 | 159 | 190 |
| X10.121 | 160 | 190 |
| X10.122 | 161 | 190 |
| X10.123 | 162 | 190 |
| X10.124 | 155 | 191 |
| X10.125 | 156 | 191 |
| X10.126 | 157 | 191 |
| X10.127 | 158 | 191 |
| X10.128 | 159 | 191 |
| X10.129 | 160 | 191 |
| X10.130 | 161 | 191 |
| X10.131 | 162 | 191 |
| X10.132 | 155 | 192 |
| X10.133 | 156 | 192 |
| X10.134 | 157 | 192 |
| X10.135 | 158 | 192 |
| X10.136 | 159 | 192 |
| X10.137 | 160 | 192 |
| X10.138 | 161 | 192 |
| X10.139 | 162 | 192 |
| X10.140 | 155 | 193 |
| X10.141 | 156 | 193 |
| X10.142 | 157 | 193 |
| X10.143 | 158 | 193 |
| X10.144 | 159 | 193 |
| X10.145 | 160 | 193 |
| X10.146 | 161 | 193 |
| X10.147 | 162 | 193 |
| X10.60 | 27 | 187 |
| X10.61 | 27 | 188 |
| X10.62 | 27 | 30 |
| X10.63 | 27 | 189 |
| X10.64 | 27 | 190 |
| X10.65 | 27 | 191 |
| X10.66 | 27 | 192 |
| X10.67 | 27 | 193 |
| X10.68 | 155 | 167 |
| X10.69 | 156 | 167 |
| X10.70 | 157 | 167 |
| X10.71 | 158 | 167 |
| X10.72 | 159 | 167 |
| X10.73 | 160 | 167 |
| X10.74 | 161 | 167 |
| X10.75 | 162 | 167 |
| X10.76 | 26 | 187 |
| X10.77 | 26 | 188 |
| X10.78 | 26 | 30 |
| X10.79 | 26 | 189 |
| X10.80 | 26 | 190 |
| X10.81 | 26 | 191 |
| X10.82 | 26 | 192 |
| X10.83 | 26 | 193 |
| X10.84 | 155 | 187 |
| X10.85 | 156 | 187 |
| X10.86 | 157 | 187 |
| X10.87 | 158 | 187 |
| X10.88 | 159 | 187 |
| X10.89 | 160 | 187 |
| X10.90 | 161 | 187 |
| X10.91 | 162 | 187 |
| X10.92 | 155 | 188 |
| X10.93 | 156 | 188 |
| X10.94 | 157 | 188 |
| X10.95 | 158 | 188 |
| X10.96 | 159 | 188 |
| X10.97 | 160 | 188 |
| X10.98 | 161 | 188 |
| X10.99 | 162 | 188 |

TABLE 3

Heavy and Light Chain Variable Region Pairs

| Antibody Name | Variable Heavy SEQ ID NO: (amino acid) | Variable Light SEQ ID NO: (amino acid) |
|---|---|---|
| X910/12-HC-L0-IFN-alpha (A145D) IgG4 | 130 | 122 |
| X913/15-HC-L0-IFN-alpha (A145D) IgG4 | 131 | 123 |

TABLE 4

Heavy and Light Chain Variable Region Pairs

| Antibody Name | Variable Heavy SEQ ID NO: (amino acid) | Variable Light SEQ ID NO: (amino acid) |
|---|---|---|
| X10.78 | 26 | 30 |
| A10.21 | 27 | 29 |
| A10.43 | 26 | 29 |
| A10.62 | 27 | 30 |
| A10.152 | 28 | 30 |

The anti-CD38 antibody may be an anti-CD38 antibody described in the art. Examples of anti-CD38 antibodies which may be used as described herein include antibodies described in U.S. Pat. No. 5,545,405, 7,829,673, 8,088,896, or 8,153,765, or described in U.S. Publ. Nos. 2002/0164788, 2003/0211553, 2009/0076249, 2009/0123950, or 2010/0285004.

As part of the construct, the anti-CD38 antibody preferably is joined to an attenuated form of IFN alpha 2b. IFN alpha-2b attenuation relates to the biologic activity of interferon achieved by binding to an interferon receptor on a cell surface. Attenuation may be achieved by introducing certain amino acid changes into the interferon protein sequence.

An attenuated interferon molecule is joined to an anti-CD38 antibody such that the antibody may serve as a delivery vehicle for the attenuated interferon, delivering it to CD38-positive cells with a resulting diminution of off-target interferon activity caused by the attenuated interferon molecule. An anti-CD38 antibody-attenuated interferon alpha-2b construct includes, but is not limited to, any antibody described or exemplified herein that binds specifically to CD38 that is joined to an attenuated IFN alpha-2b protein, including an IFN alpha-2b of SEQ ID NO: 3, SEQ ID NO: 4, SEQ ID NO: 5, SEQ ID NO: 6, SEQ ID NO: 7, SEQ ID NO: 211, SEQ ID NO: 212, or SEQ ID NO: 213.

Human CD38 comprises the amino acid sequence of SEQ ID NO: 1, and cynomolgus monkey CD38 comprises the amino acid sequence of SEQ ID NO: 2.

The anti-CD38 antibody is employed as delivery vehicles for the attenuated interferon alpha-2b. Without intending to be limited to any particular theory or mechanism or action, it is believed that the antibody, as a delivery vehicle, compensates for the diminished capacity of the interferon molecule to bind to its receptor (its attenuation). In this sense, the attenuated interferon has reduced capacity to interact with its receptor on healthy cells, and particularly cells that do not express CD38. It is believed that by bringing the attenuated interferon into proximity with its receptor on CD38-positive cells, the antibodies may enhance the capacity of the attenuated interferon to bind to its relevant receptor and induce a therapeutic effect, while exhibiting a diminished capacity to induce undesirable effects on healthy cells that do not express CD38. Joining the attenuated interferon to an anti-CD38 antibody does not significantly affect the capacity of the antibody to specifically bind to CD38 on cells expressing CD38, including cells in vivo.

The antibodies may be fused to attenuated ligands, for example, to form antibody-attenuated ligand constructs, which show an elevated antigen-specificity index (ASI) with respect to activating signaling pathways due to the action of the attenuated ligand on a cell surface receptor. These constructs are based on the observation that, in the context of an antibody-ligand construct, the ligand portion can be mutated in such a way that the ligand activity on antigen-negative cells is dramatically attenuated, while the ligand activity on antigen-positive cells is only modestly, if at all, attenuated. Such constructs display one, two, three, four or five orders of magnitude greater potency on antigen-positive cells compared to antigen negative cells than does the free ligand. In some aspects, the antibody-attenuated ligand construct retains at least 1%, at least 10%, at least 20%, at least 30%, at least 40% or at least 50% of the potency on antigen-positive cells as the non-attenuated free (i.e., not attached to an antibody) ligand. In some aspects, the antibody-attenuated ligand construct retains at least 30%, at least 50%, at least 75% or at least 90% of the maximal activity of the non-attenuated free (i.e. not attached to an antibody) ligand. Maximal activity includes the amount of signaling activity (or downstream effect thereof) at the high, plateau portion of a dose-response curve, where further increases in the agent does not further increase the amount of response.

In some aspects, the antibody fusion to and inclusion of an attenuating mutation(s) in the interferon ligand increases the antigen-specificity index (ASI) by greater than 10-fold, preferably greater than 50-fold, preferably greater than 100-fold, preferably greater than 1000-fold, or preferably greater than 10,000 fold, relative to an antibody without a fusion. The ASI comprises the fold-increased potency in signaling activity of the antibody-IFN ligand construct relative to the free non-mutated polypeptide ligand on target antigen-positive cells, multiplied by the fold decreased potency in signaling activity relative to the free non-mutated polypeptide ligand on target antigen-negative cells. Potency may be quantitatively represented by the $EC_{50}$ value, which is the mathematical midpoint of a dose-response curve, in which the dose refers to the concentration of ligand or antibody-ligand construct in an assay, and response refers to the quantitative response of the cells to the signaling activity of the ligand at a particular dose. Thus, for example, when a first compound is shown to possess an $EC_{50}$ (expressed for example in Molar units) that is 10-fold lower than a second compound's $EC_{50}$ on the same cells, typically when measured by the same method, the first compound is said to have a 10-fold higher potency. Conversely, when a first compound is shown to possess an $EC_{5}0$ that is 10-fold higher than a second compound's $EC_{50}$ on the same cells, typically when measured by the same method, the first compound is said to have a 10-fold lower potency.

The interferon alpha-2b ligand joined to the anti-CD38 antibody preferably comprises alterations in its amino acid sequence, including point mutations and/or deletions that render the interferon less active in stimulating its respective receptors on cells that lack cell surface expression of the CD38 antigen to which the antibody binds. A preferred variant of interferon alpha comprises an amino acid change at position 168 of the interferon alpha 2b amino acid sequence of SEQ ID NO: 8. For example, the amino acid at position 168, which is an alanine in the parent IFN-alpha2b molecule (SEQ ID NO: 8), is preferably changed to a glycine (Gly/G) (SEQ ID NO: 6) or aspartic acid (Asp/D) (SEQ ID NO: 3). In some preferred aspects, the IFN-alpha2b is truncated at its N-terminus when the IFN-alpha2b is fused to an IgG heavy chain constant domain such as the human IgG1 or human IgG4 heavy chain constant domain. The truncated IFN-alpha2b does not have the twenty three N-terminal amino acids of SEQ ID NO: 8 (Met 1 through Gly 23 are deleted), and the truncated IFN-alpha2b comprises the amino acid sequence of SEQ ID NO: 4. The truncated IFN-alpha2b may also comprise the amino acid change at what was formerly position 168, but which becomes position 145 in the truncated protein (e.g., alanine 168 becomes alanine 145). In the truncated IFN-alpha2b, the alanine is preferably changed to a glycine (Gly/G) (SEQ ID NO: 7) or aspartic acid (Asp/D) (SEQ ID NO: 5). Interferon with the A145D alteration (SEQ ID NO: 3 or SEQ ID NO: 5) is particularly preferred as the attenuated interferon joined to the antibodies of the disclosure. Any of these point-mutated, attenuated versions of IFN-alpha may be joined to any antibody described herein, for example, as an antibody-attenuated interferon construct. In some aspects, joining an unmutated IFN alpha-2b protein, such as SEQ ID NO: 8, to an anti-CD38 antibody attenuates the biologic activities of the interferon molecule. In this disclosure, attenuated interferon, attenuated IFN alpha-2b, IFN alpha-2b A145D, and IFN alpha-2b A145G are used interchangeably.

In highly preferred aspects, the anti-CD38 antibody is fused to an attenuated interferon alpha 2b comprising the amino acid sequence of SEQ ID NO: 211, SEQ ID NO: 212, or SEQ ID NO: 213. In these attenuated interferon alpha 2b molecules, the N-terminal 23 amino acids of the parent interferon alpha 2b molecule are deleted, resulting in a truncation variant having 165 amino acids such that amino acid number 24 of the parent interferon alpha 2b molecule becomes amino acid number 1 of the truncation variant. In these truncation variants, certain additional amino acids may be substituted. For example, the threonine at position 106 may be changed to an alanine (T106A) in order to remove a glycosylation site (aglycosylated interferon alpha 2b) (e.g., SEQ ID NO: 211). Additionally, the alanine at position 145 of the truncation variant may be changed to aspartic acid (SEQ ID NO: 212) or may be changed to glycine (SEQ ID NO: 213).

In some aspects, the linkage between the antibody and the interferon comprises a fusion, for example, a peptide bond between the N- or the C-terminus of the interferon and the N- or C-terminus of the heavy or the light chain of the antibody. In one preferred aspect, no linker is present between the antibody and the interferon (other than the ribosomally synthesized peptide bond between the last C-terminal amino acid of the first component of the fusion protein and the N-terminal amino acid of the second component of the fusion protein), and the antibody and interferon are thus directly fused. It is believed that direct fusion, without an intervening linker peptide, provides at least a measurable degree of attenuation of the interferon protein, and it is also believed that this attenuation is additive with the attenuation of the interferon protein that stems from the mutations introduced into the interferon protein, including those described or exemplified herein. For example, in some aspects, the anti-CD38 antibody-attenuated interferon alpha-2b construct comprises the amino acid sequence of SEQ ID NO: 216 (heavy chain and interferon) and the amino acid sequence of SEQ ID NO: 217 (light chain).

In some aspects, the construct includes an intervening stretch of amino acids between the last C-terminal amino acid of the first protein of the construct and the N-terminal amino acid of the second protein of the construct. The number of amino acids in such a peptide linker may be anywhere from 1 to 50 in length, preferably 1-20 in length. The sequences of such linkers could include sequences primarily consisting of glycine and serine, for example, such as the sequence $(G_4S)n$, where n can be any number from 1 to about 10, and preferably is 1 to about 4.

As a therapeutic modality, and as part of a therapy or treatment regimen, the anti-CD38 antibody-attenuated interferon alpha-2b construct is paired with lenalidomide. Lenalidomide, also known as (RS)-3-(4-Amino-1-oxo 1,3-dihydro-2H-isoindol-2-yl)piperidine-2,6-dione, has the chemical formula, Formula I:

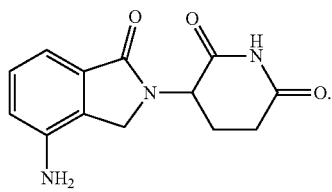

(I)

As an alternative therapeutic modality, and as part of a therapy or treatment regimen, the anti-CD38 antibody-attenuated interferon alpha-2b construct may be paired with pomalidomide. Thus, pomalidomide may be substituted for lenalidomide in any of the systems, kits, methods, compositions, or uses described or exemplified herein. Pomalidomide, also known as (RS)-4-Amino-2-(2,6-dioxopiperidin-3-yl)isoindole-1,3-dione, has the chemical formula, Formula II:

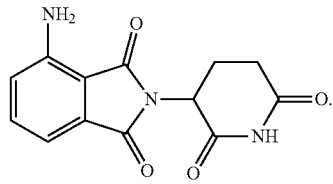

(II)

In some aspects, an anti-CD38 antibody-attenuated interferon alpha-2b construct and lenalidomide or pomalidomide are each comprised in a composition. The composition may be used in accordance with a combination therapy. A combination therapy may comprise a composition of an anti-CD38 antibody-attenuated interferon alpha-2b construct and a separate composition of lenalidomide or pomalidomide, or may comprise a composition of both agents together. A composition may comprise at least one of any suitable auxiliary, such as, but not limited to one or more, diluents, binders, stabilizers, buffers, salts, lipophilic solvents, preservatives, adjuvants, or other suitable carrier and/or excipient. Pharmaceutically acceptable auxiliaries are preferred. The anti-CD38 antibody-attenuated interferon alpha-2b construct and/or lenalidomide or pomalidomide may be formulated with an acceptable carrier such as a pharmaceutically acceptable carrier. Suitable carriers include any media that does not interfere with the biological activity of the antibody and/or the interferon and preferably is not toxic to a host to which it is administered. The carrier may be an aqueous solution, such as water, saline, or alcohol, or a physiologically compatible buffer, such as Hanks's solution, Ringer's solution, or physiological saline buffer. The carrier may contain formulatory agents, such as suspending, stabilizing and/or dispersing agents Pharmaceutical excipients and additives useful in the composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and other known sugars; and polysaccharides or sugar polymers), which can be present singly or in combination, comprising alone or in combination any suitable weight or volume. Exemplary protein excipients include serum albumin, such as human serum albumin (HSA), recombinant human albumin (rHA), gelatin, casein, and other known proteins. Representative amino acids which can also function in a buffering capacity include alanine, glycine, arginine, betaine, histidine, glutamic acid, aspartic acid, cysteine, lysine, leucine, isoleucine, valine, methionine, phenylalanine, and aspartame. One preferred amino acid is histidine. A second preferred amino acid is arginine.

Carbohydrate excipients suitable for use in the composition include, for example, monosaccharides, such as fructose, maltose, galactose, glucose, D-mannose, and sorbose; disaccharides, such as lactose, sucrose, trehalose, and cellobiose; polysaccharides, such as raffinose, melezitose, maltodextrins, dextrans, and starches; and alditols, such as mannitol, xylitol, maltitol, lactitol, xylitol sorbitol (glucitol), and myoinositol. Preferred carbohydrate excipients for use in the disclosure are mannitol, trehalose, and raffinose.

The compositions may include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the compositions are organic acid salts, such as citrate.

The compositions may include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, antimicrobial agents, antioxidants, antistatic agents, surfactants (e.g., polysorbates such as "TWEEN® 20" and "TWEEN® 80"), lipids (e.g., phospholipids, fatty acids), steroids (e.g., cholesterol), and chelating agents (e.g., EDTA).

The compositions may be formulated in sustained release vehicles or depot preparations. For example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administrations. The compositions may be formulated in a suitable controlled-release vehicle, with an adjuvant, or as a depot formulation. Lenalidomide is preferably in a solid dosage form such as a pill or tablet. The construct is preferably in a liquid dosage form for parenteral administration.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

A combination therapy system comprising an anti-CD38 antibody-attenuated interferon alpha-2b construct paired with lenalidomide or pomalidomide may be used, for example, to inhibit, reduce, decrease, block, or prevent proliferation of a cell that expresses CD38 on its surface. A combination therapy comprising an anti-CD38 antibody-attenuated interferon alpha-2b construct paired with lenalidomide or pomalidomide may be used, for example, to induce, facilitate, or enhance apoptosis of a cell that expresses CD38 on its surface. The cell that expresses CD38 may be a lymphocyte, an autoimmune lymphocyte, or a tumor cell such as a leukemia cell, a multiple myeloma cell, or a lymphoma cell. Preferably, a cell that expresses CD38 is a tumor cell, and the tumor cell may be resistant to lenalidomide or pomalidomide, including resistance arising after an initial period of positively responsive treatment, such that the tumor responds positively to the combination therapy.

A combination therapy system comprising an anti-CD38 antibody-attenuated interferon alpha-2b construct paired with lenalidomide or pomalidomide may be used to treat a patient having a tumor that comprises and/or is mediated, at least in part, by cells that express CD38 on their surface. In some aspects, methods for treating a tumor generally comprise administering to a patient in need of treatment of the tumor an anti-CD38 antibody-attenuated interferon alpha-2b construct and lenalidomide or pomalidomide. Each of the construct and lenalidomide or pomalidomide are administered in an amount effective to treat the tumor in the patient. Each of the construct and lenalidomide or pomalidomide may be comprised in a composition, with each agent comprised in either a separate composition or comprised in the same composition. The combination therapy produces a synergy of the construct with the lenalidomide or pomalidomide such that there is one or more of an enhanced inhibition or reduction of proliferation of cells in the tumor, an enhanced induction of apoptosis of cells in the tumor, and/or an enhanced killing of CD38-positive cells in the tumor, relative to tumor cells of the same type that were treated by either an anti-CD38 antibody-attenuated interferon alpha-2b construct or lenalidomide or pomalidomide, but not both. In some aspects, the tumor cells may be resistant to lenalidomide or pomalidomide, including resistance arising after an initial period of positively responsive treatment, such that the tumor responds positively to the combination therapy. Thus, for example, the combination therapy kills tumor cells that have ceased positively responding to treatment with lenalidomide or pomalidomide alone.

In accordance with tumor treatment, the combination therapy of an anti-CD38 antibody-attenuated interferon alpha-2b construct paired with lenalidomide or pomalidomide may inhibit or prevent regrowth and re-establishment of the tumor. Such an inhibition of regrowth and re-establishment may be measured over a period of time, for example, a period of at least about one year, a period of at least about 2 years, a period of at least about 3 years, a period of at least about 5 years, or a period greater than 5 years.

As a combination therapy, an anti-CD38 antibody-attenuated interferon alpha-2b construct and lenalidomide or pomalidomide, or composition comprising an anti-CD38 antibody-attenuated interferon alpha-2b construct and a composition comprising lenalidomide or pomalidomide may be administered to a tumor by administering the anti-CD38 antibody-attenuated interferon alpha-2b construct, or composition thereof, and lenalidomide or composition thereof, to the blood, for example, via subcutaneous or intravenous administration. The anti-CD38 antibody-attenuated interferon alpha-2b construct and lenalidomide or pomalidomide may be administered such that each agent diffuses via blood flow to and/or into the tumor cells. By administering the anti-CD38 antibody-attenuated interferon alpha-2b construct and lenalidomide or pomalidomide to the tumor, the patient to which the anti-CD38 antibody-attenuated interferon alpha-2b construct and lenalidomide or pomalidomide is treated.

Thus, a combination therapy comprises administering to a patient having a tumor and in need of treatment an amount of an anti-CD38 antibody-attenuated interferon alpha-2b construct and an amount of lenalidomide or pomalidomide that is effective to treat the tumor in the patient, e.g., a synergistically effective amount. The tumor may be a lenalidomide-resistant tumor, or may comprise cells that are resistant to lenalidomide or pomalidomide, including resistance arising after an initial period of positively responsive treatment, such that the tumor responds positively to the combination therapy. The anti-CD38 antibody-attenuated interferon alpha-2b construct and lenalidomide or pomalidomide may be administered substantially at the same time, for example, co-administered by way of a composition comprising these agents together, or by administering separate compositions of each agent at the same time. The anti-CD38 antibody-attenuated interferon alpha-2b construct and lenalidomide or pomalidomide may be administered sequentially, with the anti-CD38 antibody-attenuated interferon alpha-2b construct administered before the lenalidomide, or vice versa.

Tumors that may be treated with a combination therapy of an anti-CD38 antibody-attenuated interferon alpha-2b construct and lenalidomide or pomalidomide include, but are not limited to, lenalidomide-resistant forms of, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, hematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, multiple myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor. In an embodiment the tumor is selected from a group of multiple myeloma or non-Hodgkin's lymphoma.

In preferred aspects, a combination therapy of an anti-CD38 antibody-attenuated interferon alpha-2b construct and lenalidomide or pomalidomide is used for treatment of multiple myeloma, early stage multiple myeloma, pre-multiple myeloma, Waldenström's macroglobulinemia, non-Hodgkin's lymphoma, chronic myelogenous leukemia, chronic lymphocytic leukemia or acute lymphocytic leukemia in a patient having multiple myeloma, early stage multiple myeloma, pre-multiple myeloma, Waldenström's macroglobulinemia, non-Hodgkin's lymphoma, chronic myelogenous leukemia, chronic lymphocytic leukemia or acute lymphocytic leukemia, including a lenalidomide-resistant form of multiple myeloma, non-Hodgkin's lymphoma, chronic myelogenous leukemia, chronic lymphocytic leukemia or acute lymphocytic leukemia. In some highly preferred aspects, a combination therapy of an anti-CD38 antibody-attenuated interferon alpha-2b construct and lenalidomide is used for treatment of multiple myeloma, leukemia, or lymphoma in a patient having multiple myeloma, leukemia, or lymphoma, including a lenalidomide-resistant form of multiple myeloma, leukemia, or lymphoma. In some highly preferred aspects a combination therapy of an anti-CD38 antibody-attenuated interferon alpha-2b construct and lenalidomide or pomalidomide is used for treatment of multiple myeloma in a patient having multiple myeloma, including a lenalidomide-resistant form of multiple myeloma. Lenalidomide resistance includes resistance arising after an initial period of positively responsive treatment to lenalidomide, such that the tumor responds positively to the combination therapy.

Use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of tumors are provided. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of B-cell lymphoma. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of multiple myeloma. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of non-Hodgkin's lymphoma. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of chronic myelogenous leukemia. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of chronic lymphocytic leukemia. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of acute lymphocytic leukemia. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of early stage multiple myeloma. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of pre-multiple myeloma. The disclosure also features use of an anti-CD38 antibody-attenuated interferon alpha-2b construct and lenalidomide or pomalidomide, or a composition of an anti-CD38 antibody-attenuated interferon alpha-2b construct and a composition of lenalidomide or pomalidomide, as a combination therapy in the treatment of acute lymphocytic leukemia Waldenström's macroglobulinemia.

In one aspect, the disclosure features kits. The kits comprise an anti-CD38 antibody-attenuated interferon alpha-2b construct, lenalidomide or pomalidomide, and instructions for using the construct and lenalidomide in a combination therapy for the treatment of cancer, including lenalidomide-resistant cancer. The anti-CD38 antibody-attenuated interferon alpha-2b construct and lenalidomide or pomalidomide may each be in separate dosage forms, may each be in a composition as described herein, or may be together in a composition as described herein, or may be separate but intended to be combined or mixed together in a suitable carrier prior to administration to a patient having cancer. In some aspects, the kits comprise a pharmaceutically acceptable carrier and instructions for mixing the anti-CD38 antibody-attenuated interferon alpha-2b construct with the carrier, and instructions for mixing the lenalidomide or pomalidomide with the carrier. The pharmaceutically acceptable carrier for the anti-CD38 antibody-attenuated interferon alpha-2b construct may be the same as or different from the pharmaceutically acceptable carrier for the lenalidomide or pomalidomide. The anti-CD38 antibody-attenuated interferon alpha-2b construct and the lenalidomide or pomalidomide preferably are present in the kit in an amount effective for the treatment of cancer in a patient having the cancer, e.g., a synergistically effective amount, including an amount effective for synergistically treating lenalidomide-resistant cancer, or the kit may include instructions for establishing and/or administering a synergistically effective amount for the treatment of cancer. For parenteral administration, the kit may comprise a device to infuse the anti-CD38 antibody-attenuated interferon alpha-2b construct and/or lenalidomide or pomalidomide, or composition thereof, into a subject, including but not limited to a syringe and needle, or catheter. Lenalidomide resistance include resistance arising after an initial period of positively responsive treatment, such that the tumor responds positively to the combination therapy.

In any of the systems, compositions, kits, methods, and usages described or exemplified in this document, a synergistically effective amount of either or both of the anti-CD38 antibody-attenuated interferon alpha-2b construct and the lenalidomide or pomalidomide may relate to the inclusion of the other agent in the pair. For example, a synergistically effective amount of lenalidomide or pomalidomide may be a function of the synergistically effective amount of the anti-CD38 antibody-attenuated interferon alpha-2b construct, or a synergistically effective amount of the anti-CD38 antibody-attenuated interferon alpha-2b construct may be a function of the synergistically effective amount of lenalidomide or pomalidomide. The anti-CD38 antibody-attenuated interferon alpha-2b construct and the lenalidomide or pomalidomide synergize to produce an enhanced tumor killing effect relative to the tumor killing effect of each agent alone. A synergistically effective amount may vary, for example, according to the age, gender, the overall health of the patient, the physical characteristics of the patient, the type of the tumor, the stage of the tumor, and other factors that would be expected to be known to a practitioner who would administer an anti-CD38 antibody-attenuated interferon alpha-2b construct and the lenalidomide or pomalidomide as a combination therapy to a patient.

The following examples are provided to describe the disclosure in greater detail. They are intended to illustrate, not to limit, the disclosure.

Example 1

Figure 2:
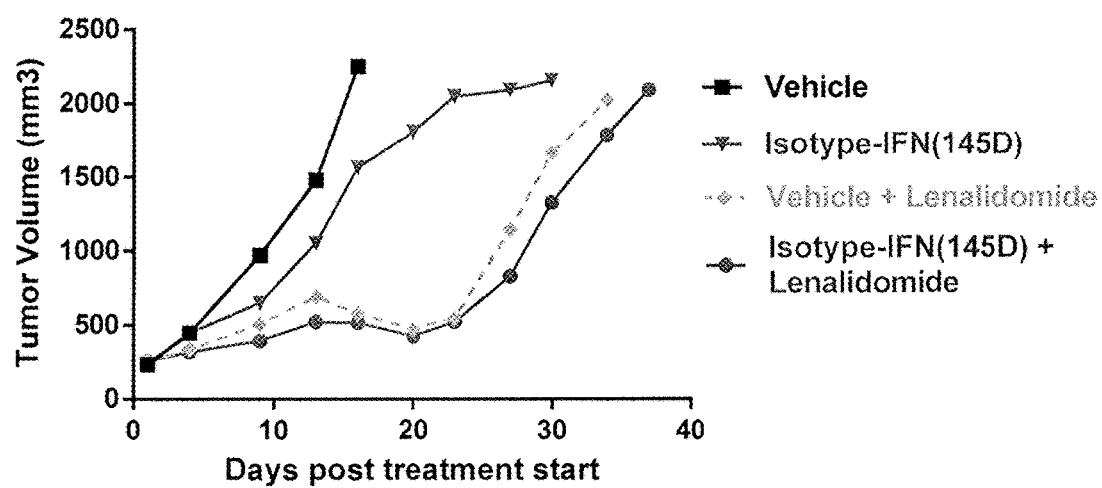
FIG. 2 shows tumor volume in SCID mice with a multiple myeloma tumor xenograft as a function of time following treatment with either a vehicle control, a construct of an isotype-matched antibody (the same isotype as the anti-CD38 antibody from FIG. 1) directed to an irrelevant antigen fused to attenuated interferon alpha (145D), or a combination of the isotype-matched antibody-attenuated interferon alpha fusion construct and lenalidomide. None of these agents or combination of agents was capable of preventing tumor growth, although lenalidomide alone or in combination with an irrelevant fusion construct delayed the onset of rapid tumor growth.
Figure 3A:
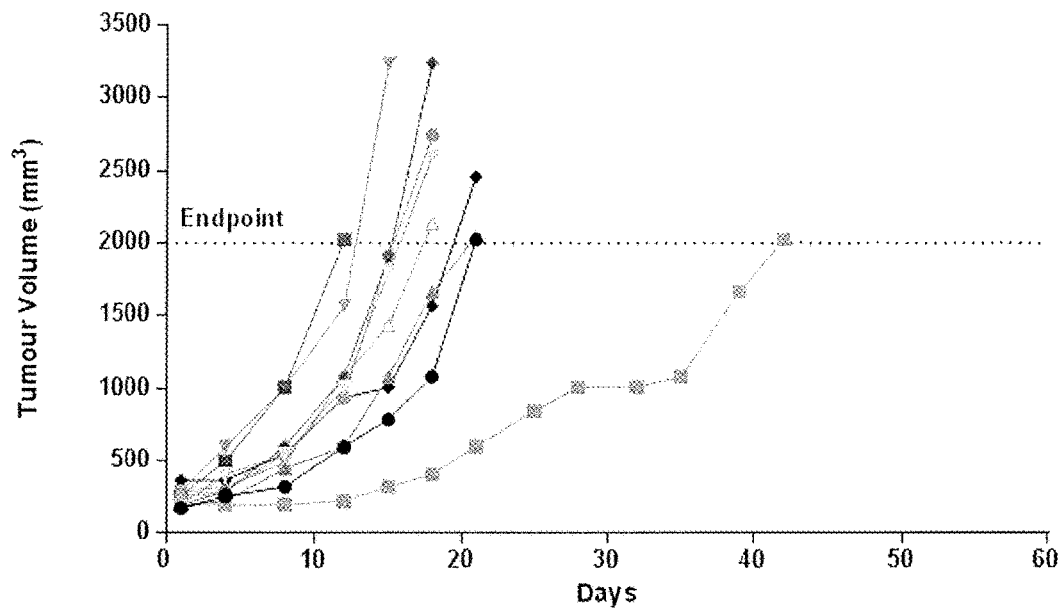
FIG. 3A-3J show tumor volumes in individual SCID mice with a multiple myeloma tumor xenograft NCI-H929 as a function of time following treatment with either a vehicle control, lenalidomide alone daily at 25 mg/kg via intraperitoneal injection for 21 days, an anti-CD38 antibody (A10.21) fused to an attenuated aglycosylated human interferon-alpha 2b (T106A) at a dose or dose frequency for sub-maximal tumor inhibition or various combinations of lenalidomide and anti-CD38 antibody fused to attenuated aglycosylated interferon at doses or dose frequencies for sub-maximal tumor inhibition as defined in Table 5.
Figure 3B:
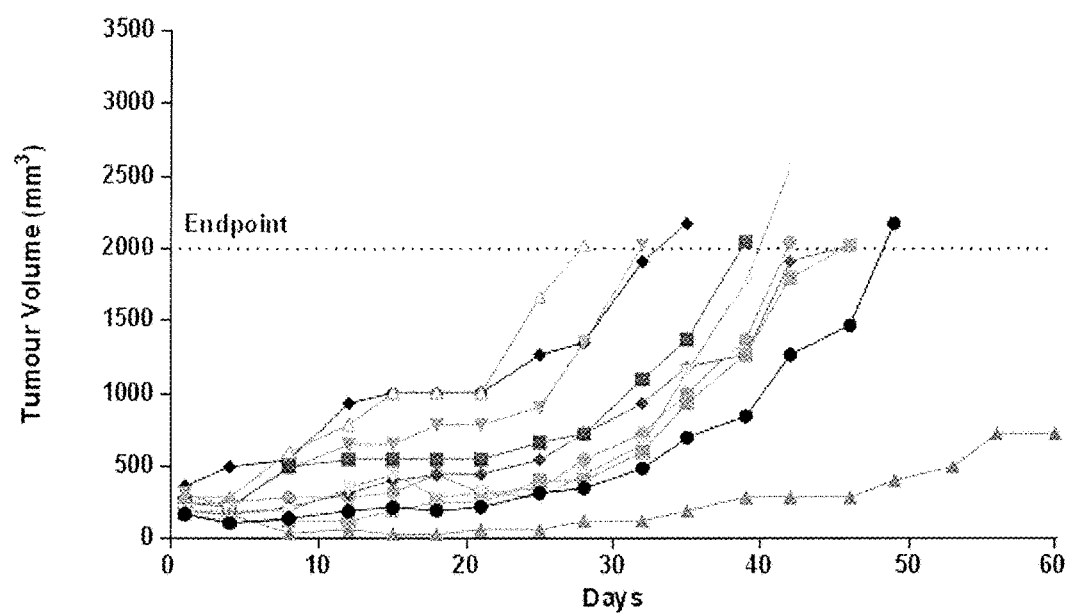
Figure 3C:
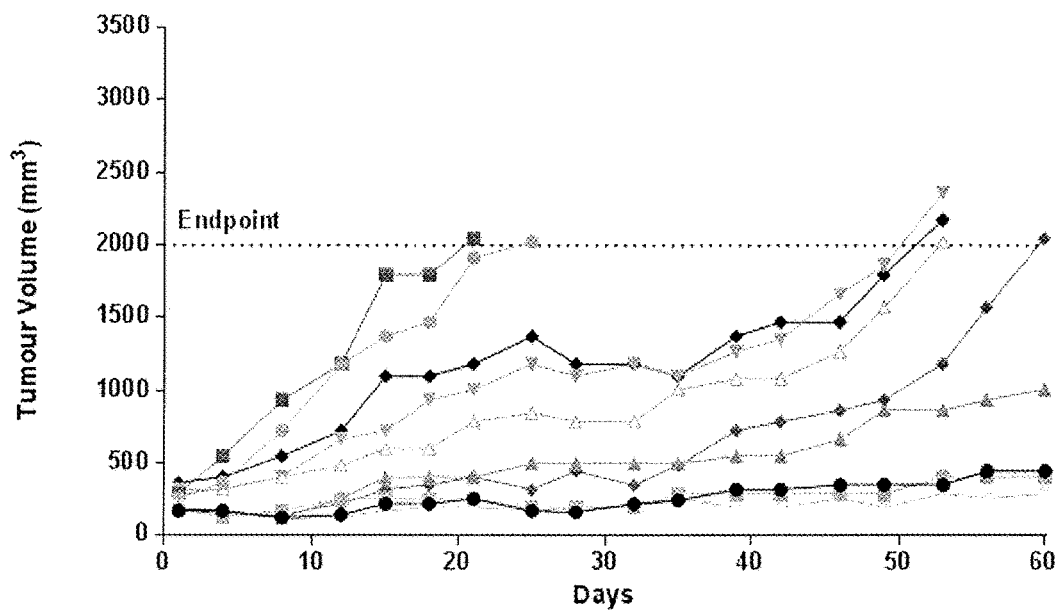
Figure 3D:
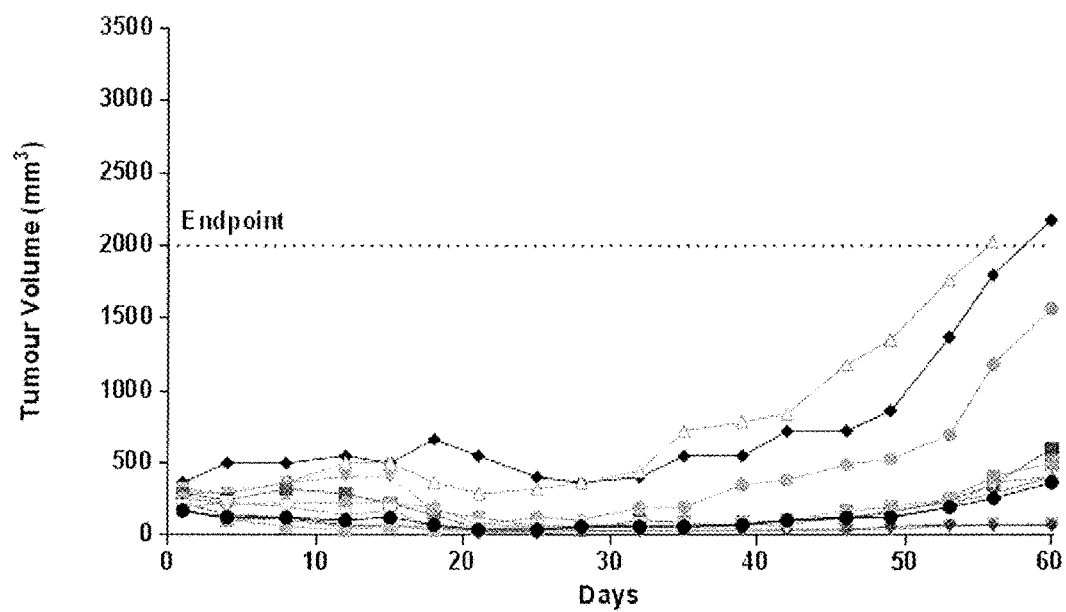
Figure 3E:
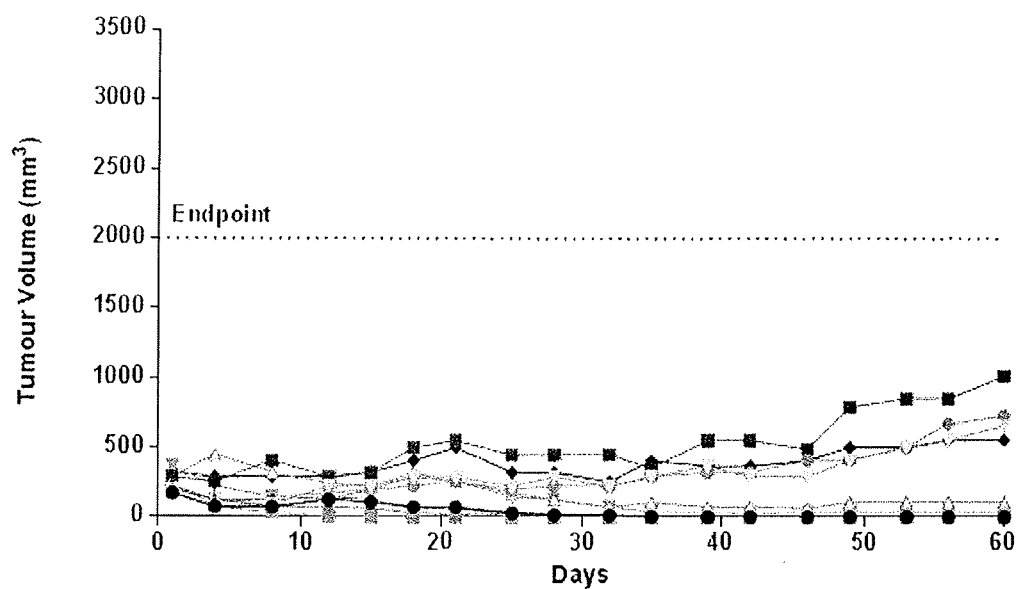
Figure 3F:
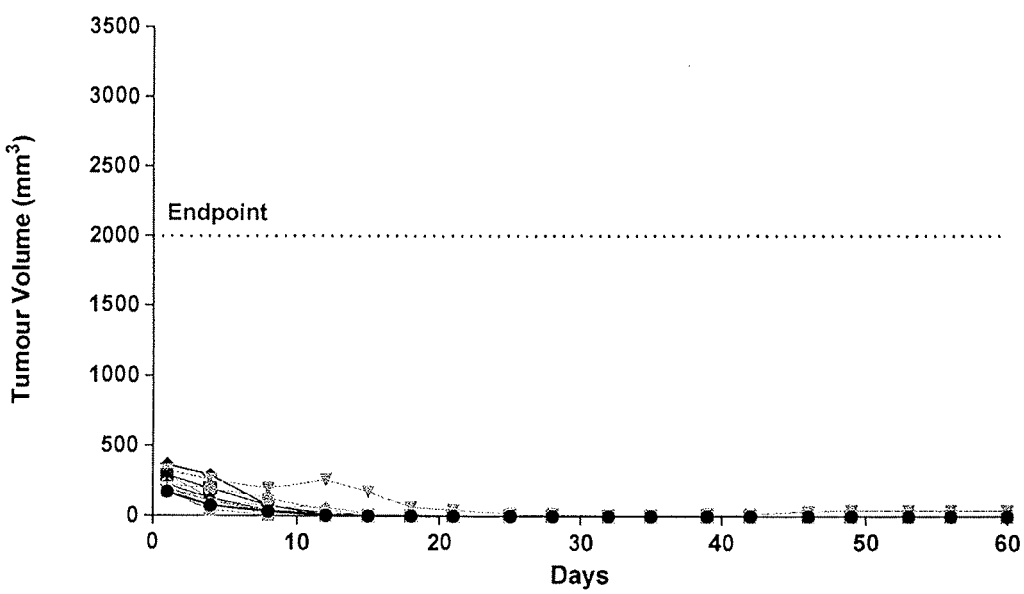
Figure 3G:
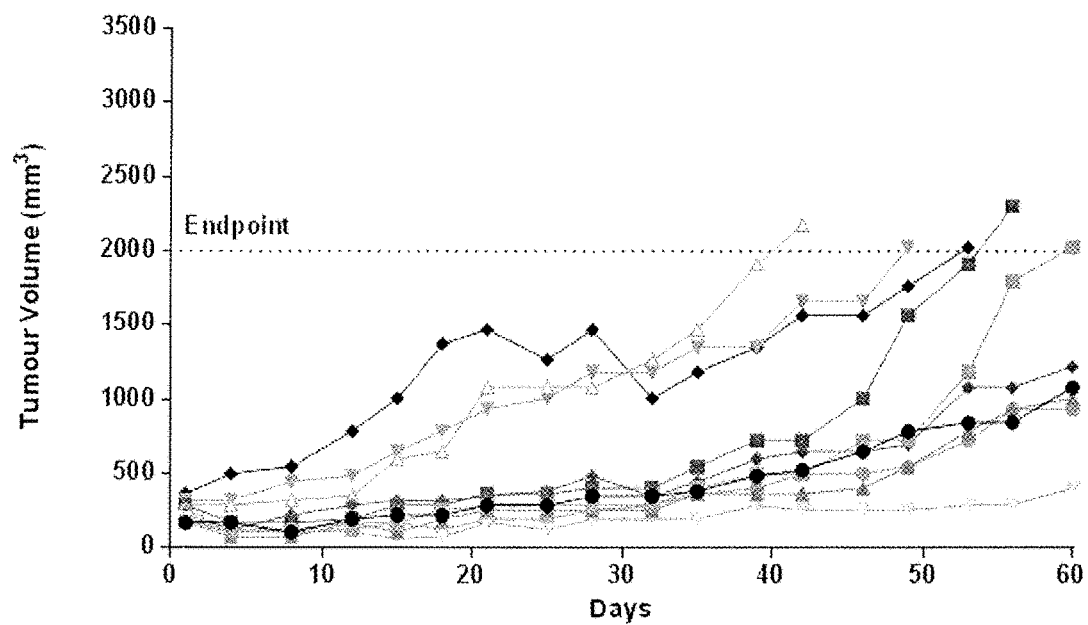
Figure 3H:
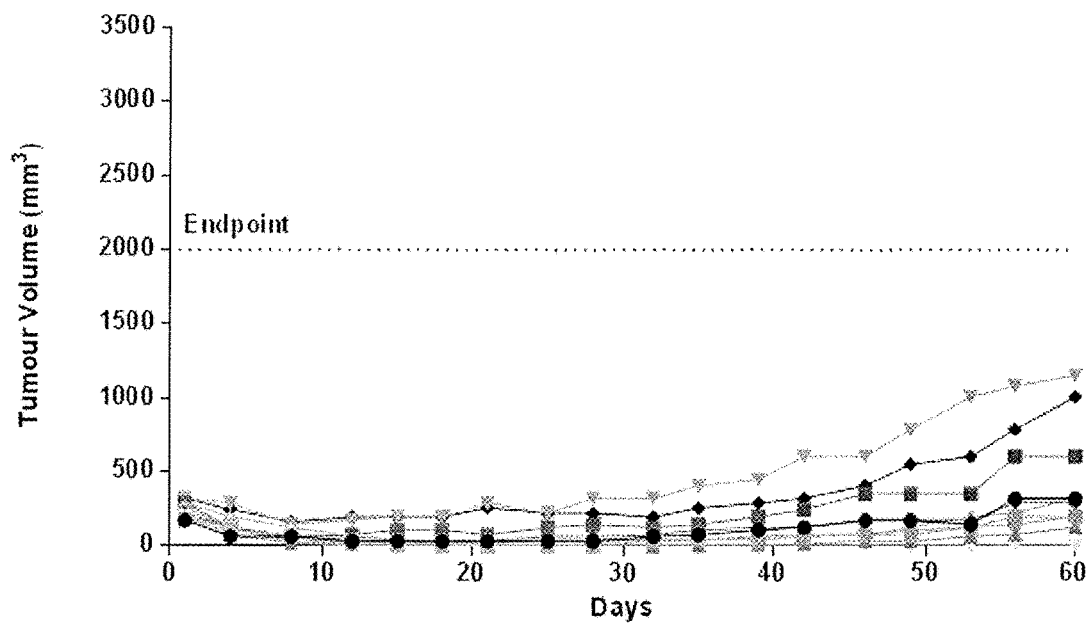
Figure 3I:
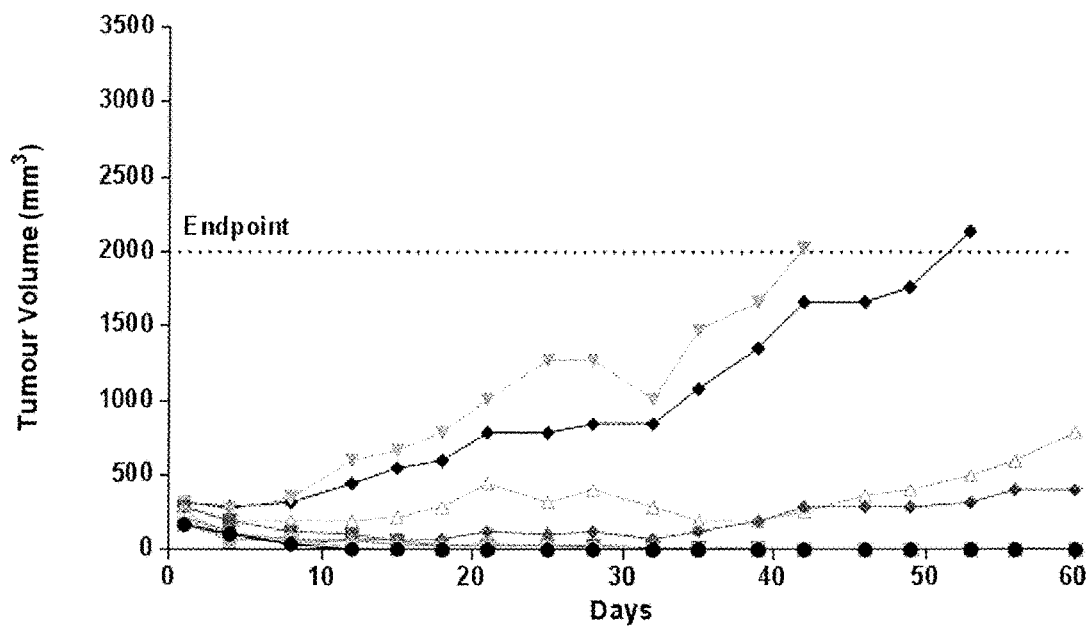
Figure 3J:
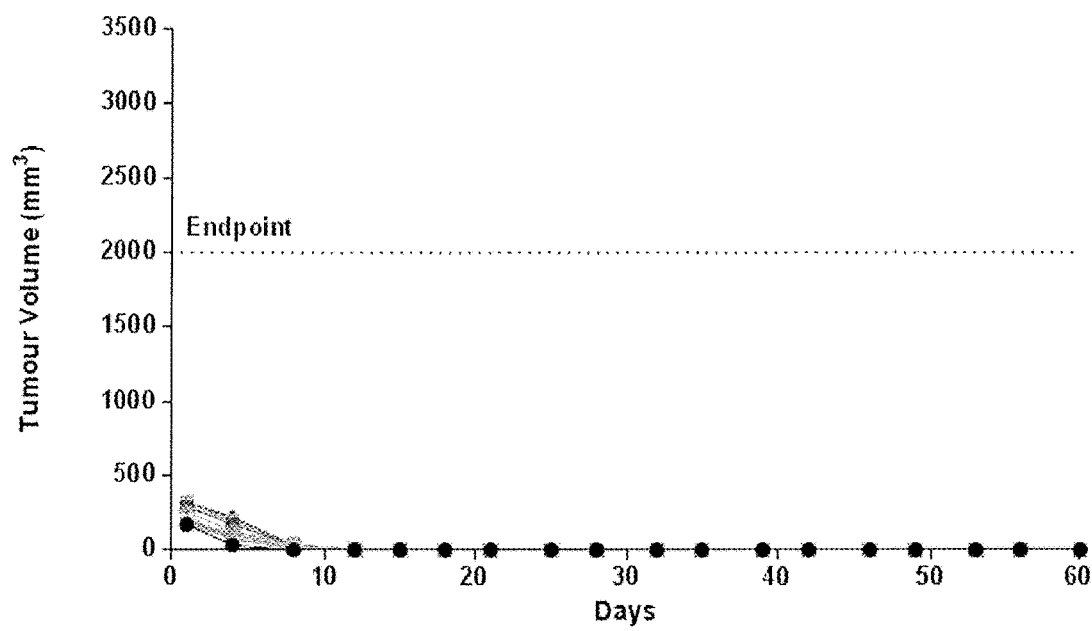

Cell Line Model of Anti-CD38 Antibody-Attenuated IFN Alpha-2b Construct+Lenalidomide Combination Therapy In these experiments, 8-12 week-old female CB.17 severe combined immunodeficient (SCID) mice were implanted with 0.2 ml of 50% MATRIGEL® matrix-containing 10 million NCI-H929 multiple myeloma cells subcutaneously in the flank. When tumors reached an average size of 200-300 mm$^3$, mice were pair matched into different groups and then treated with vehicle (PBS), free-non-attenuated interferon alpha (IFN-alpha) at 0.5 mg/kg, a suboptimal dose of an anti-CD38 antibody-IFN alpha-2b-145D construct (2.5 mg/kg, molar equivalent to 0.5 mg/kg IFN; ip, biweekly, which was determined by previous in vivo efficacy studies), an isotype-matched antibody-IFN alpha-2b-145D construct (isotype matched to the anti-CD38 antibody, with no anti-CD38 specificity), lenalidomide alone (2.5 mg/kg), a combination of free-non-attenuated interferon alpha and lenalidomide, a combination of lenalidomide and a suboptimal dose of the anti-CD38 antibody-IFN alpha-2b-145D construct, or a combination of the isotype control antibody-IFN alpha-2b-145D construct and lenalidomide. The amount of the anti-CD38 antibody-attenuated IFN alpha-2b construct administered was normalized to an IFN-alpha molar equivalent of the 0.5 mg/kg of free interferon administered to the animals. The results of these experiments are shown in FIG. 1 and FIG. 2. An animal was terminated if the tumor grew to a volume of greater than 2000 mm$^3$ before the study was completed.

FIG. 2 shows the less than synergistic effect of non-attenuated interferon alpha (free interferon, not part of a construct) and lenalidomide. The combination of interferon and lenalidomide delayed tumor growth relative to interferon or lenalidomide alone, but eventually tumor growth initiated, with rapid increase in tumor volume within about a month of commencing treatment.

In contrast, FIG. 1 shows the synergistic effect of the combination of an anti-CD38 antibody-attenuated IFN alpha-2b construct and lenalidomide. Although each of the construct, lenalidomide, and interferon alpha, when used alone, delayed tumor growth relative to the vehicle control, eventually tumor growth initiated and accelerated within two weeks to about a month. In contrast, the combination of the construct and lenalidomide demonstrated a suppression of tumor growth for the entire duration of the experiment. The effect was both significant and markedly different from the additive effects of interferon and lenalidomide such that the presence of the anti-CD38 antibody-attenuated interferon alpha-2b construct could overcome the initiation of tumor growth observed even when an isotype control antibody construct was used.

Example 2

Cell Line Model of Anti-CD38 Antibody-Attenuated Aglycosylated IFN Alpha-2b Construct+Lenalidomide Combination Therapy In this experiment, 8-12 week-old female CB.17 severe combined immunodeficient (SCID) mice were implanted with 1×10$^7$ H929 multiple myeloma tumor cells in 50% Matrigel® subcutaneously in the flank. Tumor volume was measured by calipers biweekly. When tumors reached an average size of 170-350 mm$^3$, mice were randomized and treatment commenced. An animal was terminated if the tumor grew to a volume of greater than 2000 mm$^3$ before the study was completed at day 60.

In this example, dose level and inter-dosing interval of administration of an anti-CD38 antibody fused to attenuated aglycosylated interferon-alpha 2b (A10.21 (T106A)) in combination with lenalidomide was investigated. A10.21 (T106A) is an anti-CD38 IgG4 antibody x10.21 fused to an aglycosylated attenuated IFN alpha 2b having the substitutions A145D and T106A. The treatment regimen and results are summarized in Table 5 and the data for individual animals are shown in FIG. 3A to 3J. Ten animals were assigned to each of groups 1 to 10. Treatment may cause "partial regression" (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm$^3$ for three consecutive measurements during the study. Any animal with a CR response at the end of the study was additionally classified as a tumor free survivor (TFS).

with lenalidomide or (ii) all animals treated with 1 mg/kg A10.21 (T106A) biweekly for 29 days in combination with lenalidomide. The Kaplan-Meier Survival Plot (FIG. 4) shows improved survival at Day 60 (the longest interval studied) with the combination of these compounds over lenalidomide alone. Accordingly, the combination of these compounds facilitates less frequent dosing and administration of lower dosage levels of either or both of lenalidomide and anti-CD-38-attenuated IFN alpha2b.

Example 3

Pomalidomide Study

These experiments were undertaken to determine the efficacy of the combination of a non-curative dosage regime of an anti-CD38 antibody fused to attenuated interferon-alpha 2b and a non-curative dosage regime of pomalidomide in the H929 human multiple myeloma xenograft model in female CB17 SCID mice. Pomalidomide, like lenalidomide, is a derivative and an analog of thalidomide with increased potency against multiple myeloma and reduced toxicity.

TABLE 5

Combination therapy treatment regimen and results summary.

| | Treatment 1 | | | | Treatment 2 | | | MTV (n) | | | |
|---|---|---|---|---|---|---|---|---|---|---|---|
| Group | Agent | mg/kg | Route | Schedule | Agent | mg/kg | Route | Schedule | Day 60 | PR | CR | TFS |
| 1# | Vehicle | — | ip | bi wk for 29 days | — | — | — | — | — | 0 | 0 | 0 |
| 2 | lenalidomide | 25 | ip | qd × 21 | — | — | — | — | 726 (1) | 1 | 0 | 0 |
| 3 | A10.21 (T106A) | 0.3 | ip | bi wk for 29 days | — | — | — | — | 425 (4) | 0 | 0 | 0 |
| 4 | A10.21 (T106A) | 0.3 | ip | bi wk for 29 days | lenalidomide | 25 | ip | qd × 21 | 405 (8) | 8 | 0 | 0 |
| 5 | A10.21 (T106A) | 1 | ip | bi wk for 29 days | — | — | — | — | 70 (10) | 2 | 4 | 4 |
| 6 | A10.21 (T106A) | 1 | ip | bi wk for 29 days | lenalidomide | 25 | ip | qd × 21 | 0 (10) | 1 | 9 | 9 |
| 7 | A10.21 (T106A) | 1 | ip | q4 wk for 29 days | — | — | — | — | 1008 (5) | 0 | 0 | 0 |
| 8 | A10.21 (T106A) | 1 | ip | q4 wk for 29 days | lenalidomide | 25 | ip | qd × 21 | 304 (10) | 5 | 3 | 1 |
| 9 | A10.21 (T106A) | 3 | ip | q4 wk for 29 days | — | — | — | — | 2 (8) | 1 | 6 | 5 |
| 10 | A10.21 (T106A) | 3 | ip | q4 wk for 29 days | lenalidomide | 25 | ip | qd × 21 | 0 (10) | 0 | 10 | 10 |

- Control Group (vehicle)
Study Endpoint - Earliest of 60 days or tumor volume greater than 2000 mm$^3$
MTV (n) - Median Tumor Volume at study end (number of surviving animals used for calculation)
PR—No. of Partial Regressions
CR—No. of Complete Regressions
TFS—No. of Tumor Free Survivors Table 5 and FIG. 3 show the synergistic effect of the combination of a sub-optimal dosage of an anti-CD38 antibody fused to attenuated aglycosylated interferon-alpha 2b (T106A) and lenalidomide. The combination of lenalidomide and an anti-CD38 antibody fused to an attenuated aglycosylated interferon-alpha2b allowed a reduction of the dose levels and an increase in dosing intervals of the construct which was required to effectively inhibit tumor growth. Although the construct or lenalidomide when used alone delayed tumor growth relative to vehicle control, tumor growth eventually recommenced. In contrast, the combination of the A10.21 antibody-attenuated aglycosylated IFN alpha2b (T106A) construct and lenalidomide demonstrated suppression of tumor growth for an extended period of time. Furthermore, tumor-free survival at 60 days was achieved in (i) all animals treated with 3 mg/kg A10.21 (T106A) once every 4 weeks for 29 days in combination In brief, sixty female CB.17 SCID mice were injected with 1×10$^7$ H929 tumor cells subcutaneously in the right flank. Treatment with pomalidomide and an anti-CD38 antibody fused to attenuated interferon-alpha 2b began when tumors reached an average volume of 150 mm$^3$. The endpoint for the study was when tumor volume reached 2000 mm$^3$. Cohorts were divided as follows, as summarized in Table 6: Group 1, Vehicle (PBS); Group 2, Pomalidomide alone (2.5 mg/kg); Group 3, Anti-CD38-attenuated IFNα- (40 ug/dose); Group 4, Anti-isotype-IFNα-attenuated (40 ug/dose), Group 5, Pomalidomide (2.5 mg/kg) plus anti-CD38-attenuated IFNa (40 μg/dose); and Group 6, Pomalidomide (2.5 mg/kg) plus anti-isotype-attenuated IFNα- (40 μg/dose), Pomalidomide administration started at day 1 and ended on day 21; antibody-interferon fusion construct administration started on day 1 and ended on day 28.

TABLE 6

Groups, Drugs and Treatment.

| | | Regimen 1 | | | | Regimen 2 | | | |
|---|---|---|---|---|---|---|---|---|---|
| Gr. | N | Agent | mg/kg | Route | Schedule | Agent | mg/kg | Route | Schedule |
| 1 | 10 | Vehicle (PBS) | 40* | ip | biwk × 4 | — | — | — | — |
| 2 | 10 | Pomalidomide | 2.5 | ip | qd × 21 | — | — | — | — |
| 3 | 10 | Anti CD38-attenuated IFNalpha2b (h10A2-IFN-145D) | 40* | ip | biwk × 4 | — | — | — | — |
| 4 | 10 | Isotype control (KLH-IFN-145D) | 40* | ip | biwk × 4 | — | — | — | — |
| 5 | 10 | Pomalidomide | 2.5 | ip | qd × 21 | Anti CD38-attenuated IFNalpha2b (h10A2-IFN-145D) | 40* | ip | biwk × 4 |
| 6 | 10 | Pomalidomide | 2.5 | ip | qd × 21 | Isotype control (KLH-IFN-145D) | 40* | ip | biwk × 4 |

40* = 40 μg dose/mouse, which is approximately 2 mg/kg

Figure 5:
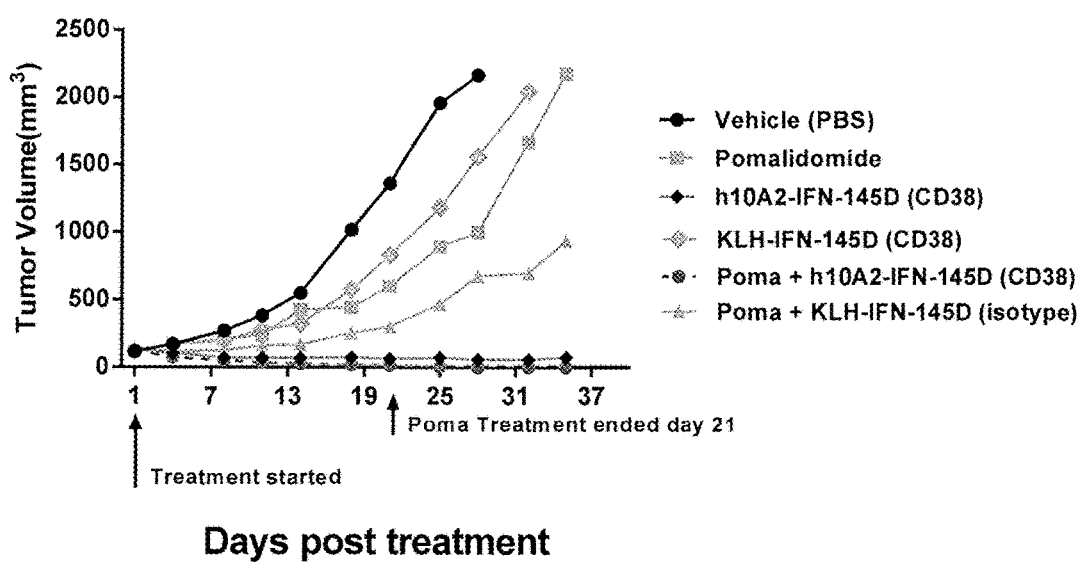
FIG. 5 shows median tumor volume in SCID mice with a multiple myeloma tumor xenograft as a function of time following treatment with either a vehicle control, a construct including an anti-CD38 antibody fused to attenuated interferon alpha 2b (145D), pomalidomide alone, a combination of interferon-alpha and pomalidomide, or a combination of the anti-CD38-attenuated interferon alpha fusion construct and pomalidomide. Treatment with the anti-CD-38-attenuated IFN alpha2b alone caused a robust shrinkage of the tumors that was stable for the duration of the study, but animals treated with the construct alone demonstrated some tumor regrowth in 7 of the 10 mice during treatment. The combination of pomalidomide with the anti-CD38-attenuated IFN alpha2b was also able to shrink tumors, but substantially fewer mice (4 out of 10 mice) demonstrated tumor regrowth during treatment.

Pomalidomide treatment alone did not substantially slow tumor growth at the dosage used. The anti-CD38-attenuated IFN alpha2b treatment alone caused a robust shrinkage of tumors for the duration of the study. Seven of 10 mice showed minimal tumor regrowth (FIG. 5). In contrast in mice treated with the combination of pomalidomide and anti-CD38-attenuated IFN alpha2b only 4 of 10 showed minimal regrowth, with 6 of 10 mice apparently having their tumors cured. Mice treated with pomalidomide and irrelevant isotype control antibody-attenuated IFN alpha2b had their tumors stabilized for a period of approximately 10 days, but then tumors started growing, albeit at a rate somewhat slower than vehicle controls.

The disclosure is not limited to the embodiments described and exemplified above, but is capable of variation and modification within the scope of the appended claims.

---

We claim:

1. A method for treating a CD38-expressing B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia, or acute lymphocytic leukemia in a subject, the method comprising administering to the subject lenalidomide or pomalidomide and an antibody that specifically binds to CD38, the antibody comprising a heavy chain variable region comprising the amino acid sequence of SEQ ID NO: 18 and a light chain variable region comprising the amino acid sequence of SEQ ID NO: 29, and the antibody being fused to an attenuated interferon alpha 2b.

2. The method according to claim 1, wherein the heavy chain variable region comprises the amino acid sequence of SEQ ID NO: 27.

3. The method according to claim 1, wherein the antibody comprises a light chain comprising a constant region.

4. The method according to claim 3, wherein the light chain comprises the amino acid sequence of SEQ ID NO: 217.

5. The method according to claim 1, wherein the antibody comprises a human IgG4 constant region.

6. The method according to claim 5, wherein the human IgG4 constant region comprises a proline at position 228 according to the EU numbering system.

7. The method according to claim 6, wherein the human IgG4 constant region further comprises a tyrosine at position 252, a threonine at position 254, and a glutamic acid at position 256 of the constant region according to the EU numbering system.

8. The method according to claim 1, wherein the antibody comprises a human IgG1 constant region.

9. The method according to claim 8, wherein the human IgG1 constant region comprises a tyrosine at position 252, a threonine at position 254, and a glutamic acid at position 256 of the constant region according to the EU numbering system.

10. The method according to claim 1, wherein the attenuated interferon alpha-2b comprises the amino acid sequence of SEQ ID NO: 3, SEQ ID NO: 5, SEQ ID NO: 6, SEQ ID NO: 7, SEQ ID NO: 212, or SEQ ID NO: 213.

11. The method according to claim 1, wherein the attenuated interferon alpha-2b comprises the amino acid sequence of SEQ ID NO: 212 or SEQ ID NO: 213.

12. The method according to claim 1, wherein the attenuated interferon alpha-2b comprises the amino acid sequence of SEQ ID NO: 212.

13. The method according to claim 1, wherein the subject has CD38-expressing multiple myeloma.

14. A method for treating a CD38-expressing B-cell lymphoma, multiple myeloma, early stage multiple myeloma, pre-multiple myeloma, Waldenström's macroglobulinemia, non-Hodgkin's lymphoma, chronic myelogenous leukemia, chronic lymphocytic leukemia, or acute lymphocytic leukemia in a subject, the method comprising administering to the subject lenalidomide or pomalidomide and an antibody that specifically binds to CD38, the antibody comprising a heavy chain variable region comprising the amino acid sequence of SEQ ID NO: 27 and a light chain variable region comprising the amino acid sequence of SEQ ID NO: 22, and the antibody being fused to an attenuated interferon alpha 2b.

15. The method according to claim 14, wherein the light chain variable region comprises the amino acid sequence of SEQ ID NO: 29.

16. The method according to claim 14, wherein the antibody comprises a light chain comprising a constant region.

17. The method according to claim 16, wherein the light chain comprises the amino acid sequence of SEQ ID NO: 217.

18. The method according to claim 14, wherein the attenuated interferon alpha-2b comprises the amino acid sequence of SEQ ID NO: 3, SEQ ID NO: 5, SEQ ID NO: 6, SEQ ID NO: 7, SEQ ID NO: 212, or SEQ ID NO: 213.

19. The method according to claim 14, wherein the attenuated interferon alpha-2b comprises the amino acid sequence of SEQ ID NO: 212 or SEQ ID NO: 213.

20. The method according to claim 14, wherein the attenuated interferon alpha-2b comprises the amino acid sequence of SEQ ID NO: 212.

21. The method according to claim 14, wherein the subject has CD38-expressing multiple myeloma.

* * * * *

UNITED STATES PATENT AND TRADEMARK OFFICE
CERTIFICATE OF CORRECTION

PATENT NO. : 10,232,041 B2
APPLICATION NO. : 15/420152
DATED : March 19, 2019
INVENTOR(S) : Sarah L. Pogue et al.

Page 1 of 1

It is certified that error appears in the above-identified patent and that said Letters Patent is hereby corrected as shown below:

On the Title Page

Item (72) please add the following inventors:
Adam CLARKE
Matthew POLLARD
Teresa DOMAGALA Signed and Sealed this
Twenty-fifth Day of June, 2019

Andrei Iancu
*Director of the United States Patent and Trademark Office*

SEQUENCE LISTING

```
<160> NUMBER OF SEQ ID NOS: 217

<210> SEQ ID NO 1
<211> LENGTH: 258
<212> TYPE: PRT
<213> ORGANISM: Homo sapiens

<400> SEQUENCE: 1

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr
    50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
    130                 135                 140
```

```
Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 2
<211> LENGTH: 258
<212> TYPE: PRT
<213> ORGANISM: Macaca fascicularis

<400> SEQUENCE: 2

Leu Pro Arg Trp Arg Gln Gln Trp Ser Gly Ser Gly Thr Thr Ser Arg
1               5                   10                  15

Phe Pro Glu Thr Val Leu Ala Arg Cys Val Lys Tyr Thr Glu Val His
                20                  25                  30

Pro Glu Met Arg His Val Asp Cys Gln Ser Val Trp Asp Ala Phe Lys
            35                  40                  45

Gly Ala Phe Ile Ser Lys Tyr Pro Cys Asn Ile Thr Glu Glu Asp Tyr
50                  55                  60

Gln Pro Leu Val Lys Leu Gly Thr Gln Thr Val Pro Cys Asn Lys Thr
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Met Leu Leu Gly Tyr Leu Ala
            100                 105                 110

Asp Asp Leu Thr Trp Cys Gly Glu Phe Asn Thr Phe Glu Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Thr Ala Cys Gly
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Ala Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Arg Phe Phe Cys Lys Asn Ile Tyr Arg Pro Asp
225                 230                 235                 240

Lys Phe Leu Gln Cys Val Lys Asn Pro Glu Asp Ser Ser Cys Leu Ser
                245                 250                 255
```

Gly Ile

<210> SEQ ID NO 3
<211> LENGTH: 188
<212> TYPE: PRT
<213> ORGANISM: Artificial Sequence
<220> FEATURE:
<223> OTHER INFORMATION: Synthesized

<400> SEQUENCE: 3

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Met Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Asp Glu Ile Met Arg Ser Phe Ser Leu
                165                 170                 175

Ser Thr Asn Leu Gln Glu Ser Leu Arg Ser Lys Glu
            180                 185

<210> SEQ ID NO 4
<211> LENGTH: 165
<212> TYPE: PRT
<213> ORGANISM: Homo sapiens

<400> SEQUENCE: 4

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Met Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

```
Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 5
<211> LENGTH: 165
<212> TYPE: PRT
<213> ORGANISM: Artificial Sequence
<220> FEATURE:
<223> OTHER INFORMATION: Synthesized

<400> SEQUENCE: 5

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Met Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Asp Glu Ile Met Arg Ser Phe Ser Leu Ser Thr Asn Leu Gln Glu Ser
145                 150                 155                 160

Leu Arg Ser Lys Glu
            165

<210> SEQ ID NO 6
<211> LENGTH: 188
<212> TYPE: PRT
<213> ORGANISM: Artificial Sequence
<220> FEATURE:
<223> OTHER INFORMATION: Synthesized

<400> SEQUENCE: 6

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Met Asp Ser Ser
```

```
                85                  90                  95
Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
            115                 120                 125

Thr Glu Thr Pro Leu Met Lys Glu Asp Ser Ile Leu Ala Val Arg Lys
            130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Gly Glu Ile Met Arg Ser Phe Ser Leu
                165                 170                 175

Ser Thr Asn Leu Gln Glu Ser Leu Arg Ser Lys Glu
            180                 185

<210> SEQ ID NO 7
<211> LENGTH: 165
<212> TYPE: PRT
<213> ORGANISM: Artificial Sequence
<220> FEATURE:
<223> OTHER INFORMATION: Synthesized

<400> SEQUENCE: 7

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Met Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
            130                 135                 140

Gly Glu Ile Met Arg Ser Phe Ser Leu Ser Thr Asn Leu Gln Glu Ser
145                 150                 155                 160

Leu Arg Ser Lys Glu
                165

<210> SEQ ID NO 8
<211> LENGTH: 188
<212> TYPE: PRT
<213> ORGANISM: Homo sapiens

<400> SEQUENCE: 8

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45
```

Leu Phe Ser Cys Leu Lys Asp Arg His Asp Phe Gly Phe Pro Gln Glu
            50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Met Asp Ser Ser
                    85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
            115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
            165                 170                 175

Ser Thr Asn Leu Gln Glu Ser Leu Arg Ser Lys Glu
            180                 185

<210> SEQ ID NO 9
<211> LENGTH: 492
<212> TYPE: PRT
<213> ORGANISM: Artificial Sequence
<220> FEATURE:
<223> OTHER INFORMATION: Synthesized

<400> SEQUENCE: 9

Ala Ser Thr Lys Gly Pro Ser Val Phe Pro Leu Ala Pro Cys Ser Arg
1                   5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
            325                 330                 335

Gly Ser Arg Arg Thr Leu Met Leu Leu Ala Gln Met Arg Arg Ile Ser
        340                 345                 350

Leu Phe Ser Cys Leu Lys Asp Arg His Asp Phe Gly Phe Pro Gln Glu
    355                 360                 365

Glu Phe Gly Asn Gln Phe Gln Lys Ala Glu Thr Ile Pro Val Leu His
370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
            405                 410                 415

Gln Gln Leu Asn Asp Leu Glu Ala Cys Val Ile Gln Gly Val Gly Val
        420                 425                 430

Thr Glu Thr Pro Leu Met Lys Glu Asp Ser Ile Leu Ala Val Arg Lys
    435                 440                 445

Tyr Phe Gln Arg Ile Thr Leu Tyr Leu Lys Glu Lys Lys Tyr Ser Pro
450                 455                 460

Cys Ala Trp Glu Val Val Arg Asp Glu Ile Met Arg Ser Phe Ser Leu
465                 470                 475                 480

Ser Thr Asn Leu Gln Glu Ser Leu Arg Ser Lys Glu
            485                 490

<210> SEQ ID NO 10
<211> LENGTH: 492
<212> TYPE: PRT
<213> ORGANISM: Artificial Sequence
<220> FEATURE:
<223> OTHER INFORMATION: Synthesized

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

-continued

```
Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
    370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

Tyr Phe Gln Arg Ile Thr Leu Tyr Leu Lys Glu Lys Lys Tyr Ser Pro
    450                 455                 460

Cys Ala Trp Glu Val Val Arg Gly Glu Ile Met Arg Ser Phe Ser Leu
465                 470                 475                 480

Ser Thr Asn Leu Gln Glu Ser Leu Arg Ser Lys Glu
                485                 490

<210> SEQ ID NO 11
<211> LENGTH: 492
```

```
<212> TYPE: PRT
<213> ORGANISM: Artificial Sequence
<220> FEATURE:
<223> OTHER INFORMATION: Synthesized

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
    370                 375                 380
```

```
Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
            405                 410                 415

Gln Gln Leu Asn Asp Leu Glu Ala Cys Val Ile Gln Gly Val Gly Val
        420                 425                 430

Thr Glu Thr Pro Leu Met Lys Glu Asp Ser Ile Leu Ala Val Arg Lys
    435                 440                 445

Tyr Phe Gln Arg Ile Thr Leu Tyr Leu Lys Glu Lys Tyr Ser Pro
450                 455                 460

Cys Ala Trp Glu Val Val Arg Gly Glu Ile Met Arg Ser Phe Ser Leu
465                 470                 475                 480

Ser Thr Asn Leu Gln Glu Ser Leu Arg Ser Lys Glu
            485                 490
```

<210> SEQ ID NO 12
<211> LENGTH: 495
<212> TYPE: PRT
<213> ORGANISM: Artificial Sequence
<220> FEATURE:
<223> OTHER INFORMATION: Synthesized

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Cys Asp Leu Pro Gln Thr
                325                 330                 335

His Ser Leu Gly Ser Arg Arg Thr Leu Met Leu Leu Ala Gln Met Arg
            340                 345                 350

Arg Ile Ser Leu Phe Ser Cys Leu Lys Asp Arg His Asp Phe Gly Phe
            355                 360                 365

Pro Gln Glu Glu Phe Gly Asn Gln Phe Gln Lys Ala Glu Thr Ile Pro
        370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
                405                 410                 415

Glu Leu Tyr Gln Gln Leu Asn Asp Leu Glu Ala Cys Val Ile Gln Gly
            420                 425                 430

Val Gly Val Thr Glu Thr Pro Leu Met Lys Glu Asp Ser Ile Leu Ala
            435                 440                 445

Val Arg Lys Tyr Phe Gln Arg Ile Thr Leu Tyr Leu Lys Glu Lys Lys
    450                 455                 460

Tyr Ser Pro Cys Ala Trp Glu Val Val Arg Gly Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 13
<211> LENGTH: 495
<212> TYPE: PRT
<213> ORGANISM: Artificial Sequence
<220> FEATURE:
<223> OTHER INFORMATION: Synthesized

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Cys Asp Leu Pro Gln Thr
                325                 330                 335

His Ser Leu Gly Ser Arg Arg Thr Leu Met Leu Leu Ala Gln Met Arg
            340                 345                 350

Arg Ile Ser Leu Phe Ser Cys Leu Lys Asp Arg His Asp Phe Gly Phe
        355                 360                 365

Pro Gln Glu Glu Phe Gly Asn Gln Phe Gln Lys Ala Glu Thr Ile Pro
370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
                405                 410                 415

Glu Leu Tyr Gln Gln Leu Asn Asp Leu Glu Ala Cys Val Ile Gln Gly
            420                 425                 430

Val Gly Val Thr Glu Thr Pro Leu Met Lys Glu Asp Ser Ile Leu Ala
        435                 440                 445

Val Arg Lys Tyr Phe Gln Arg Ile Thr Leu Tyr Leu Lys Glu Lys Lys
450                 455                 460

Tyr Ser Pro Cys Ala Trp Glu Val Val Arg Asp Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 14
<211> LENGTH: 495
<212> TYPE: PRT
<213> ORGANISM: Artificial Sequence
<220> FEATURE:
<223> OTHER INFORMATION: Synthesized

<400> SEQUENCE: 14

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Tyr Ile Thr Arg Glu Pro Glu Val Thr Cys
 130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
         195                 200                 205

Lys Ala Leu Pro Ala Pro Ile Glu Lys Thr Ile Ser Lys Ala Lys Gly
 210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
             260                 265                 270

Asn Tyr Lys Thr Thr Pro Pro Val Leu Asp Ser Asp Gly Ser Phe Phe
         275                 280                 285

Leu Tyr Ser Lys Leu Thr Val Asp Lys Ser Arg Trp Gln Gln Gly Asn
 290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Cys Asp Leu Pro Gln Thr
                 325                 330                 335

His Ser Leu Gly Ser Arg Arg Thr Leu Met Leu Leu Ala Gln Met Arg
             340                 345                 350

Arg Ile Ser Leu Phe Ser Cys Leu Lys Asp Arg His Asp Phe Gly Phe
         355                 360                 365

Pro Gln Glu Glu Phe Gly Asn Gln Phe Gln Lys Ala Glu Thr Ile Pro
 370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
                 405                 410                 415

Glu Leu Tyr Gln Gln Leu Asn Asp Leu Glu Ala Cys Val Ile Gln Gly
```

```
                420                 425                 430
Val Gly Val Thr Glu Thr Pro Leu Met Lys Glu Asp Ser Ile Leu Ala
            435                 440                 445

Val Arg Lys Tyr Phe Gln Arg Ile Thr Leu Tyr Leu Lys Glu Lys Lys
        450                 455                 460

Tyr Ser Pro Cys Ala Trp Glu Val Val Arg Gly Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 15
<211> LENGTH: 492
<212> TYPE: PRT
<213> ORGANISM: Artificial Sequence
<220> FEATURE:
<223> OTHER INFORMATION: Synthesized

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

```
                290                 295                 300
Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335

Gly Ser Arg Arg Thr Leu Met Leu Leu Ala Gln Met Arg Arg Ile Ser
                340                 345                 350

Leu Phe Ser Cys Leu Lys Asp Arg His Asp Phe Gly Phe Pro Gln Glu
                355                 360                 365

Glu Phe Gly Asn Gln Phe Gln Lys Ala Glu Thr Ile Pro Val Leu His
                370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
                420                 425                 430

Thr Glu Thr Pro Leu Met Lys Glu Asp Ser Ile Leu Ala Val Arg Lys
                435                 440                 445

Tyr Phe Gln Arg Ile Thr Leu Tyr Leu Lys Glu Lys Lys Tyr Ser Pro
                450                 455                 460

Cys Ala Trp Glu Val Val Arg Asp Glu Ile Met Arg Ser Phe Ser Leu
465                 470                 475                 480

Ser Thr Asn Leu Gln Glu Ser Leu Arg Ser Lys Glu
                485                 490

<210> SEQ ID NO 16
<211> LENGTH: 492
<212> TYPE: PRT
<213> ORGANISM: Artificial Sequence
<220> FEATURE:
<223> OTHER INFORMATION: Synthesized

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Tyr Ile Thr Arg Glu Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
            325                 330                 335

Gly Ser Arg Arg Thr Leu Met Leu Leu Ala Gln Met Arg Arg Ile Ser
        340                 345                 350

Leu Phe Ser Cys Leu Lys Asp Arg His Asp Phe Gly Phe Pro Gln Glu
    355                 360                 365

Glu Phe Gly Asn Gln Phe Gln Lys Ala Glu Thr Ile Pro Val Leu His
370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
            405                 410                 415

Gln Gln Leu Asn Asp Leu Glu Ala Cys Val Ile Gln Gly Val Gly Val
        420                 425                 430

Thr Glu Thr Pro Leu Met Lys Glu Asp Ser Ile Leu Ala Val Arg Lys
    435                 440                 445

Tyr Phe Gln Arg Ile Thr Leu Tyr Leu Lys Glu Lys Lys Tyr Ser Pro
450                 455                 460

Cys Ala Trp Glu Val Val Arg Gly Glu Ile Met Arg Ser Phe Ser Leu
465                 470                 475                 480

Ser Thr Asn Leu Gln Glu Ser Leu Arg Ser Lys Glu
            485                 490

```
<210> SEQ ID NO 17
<211> LENGTH: 121
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (42)..(42)
<223> OTHER INFORMATION: Xaa = His or Pro
<220> FEATURE:
<221> NAME/KEY: VARIANT
<222> LOCATION: (76)..(76)
<223> OTHER INFORMATION: Xaa = Ser or Leu
<220> FEATURE:
<221> NAME/KEY: VARIANT
```

<222> LOCATION: (80)..(80)
<223> OTHER INFORMATION: Xaa = Phe or Ile
<220> FEATURE:
<221> NAME/KEY: VARIANT
<222> LOCATION: (83)..(83)
<223> OTHER INFORMATION: Xaa = Lys or Arg
<220> FEATURE:
<221> NAME/KEY: VARIANT
<222> LOCATION: (85)..(85)
<223> OTHER INFORMATION: Xaa = Ser or Thr
<220> FEATURE:
<221> NAME/KEY: VARIANT
<222> LOCATION: (108)..(108)
<223> OTHER INFORMATION: Xaa = Leu or Met

<400> SEQUENCE: 17

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln Xaa Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Xaa Lys Asn Gln Xaa
65                  70                  75                  80

Ser Leu Xaa Leu Xaa Ser Val Thr Ala Ala Asp Thr Ala Val Tyr Tyr
                85                  90                  95

Cys Ala Arg Val Gly Gly Ala Gly Gly Trp Pro Xaa Asp Val Trp Gly
            100                 105                 110

Gln Gly Thr Thr Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (1)..(1)
<223> OTHER INFORMATION: Xaa = Glu or Gln
<220> FEATURE:
<221> NAME/KEY: VARIANT
<222> LOCATION: (17)..(17)
<223> OTHER INFORMATION: Xaa = Thr or Ser
<220> FEATURE:
<221> NAME/KEY: VARIANT
<222> LOCATION: (20)..(20)
<223> OTHER INFORMATION: Xaa = Ile or Val
<220> FEATURE:
<221> NAME/KEY: VARIANT
<222> LOCATION: (29)..(29)
<223> OTHER INFORMATION: Xaa = Phe or Leu
<220> FEATURE:
<221> NAME/KEY: VARIANT
<222> LOCATION: (38)..(38)
<223> OTHER INFORMATION: Xaa = Gln or Arg
<220> FEATURE:
<221> NAME/KEY: VARIANT
<222> LOCATION: (40)..(40)
<223> OTHER INFORMATION: Xaa = Glu or Gly or His or Ala
<220> FEATURE:
<221> NAME/KEY: VARIANT
<222> LOCATION: (62)..(62)
<223> OTHER INFORMATION: Xaa = Glu or Gln
<220> FEATURE:
<221> NAME/KEY: VARIANT
<222> LOCATION: (70)..(70)

```
<223> OTHER INFORMATION: Xaa = Ile or Met
<220> FEATURE:
<221> NAME/KEY: VARIANT
<222> LOCATION: (100)..(100)
<223> OTHER INFORMATION: Xaa = Lys or Gly or Thr
<220> FEATURE:
<221> NAME/KEY: VARIANT
<222> LOCATION: (102)..(102)
<223> OTHER INFORMATION: Xaa = Asn or Gln

<400> SEQUENCE: 18

Xaa Val Gln Leu Val Gln Ser Gly Ala Glu Val Lys Lys Pro Gly Ala
1               5                  10                  15

Xaa Val Lys Xaa Ser Cys Lys Val Ser Gly Tyr Thr Xaa Thr Asp Ser
            20                  25                  30

Val Met Asn Trp Val Xaa Gln Xaa Pro Gly Lys Gly Leu Glu Trp Met
        35                  40                  45

Gly Trp Ile Asp Pro Glu Tyr Gly Arg Thr Asp Val Ala Xaa Lys Phe
    50                  55                  60

Gln Gly Arg Val Thr Xaa Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Xaa Tyr Xaa Ser Gly Tyr Gly Phe Pro Tyr Trp Gly Gln
                100                 105                 110

Gly Thr Thr Val Thr Val Ser Ser
            115                 120

<210> SEQ ID NO 19
<211> LENGTH: 122
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (40)..(40)
<223> OTHER INFORMATION: Xaa = Ala or Pro
<220> FEATURE:
<221> NAME/KEY: VARIANT
<222> LOCATION: (58)..(58)
<223> OTHER INFORMATION: Xaa = Val or Thr
<220> FEATURE:
<221> NAME/KEY: VARIANT
<222> LOCATION: (95)..(95)
<223> OTHER INFORMATION: Xaa = Phe or Tyr
<220> FEATURE:
<221> NAME/KEY: VARIANT
<222> LOCATION: (102)..(102)
<223> OTHER INFORMATION: Xaa = Met or Leu

<400> SEQUENCE: 19

Glu Val Gln Leu Val Gln Ser Gly Ala Glu Val Lys Lys Ser Gly Ala
1               5                  10                  15

Ser Val Lys Val Ser Cys Lys Ala Ser Gly Tyr Thr Phe Thr Asp Tyr
            20                  25                  30

Tyr Ile His Trp Val Arg Gln Xaa Pro Gly Gln Gly Leu Glu Trp Met
        35                  40                  45

Gly Trp Ile Asn Pro Asn Asn Gly Gly Xaa Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Asp Thr Ala Val Tyr Xaa Cys
                85                  90                  95
```

-continued

```
Ala Arg Asp Ile Arg Xaa Ser Gly Trp Leu Ala Pro Phe Asp Tyr Trp
            100                 105                 110

Gly Gln Gly Thr Leu Val Thr Val Ser Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (17)..(17)
<223> OTHER INFORMATION: Xaa = S or T
<220> FEATURE:
<221> NAME/KEY: VARIANT
<222> LOCATION: (20)..(20)
<223> OTHER INFORMATION: Xaa = I or V
<220> FEATURE:
<221> NAME/KEY: VARIANT
<222> LOCATION: (29)..(29)
<223> OTHER INFORMATION: Xaa = F or L
<220> FEATURE:
<221> NAME/KEY: VARIANT
<222> LOCATION: (38)..(38)
<223> OTHER INFORMATION: Xaa = R or Q
<220> FEATURE:
<221> NAME/KEY: VARIANT
<222> LOCATION: (40)..(40)
<223> OTHER INFORMATION: Xaa = A or H
<220> FEATURE:
<221> NAME/KEY: VARIANT
<222> LOCATION: (70)..(70)
<223> OTHER INFORMATION: Xaa = I or M

<400> SEQUENCE: 20

Glu Val Gln Leu Val Gln Ser Gly Ala Glu Val Lys Lys Pro Gly Ala
1               5                   10                  15

Xaa Val Lys Xaa Ser Cys Lys Val Ser Gly Tyr Thr Xaa Thr Asp Ser
            20                  25                  30

Val Met Asn Trp Val Xaa Gln Xaa Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Xaa Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 21
<211> LENGTH: 117
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (31)..(31)
<223> OTHER INFORMATION: Xaa = Arg or Gly
<220> FEATURE:
<221> NAME/KEY: VARIANT
<222> LOCATION: (32)..(32)
```

```
<223> OTHER INFORMATION: Xaa = Tyr or Ser
<220> FEATURE:
<221> NAME/KEY: VARIANT
<222> LOCATION: (54)..(54)
<223> OTHER INFORMATION: Xaa = Ser or Glu or Gln
<220> FEATURE:
<221> NAME/KEY: VARIANT
<222> LOCATION: (77)..(77)
<223> OTHER INFORMATION: Xaa = Asn or Thr
<220> FEATURE:
<221> NAME/KEY: VARIANT
<222> LOCATION: (97)..(97)
<223> OTHER INFORMATION: Xaa = Met or Leu
<220> FEATURE:
<221> NAME/KEY: VARIANT
<222> LOCATION: (102)..(102)
<223> OTHER INFORMATION: Xaa = Asn or Gln or Glu

<400> SEQUENCE: 21

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Xaa Xaa
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Xaa Asp Ser His Lys Gly Gln Gly Ser Gly Val
    50                  55                  60

Pro Ser Arg Phe Ser Gly Ser Lys Asp Val Ser Thr Xaa Ser Gly Ile
65                  70                  75                  80

Leu Leu Ile Ser Gly Leu Gln Ser Glu Asp Ile Ala Thr Tyr Tyr Cys
                85                  90                  95

Xaa Thr Trp Ser Ser Xaa Gly Ser Gly Val Phe Gly Gly Gly Thr Gln
                100                 105                 110

Leu Thr Val Leu Gly
            115

<210> SEQ ID NO 22
<211> LENGTH: 108
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (24)..(24)
<223> OTHER INFORMATION: Xaa = Lys or Gly or Gln
<220> FEATURE:
<221> NAME/KEY: VARIANT
<222> LOCATION: (53)..(53)
<223> OTHER INFORMATION: Xaa = Asn or Gln
<220> FEATURE:
<221> NAME/KEY: VARIANT
<222> LOCATION: (54)..(54)
<223> OTHER INFORMATION: Xaa = Arg or Asp
<220> FEATURE:
<221> NAME/KEY: VARIANT
<222> LOCATION: (89)..(89)
<223> OTHER INFORMATION: Xaa = Met or Ala

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45
```

Tyr Lys Ala Ser Xaa Xaa Tyr Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Xaa Gln Ser Asn Thr His Pro Arg
                85                  90                  95

Thr Phe Gly Gly Gly Thr Lys Val Glu Ile Lys Arg
                100                 105

<210> SEQ ID NO 23
<211> LENGTH: 108
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (24)..(24)
<223> OTHER INFORMATION: Xaa = K or Q
<220> FEATURE:
<221> NAME/KEY: VARIANT
<222> LOCATION: (89)..(89)
<223> OTHER INFORMATION: Xaa = A or M

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asn Val Asp Ser Asp
            20                  25                  30

Val Asp Trp Tyr Gln Gly Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Xaa Gln Ser Asn Thr His Pro Arg
                85                  90                  95

Thr Phe Gly Gly Gly Thr Lys Val Glu Ile Lys Arg
                100                 105

<210> SEQ ID NO 24
<211> LENGTH: 121
<212> TYPE: PRT
<213> ORGANISM: Homo sapiens

<400> SEQUENCE: 24

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

-continued

Gln Gly Thr Thr Val Thr Val Ser Ser
        115                 120

<210> SEQ ID NO 25
<211> LENGTH: 117
<212> TYPE: PRT
<213> ORGANISM: Homo sapiens

<400> SEQUENCE: 25

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 26
<211> LENGTH: 120
<212> TYPE: PRT
<213> ORGANISM: Artificial Sequence
<220> FEATURE:
<223> OTHER INFORMATION: Synthesized

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: Synthesized

<400> SEQUENCE: 27

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 28
<211> LENGTH: 120
<212> TYPE: PRT
<213> ORGANISM: Artificial Sequence
<220> FEATURE:
<223> OTHER INFORMATION: Synthesized

<400> SEQUENCE: 28

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln His Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 29
<211> LENGTH: 108
<212> TYPE: PRT
<213> ORGANISM: Artificial Sequence
<220> FEATURE:
<223> OTHER INFORMATION: Synthesized

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
```

```
                50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Met Gln Ser Asn Thr His Pro Arg
                 85                  90                  95

Thr Phe Gly Gly Gly Thr Lys Val Glu Ile Lys Arg
                100                 105

<210> SEQ ID NO 30
<211> LENGTH: 108
<212> TYPE: PRT
<213> ORGANISM: Artificial Sequence
<220> FEATURE:
<223> OTHER INFORMATION: Synthesized

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asn Val Asp Ser Asp
                 20                  25                  30

Val Asp Trp Tyr Gln Gln Lys Pro Gly Lys Ala Pro Lys Leu Leu Ile
             35                  40                  45

Tyr Lys Ala Ser Asn Asp Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Ala Gln Ser Asn Thr His Pro Arg
                 85                  90                  95

Thr Phe Gly Gly Gly Thr Lys Val Glu Ile Lys Arg
                100                 105

<210> SEQ ID NO 31
<211> LENGTH: 121
<212> TYPE: PRT
<213> ORGANISM: Artificial Sequence
<220> FEATURE:
<223> OTHER INFORMATION: Synthesized

<400> SEQUENCE: 31

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                 20                  25                  30

Ser Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Leu Lys Asn Gln Ile
 65                  70                  75                  80

Ser Leu Arg Leu Thr Ser Val Thr Ala Ala Asp Thr Ala Val Tyr Tyr
                 85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 32
<211> LENGTH: 121
```

```
<212> TYPE: PRT
<213> ORGANISM: Artificial Sequence
<220> FEATURE:
<223> OTHER INFORMATION: Synthesized

<400> SEQUENCE: 32

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Arg Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 33
<211> LENGTH: 121
<212> TYPE: PRT
<213> ORGANISM: Artificial Sequence
<220> FEATURE:
<223> OTHER INFORMATION: Synthesized

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 34
<211> LENGTH: 121
<212> TYPE: PRT
<213> ORGANISM: Artificial Sequence
<220> FEATURE:
<223> OTHER INFORMATION: Synthesized

<400> SEQUENCE: 34

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
```

```
                    20                  25                  30
Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Leu Lys Asn Gln Ile
65                  70                  75                  80

Ser Leu Arg Leu Thr Ser Val Arg Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 35
<211> LENGTH: 121
<212> TYPE: PRT
<213> ORGANISM: Artificial Sequence
<220> FEATURE:
<223> OTHER INFORMATION: Synthesized

<400> SEQUENCE: 35

Gln Leu Gln Leu Gln Glu Ser Gly Pro Gly Leu Val Lys Pro Ser Glu
1               5                   10                  15

Thr Leu Lys Leu Thr Cys Thr Val Ser Gly Gly Ser Ile Ser Ser Ser
                20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 36
<211> LENGTH: 121
<212> TYPE: PRT
<213> ORGANISM: Artificial Sequence
<220> FEATURE:
<223> OTHER INFORMATION: Synthesized

<400> SEQUENCE: 36

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Leu Lys Asn Gln Ile
65                  70                  75                  80
```

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Leu Glu Val Trp Gly
            100                 105                 110

Gln Gly Thr Thr Val Thr Val Ser Ser
        115                 120

<210> SEQ ID NO 37
<211> LENGTH: 121
<212> TYPE: PRT
<213> ORGANISM: Artificial Sequence
<220> FEATURE:
<223> OTHER INFORMATION: Synthesized

<400> SEQUENCE: 37

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Lys Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 38
<211> LENGTH: 121
<212> TYPE: PRT
<213> ORGANISM: Artificial Sequence
<220> FEATURE:
<223> OTHER INFORMATION: Synthesized

<400> SEQUENCE: 38

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Leu Asp Val Trp Gly
            100                 105                 110

Gln Gly Thr Thr Val Thr Val Ser Ser
        115                 120

<210> SEQ ID NO 39

<211> LENGTH: 120
<212> TYPE: PRT
<213> ORGANISM: Artificial Sequence
<220> FEATURE:
<223> OTHER INFORMATION: Synthesized

<400> SEQUENCE: 39

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Glu Val Trp Gly
            100                 105                 110

Gln Gly Thr Thr Val Thr Val Ser
        115                 120

<210> SEQ ID NO 40
<211> LENGTH: 121
<212> TYPE: PRT
<213> ORGANISM: Artificial Sequence
<220> FEATURE:
<223> OTHER INFORMATION: Synthesized

<400> SEQUENCE: 40

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 41
<211> LENGTH: 121
<212> TYPE: PRT
<213> ORGANISM: Artificial Sequence
<220> FEATURE:
<223> OTHER INFORMATION: Synthesized

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 42
<211> LENGTH: 121
<212> TYPE: PRT
<213> ORGANISM: Artificial Sequence
<220> FEATURE:
<223> OTHER INFORMATION: Synthesized

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Lys Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 43
<211> LENGTH: 121
<212> TYPE: PRT
<213> ORGANISM: Artificial Sequence
<220> FEATURE:
<223> OTHER INFORMATION: Synthesized

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

```
Ser Leu Lys Leu Ser Ser Val Thr Ala Ala Asp Thr Ala Val Tyr Tyr
                85                  90                  95

Cys Ala Arg Val Gly Gly Ala Gly Gly Trp Pro Leu Asp Val Trp Gly
            100                 105                 110

Gln Gly Thr Thr Val Thr Val Ser Ser
        115                 120

<210> SEQ ID NO 44
<211> LENGTH: 121
<212> TYPE: PRT
<213> ORGANISM: Artificial Sequence
<220> FEATURE:
<223> OTHER INFORMATION: Synthesized

<400> SEQUENCE: 44

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly Gly Ala Gly Gly Trp Pro Leu Asp Val Trp Gly
            100                 105                 110

Gln Gly Thr Thr Val Thr Val Ser Ser
        115                 120

<210> SEQ ID NO 45
<211> LENGTH: 122
<212> TYPE: PRT
<213> ORGANISM: Artificial Sequence
<220> FEATURE:
<223> OTHER INFORMATION: Synthesized

<400> SEQUENCE: 45

Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Pro Pro Gly Gln Gly Leu Glu Trp Met
        35                  40                  45

Gly Trp Ile Asn Pro Asn Asn Gly Gly Val Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Asp Thr Ala Val Tyr Phe Cys
                85                  90                  95

Ala Arg Asp Ile Arg Met Ser Gly Trp Leu Ala Pro Phe Asp Tyr Trp
            100                 105                 110

Gly Gln Gly Thr Leu Val Thr Val Ser Ser
        115                 120
```

<210> SEQ ID NO 46
<211> LENGTH: 122
<212> TYPE: PRT
<213> ORGANISM: Artificial Sequence
<220> FEATURE:
<223> OTHER INFORMATION: Synthesized

<400> SEQUENCE: 46

```
Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Pro Pro Gly Gln Gly Leu Glu Trp Met
        35                  40                  45

Gly Trp Ile Asn Pro Asn Asn Gly Gly Val Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Thr Ala Val Tyr Tyr Cys
                85                  90                  95

Ala Arg Asp Ile Arg Met Ser Gly Trp Leu Ala Pro Phe Asp Tyr Trp
            100                 105                 110

Gly Gln Gly Thr Leu Val Thr Val Ser Ser
        115                 120
```

<210> SEQ ID NO 47
<211> LENGTH: 122
<212> TYPE: PRT
<213> ORGANISM: Artificial Sequence
<220> FEATURE:
<223> OTHER INFORMATION: Synthesized

<400> SEQUENCE: 47

```
Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Pro Pro Gly Gln Gly Leu Glu Trp Met
        35                  40                  45

Gly Trp Ile Asn Pro Asn Asn Gly Gly Thr Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Thr Ala Val Tyr Phe Cys
                85                  90                  95

Ala Arg Asp Ile Arg Met Ser Gly Trp Leu Ala Pro Phe Asp Tyr Trp
            100                 105                 110

Gly Gln Gly Thr Leu Val Thr Val Ser Ser
        115                 120
```

<210> SEQ ID NO 48
<211> LENGTH: 122
<212> TYPE: PRT
<213> ORGANISM: Artificial Sequence
<220> FEATURE:
<223> OTHER INFORMATION: Synthesized

<400> SEQUENCE: 48

```
Glu Val Gln Leu Val Gln Ser Gly Ala Glu Val Lys Lys Ser Gly Ala
1               5                   10                  15
```

-continued

```
Ser Val Lys Val Ser Cys Lys Ala Ser Gly Tyr Thr Phe Thr Asp Tyr
            20                  25                  30

Tyr Ile His Trp Val Arg Gln Pro Gly Gln Gly Leu Glu Trp Met
        35                  40                  45

Gly Trp Ile Asn Pro Asn Asn Gly Gly Val Thr Phe Ala Gln Lys Phe
 50                  55                  60

Gln Gly Arg Val Thr Met Thr Arg Asp Thr Ser Ile Ser Thr Ala Tyr
 65                  70                  75                  80

Met Asp Leu Ser Ser Leu Arg Ser Asp Thr Ala Val Tyr Phe Cys
            85                  90                  95

Ala Arg Asp Ile Arg Leu Ser Gly Trp Leu Ala Pro Phe Asp Tyr Trp
            100                 105                 110

Gly Gln Gly Thr Leu Val Thr Val Ser Ser
            115                 120
```

<210> SEQ ID NO 49
<211> LENGTH: 117
<212> TYPE: PRT
<213> ORGANISM: Homo sapiens

<400> SEQUENCE: 49

```
Gln Ala Val Leu Thr Gln Pro Ala Ser Leu Ser Ala Ser Pro Gly Glu
 1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Glu Ala Asp Tyr Tyr Cys
            85                  90                  95

Met Thr Trp Ser Ser Asn Gly Ser Gly Val Phe Gly Gly Gly Thr Gln
            100                 105                 110

Leu Thr Val Leu Gly
            115
```

<210> SEQ ID NO 50
<211> LENGTH: 117
<212> TYPE: PRT
<213> ORGANISM: Artificial Sequence
<220> FEATURE:
<223> OTHER INFORMATION: Synthesized

<400> SEQUENCE: 50

```
Gln Ala Val Leu Thr Gln Pro Ala Ser Leu Ser Ala Ser Pro Gly Glu
 1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80
```

Leu Leu Ile Ser Gly Leu Gln Ser Glu Asp Glu Ala Asp Tyr Tyr Cys
            85                  90                  95

Met Thr Trp Ser Ser Gln Gly Ser Gly Val Phe Gly Gly Gly Thr Gln
            100                 105                 110

Leu Thr Val Leu Gly
        115

<210> SEQ ID NO 51
<211> LENGTH: 117
<212> TYPE: PRT
<213> ORGANISM: Artificial Sequence
<220> FEATURE:
<223> OTHER INFORMATION: Synthesized

<400> SEQUENCE: 51

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Ala Ser Gly Ile
65                  70                  75                  80

Leu Leu Ile Ser Gly Leu Gln Ser Glu Asp Glu Ala Asp Tyr Tyr Cys
            85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 52
<211> LENGTH: 117
<212> TYPE: PRT
<213> ORGANISM: Artificial Sequence
<220> FEATURE:
<223> OTHER INFORMATION: Synthesized

<400> SEQUENCE: 52

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Arg Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
            85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 53

```
<211> LENGTH: 117
<212> TYPE: PRT
<213> ORGANISM: Artificial Sequence
<220> FEATURE:
<223> OTHER INFORMATION: Synthesized

<400> SEQUENCE: 53

Gln Ala Val Leu Thr Gln Pro Ala Ser Leu Ser Ala Ser Pro Gly Ala
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 54
<211> LENGTH: 117
<212> TYPE: PRT
<213> ORGANISM: Artificial Sequence
<220> FEATURE:
<223> OTHER INFORMATION: Synthesized

<400> SEQUENCE: 54

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Arg Tyr Arg Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 55
<211> LENGTH: 115
<212> TYPE: PRT
<213> ORGANISM: Artificial Sequence
<220> FEATURE:
<223> OTHER INFORMATION: Synthesized

<400> SEQUENCE: 55

Gln Ala Val Leu Thr Gln Pro Ala Ser Leu Ser Ala Ser Pro Gly Glu
1               5                   10                  15
```

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Ser Thr Asn Ser Gly Ile Leu Leu
65                  70                  75                  80

Ile Ser Gly Leu Gln Ser Glu Asp Glu Ala Asp Tyr Tyr Cys Met Thr
                85                  90                  95

Trp Ser Ser Asn Gly Ser Gly Val Phe Gly Gly Gly Thr Gln Leu Thr
                100                 105                 110

Val Leu Gly
        115

<210> SEQ ID NO 56
<211> LENGTH: 117
<212> TYPE: PRT
<213> ORGANISM: Artificial Sequence
<220> FEATURE:
<223> OTHER INFORMATION: Synthesized

<400> SEQUENCE: 56

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Gly Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115

<210> SEQ ID NO 57
<211> LENGTH: 117
<212> TYPE: PRT
<213> ORGANISM: Artificial Sequence
<220> FEATURE:
<223> OTHER INFORMATION: Synthesized

<400> SEQUENCE: 57

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

```
Leu Leu Ile Ser Gly Leu Gln Ser Glu Asp Glu Ala Asp Tyr Tyr Cys
                85                  90                  95

Met Thr Trp Ser Ser Asn Gly Ala Gly Val Phe Gly Gly Gly Thr Gln
            100                 105                 110

Leu Thr Val Leu Gly
        115

<210> SEQ ID NO 58
<211> LENGTH: 117
<212> TYPE: PRT
<213> ORGANISM: Artificial Sequence
<220> FEATURE:
<223> OTHER INFORMATION: Synthesized

<400> SEQUENCE: 58

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Arg Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 59
<211> LENGTH: 117
<212> TYPE: PRT
<213> ORGANISM: Artificial Sequence
<220> FEATURE:
<223> OTHER INFORMATION: Synthesized

<400> SEQUENCE: 59

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Arg Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115
```

<210> SEQ ID NO 60
<211> LENGTH: 117
<212> TYPE: PRT
<213> ORGANISM: Artificial Sequence
<220> FEATURE:
<223> OTHER INFORMATION: Synthesized

<400> SEQUENCE: 60

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Thr Gly Ser Gly Val Phe Gly Gly Gly Thr Gln
            100                 105                 110

Leu Thr Val Leu Gly
        115
```

<210> SEQ ID NO 61
<211> LENGTH: 117
<212> TYPE: PRT
<213> ORGANISM: Artificial Sequence
<220> FEATURE:
<223> OTHER INFORMATION: Synthesized

<400> SEQUENCE: 61

```
Gln Ala Val Leu Thr Gln Pro Ala Ser Leu Ser Ala Ser Pro Gly Glu
1               5                   10                  15

Ser Ala Arg Leu Thr Cys Thr Leu Arg Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115
```

<210> SEQ ID NO 62
<211> LENGTH: 117
<212> TYPE: PRT
<213> ORGANISM: Artificial Sequence
<220> FEATURE:
<223> OTHER INFORMATION: Synthesized

<400> SEQUENCE: 62

```
Gln Ala Val Leu Thr Gln Pro Ala Ser Leu Ser Ala Ser Pro Gly Glu
1               5                   10                  15
```

```
Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Pro Ser Gly Val Phe Gly Gly Gly Thr Gln
            100                 105                 110

Leu Thr Val Leu Gly
        115

<210> SEQ ID NO 63
<211> LENGTH: 117
<212> TYPE: PRT
<213> ORGANISM: Artificial Sequence
<220> FEATURE:
<223> OTHER INFORMATION: Synthesized

<400> SEQUENCE: 63

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Ile Thr Trp Ser Ser Asn Gly Ser Gly Val Phe Gly Gly Gly Thr Gln
            100                 105                 110

Leu Thr Val Leu Gly
        115

<210> SEQ ID NO 64
<211> LENGTH: 117
<212> TYPE: PRT
<213> ORGANISM: Artificial Sequence
<220> FEATURE:
<223> OTHER INFORMATION: Synthesized

<400> SEQUENCE: 64

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
```

```
                65                  70                  75                  80
Leu Leu Ile Ser Gly Leu Gln Ser Glu Asp Glu Ala Asp Tyr Tyr Cys
                85                  90                  95

Leu Thr Trp Ser Ser Asn Gly Ser Gly Val Phe Gly Gly Gly Thr Gln
                100                 105                 110

Leu Thr Val Leu Gly
            115

<210> SEQ ID NO 65
<211> LENGTH: 117
<212> TYPE: PRT
<213> ORGANISM: Artificial Sequence
<220> FEATURE:
<223> OTHER INFORMATION: Synthesized

<400> SEQUENCE: 65

Gln Pro Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Ser Asp Ser His Lys Gly Gln Gly Ser Gly Val
            50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115

<210> SEQ ID NO 66
<211> LENGTH: 117
<212> TYPE: PRT
<213> ORGANISM: Artificial Sequence
<220> FEATURE:
<223> OTHER INFORMATION: Synthesized

<400> SEQUENCE: 66

Gln Ala Val Leu Thr Gln Pro Pro Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Ser Asp Ser His Lys Gly Gln Gly Ser Gly Val
            50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115
```

<210> SEQ ID NO 67
<211> LENGTH: 117
<212> TYPE: PRT
<213> ORGANISM: Artificial Sequence
<220> FEATURE:
<223> OTHER INFORMATION: Synthesized

<400> SEQUENCE: 67

Gln Ala Val Leu Thr Gln Pro Ala Ser Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 68
<211> LENGTH: 117
<212> TYPE: PRT
<213> ORGANISM: Artificial Sequence
<220> FEATURE:
<223> OTHER INFORMATION: Synthesized

<400> SEQUENCE: 68

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 69
<211> LENGTH: 117
<212> TYPE: PRT
<213> ORGANISM: Artificial Sequence
<220> FEATURE:
<223> OTHER INFORMATION: Synthesized

<400> SEQUENCE: 69

Gln Ala Val Leu Thr Gln Pro Ala Ser Leu Ser Ala Ser Pro Gly Glu

```
1               5                   10                  15
Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115
```

<210> SEQ ID NO 70
<211> LENGTH: 117
<212> TYPE: PRT
<213> ORGANISM: Artificial Sequence
<220> FEATURE:
<223> OTHER INFORMATION: Synthesized

<400> SEQUENCE: 70

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser Asp Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115
```

<210> SEQ ID NO 71
<211> LENGTH: 117
<212> TYPE: PRT
<213> ORGANISM: Artificial Sequence
<220> FEATURE:
<223> OTHER INFORMATION: Synthesized

<400> SEQUENCE: 71

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60
```

Pro Ser Arg Phe Ser Gly Ser Lys Asp Ala Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115

<210> SEQ ID NO 72
<211> LENGTH: 117
<212> TYPE: PRT
<213> ORGANISM: Artificial Sequence
<220> FEATURE:
<223> OTHER INFORMATION: Synthesized

<400> SEQUENCE: 72

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Ala Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115

<210> SEQ ID NO 73
<211> LENGTH: 117
<212> TYPE: PRT
<213> ORGANISM: Artificial Sequence
<220> FEATURE:
<223> OTHER INFORMATION: Synthesized

<400> SEQUENCE: 73

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Thr Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115

<210> SEQ ID NO 74
<211> LENGTH: 117
<212> TYPE: PRT
<213> ORGANISM: Artificial Sequence
<220> FEATURE:
<223> OTHER INFORMATION: Synthesized

<400> SEQUENCE: 74

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Ile Trp Ser Ser Asn Gly Ser Gly Val Phe Gly Gly Gly Thr Gln
            100                 105                 110

Leu Thr Val Leu Gly
        115
```

<210> SEQ ID NO 75
<211> LENGTH: 117
<212> TYPE: PRT
<213> ORGANISM: Artificial Sequence
<220> FEATURE:
<223> OTHER INFORMATION: Synthesized

<400> SEQUENCE: 75

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Pro Ser Asn Gly Ser Gly Val Phe Gly Gly Gly Thr Gln
            100                 105                 110

Leu Thr Val Leu Gly
        115
```

<210> SEQ ID NO 76
<211> LENGTH: 117
<212> TYPE: PRT
<213> ORGANISM: Artificial Sequence
<220> FEATURE:
<223> OTHER INFORMATION: Synthesized

<400> SEQUENCE: 76

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Ala Ser Gly Val Phe Gly Gly Gly Thr Gln
            100                 105                 110

Leu Thr Val Leu Gly
        115

<210> SEQ ID NO 77
<211> LENGTH: 117
<212> TYPE: PRT
<213> ORGANISM: Artificial Sequence
<220> FEATURE:
<223> OTHER INFORMATION: Synthesized

<400> SEQUENCE: 77

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 78
<211> LENGTH: 117
<212> TYPE: PRT
<213> ORGANISM: Artificial Sequence
<220> FEATURE:
<223> OTHER INFORMATION: Synthesized

<400> SEQUENCE: 78

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
    50                  55                  60

```
Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Leu Thr Trp Ser Ser Asn Gly Ser Gly Val Phe Gly Gly Gly Thr Gln
             100                 105                 110

Leu Thr Val Leu Gly
        115

<210> SEQ ID NO 79
<211> LENGTH: 117
<212> TYPE: PRT
<213> ORGANISM: Artificial Sequence
<220> FEATURE:
<223> OTHER INFORMATION: Synthesized

<400> SEQUENCE: 79

Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
             35                  40                  45

Leu Leu Tyr Tyr Tyr Ser Asp Ser His Lys Gly Gln Gly Ser Gly Val
         50                  55                  60

Pro Ser Arg Phe Ser Gly Ser Lys Asp Val Ser Thr Gln Ser Gly Ile
 65                  70                  75                  80

Leu Leu Ile Ser Gly Leu Gln Ser Glu Asp Ile Ala Thr Tyr Tyr Cys
                 85                  90                  95

Met Thr Trp Ser Ser Asn Gly Ser Gly Val Phe Gly Gly Gly Thr Gln
             100                 105                 110

Leu Thr Val Leu Gly
        115

<210> SEQ ID NO 80
<211> LENGTH: 117
<212> TYPE: PRT
<213> ORGANISM: Artificial Sequence
<220> FEATURE:
<223> OTHER INFORMATION: Synthesized

<400> SEQUENCE: 80

Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
             35                  40                  45

Leu Leu Tyr Tyr Tyr Ser Asp Ser His Lys Gly Gln Gly Ser Gly Val
         50                  55                  60

Pro Ser Arg Phe Ser Gly Ser Lys Asp Val Ser Thr Thr Ser Gly Ile
 65                  70                  75                  80

Leu Leu Ile Ser Gly Leu Gln Ser Glu Asp Ile Ala Thr Tyr Tyr Cys
                 85                  90                  95

Met Thr Trp Ser Ser Asn Gly Ser Gly Val Phe Gly Gly Gly Thr Gln
             100                 105                 110

Leu Thr Val Leu Gly
```

<210> SEQ ID NO 81
<211> LENGTH: 117
<212> TYPE: PRT
<213> ORGANISM: Artificial Sequence
<220> FEATURE:
<223> OTHER INFORMATION: Synthesized

<400> SEQUENCE: 81

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Gly Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 82
<211> LENGTH: 117
<212> TYPE: PRT
<213> ORGANISM: Artificial Sequence
<220> FEATURE:
<223> OTHER INFORMATION: Synthesized

<400> SEQUENCE: 82

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr His Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 83
<211> LENGTH: 117
<212> TYPE: PRT
<213> ORGANISM: Artificial Sequence
<220> FEATURE:
<223> OTHER INFORMATION: Synthesized

<400> SEQUENCE: 83

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Lys Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115

<210> SEQ ID NO 84
<211> LENGTH: 117
<212> TYPE: PRT
<213> ORGANISM: Artificial Sequence
<220> FEATURE:
<223> OTHER INFORMATION: Synthesized

<400> SEQUENCE: 84

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Pro Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115

<210> SEQ ID NO 85
<211> LENGTH: 117
<212> TYPE: PRT
<213> ORGANISM: Artificial Sequence
<220> FEATURE:
<223> OTHER INFORMATION: Synthesized

<400> SEQUENCE: 85

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Glu Leu Tyr Tyr Tyr Ser Asp Ser His Lys Gly Gln Gly Ser Gly Val

```
                    50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                    85                  90                  95

Met Thr Trp Ser Ser Asn Gly Ser Gly Val Phe Gly Gly Gly Thr Gln
                   100                 105                 110

Leu Thr Val Leu Gly
            115
```

<210> SEQ ID NO 86
<211> LENGTH: 117
<212> TYPE: PRT
<213> ORGANISM: Artificial Sequence
<220> FEATURE:
<223> OTHER INFORMATION: Synthesized

<400> SEQUENCE: 86

```
Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
                 35                  40                  45

Gly Leu Tyr Tyr Tyr Ser Asp Ser His Lys Gly Gln Gly Ser Gly Val
             50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                    85                  90                  95

Met Thr Trp Ser Ser Asn Gly Ser Gly Val Phe Gly Gly Gly Thr Gln
                   100                 105                 110

Leu Thr Val Leu Gly
            115
```

<210> SEQ ID NO 87
<211> LENGTH: 117
<212> TYPE: PRT
<213> ORGANISM: Artificial Sequence
<220> FEATURE:
<223> OTHER INFORMATION: Synthesized

<400> SEQUENCE: 87

```
Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
                 35                  40                  45

Asn Leu Tyr Tyr Tyr Ser Asp Ser His Lys Gly Gln Gly Ser Gly Val
             50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                    85                  90                  95

Met Thr Trp Ser Ser Asn Gly Ser Gly Val Phe Gly Gly Gly Thr Gln
                   100                 105                 110
```

Leu Thr Val Leu Gly
        115

<210> SEQ ID NO 88
<211> LENGTH: 117
<212> TYPE: PRT
<213> ORGANISM: Artificial Sequence
<220> FEATURE:
<223> OTHER INFORMATION: Synthesized

<400> SEQUENCE: 88

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Pro Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 89
<211> LENGTH: 117
<212> TYPE: PRT
<213> ORGANISM: Artificial Sequence
<220> FEATURE:
<223> OTHER INFORMATION: Synthesized

<400> SEQUENCE: 89

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Ser Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 90
<211> LENGTH: 117
<212> TYPE: PRT
<213> ORGANISM: Artificial Sequence
<220> FEATURE:
<223> OTHER INFORMATION: Synthesized

```
<400> SEQUENCE: 90

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Glu Tyr Tyr Ser Asp Ser His Lys Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 91
<211> LENGTH: 117
<212> TYPE: PRT
<213> ORGANISM: Artificial Sequence
<220> FEATURE:
<223> OTHER INFORMATION: Synthesized

<400> SEQUENCE: 91

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Pro Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 92
<211> LENGTH: 117
<212> TYPE: PRT
<213> ORGANISM: Artificial Sequence
<220> FEATURE:
<223> OTHER INFORMATION: Synthesized

<400> SEQUENCE: 92

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45
```

```
Leu Leu Glu Tyr Tyr Ser Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Met Thr Trp Ser Ser Asn Gly Ser Gly Val Phe Gly Gly Gly Thr Gln
                100                 105                 110

Leu Thr Val Leu Gly
        115
```

<210> SEQ ID NO 93
<211> LENGTH: 117
<212> TYPE: PRT
<213> ORGANISM: Artificial Sequence
<220> FEATURE:
<223> OTHER INFORMATION: Synthesized

<400> SEQUENCE: 93

```
Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
             35                  40                  45

Leu Leu Gln Tyr Tyr Ser Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Met Thr Trp Ser Ser Asn Gly Ser Gly Val Phe Gly Gly Gly Thr Gln
                100                 105                 110

Leu Thr Val Leu Gly
        115
```

<210> SEQ ID NO 94
<211> LENGTH: 117
<212> TYPE: PRT
<213> ORGANISM: Artificial Sequence
<220> FEATURE:
<223> OTHER INFORMATION: Synthesized

<400> SEQUENCE: 94

```
Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
             35                  40                  45

Leu Leu Tyr Pro Tyr Ser Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Met Thr Trp Ser Ser Asn Gly Ser Gly Val Phe Gly Gly Gly Thr Gln
                100                 105                 110
```

```
Leu Thr Val Leu Gly
        115

<210> SEQ ID NO 95
<211> LENGTH: 117
<212> TYPE: PRT
<213> ORGANISM: Artificial Sequence
<220> FEATURE:
<223> OTHER INFORMATION: Synthesized

<400> SEQUENCE: 95

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Asn Tyr Ser Asp Ser His Lys Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 96
<211> LENGTH: 117
<212> TYPE: PRT
<213> ORGANISM: Artificial Sequence
<220> FEATURE:
<223> OTHER INFORMATION: Synthesized

<400> SEQUENCE: 96

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Thr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 97
<211> LENGTH: 117
<212> TYPE: PRT
<213> ORGANISM: Artificial Sequence
<220> FEATURE:
<223> OTHER INFORMATION: Synthesized
```

<400> SEQUENCE: 97

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Asp Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 98
<211> LENGTH: 117
<212> TYPE: PRT
<213> ORGANISM: Artificial Sequence
<220> FEATURE:
<223> OTHER INFORMATION: Synthesized

<400> SEQUENCE: 98

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 99
<211> LENGTH: 117
<212> TYPE: PRT
<213> ORGANISM: Artificial Sequence
<220> FEATURE:
<223> OTHER INFORMATION: Synthesized

<400> SEQUENCE: 99

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr His Asp Ser His Lys Gly Gln Gly Ser Gly Val
            50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
               100                 105                 110

Leu Thr Val Leu Gly
        115

<210> SEQ ID NO 100
<211> LENGTH: 117
<212> TYPE: PRT
<213> ORGANISM: Artificial Sequence
<220> FEATURE:
<223> OTHER INFORMATION: Synthesized

<400> SEQUENCE: 100

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Gln Asp Ser His Lys Gly Gln Gly Ser Gly Val
            50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
               100                 105                 110

Leu Thr Val Leu Gly
        115

<210> SEQ ID NO 101
<211> LENGTH: 117
<212> TYPE: PRT
<213> ORGANISM: Artificial Sequence
<220> FEATURE:
<223> OTHER INFORMATION: Synthesized

<400> SEQUENCE: 101

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Ser Asp Ser Asn Lys Gly Gln Gly Ser Gly Val
            50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln

-continued

Leu Thr Val Leu Gly
        115

<210> SEQ ID NO 102
<211> LENGTH: 117
<212> TYPE: PRT
<213> ORGANISM: Artificial Sequence
<220> FEATURE:
<223> OTHER INFORMATION: Synthesized

<400> SEQUENCE: 102

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Pro Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 103
<211> LENGTH: 117
<212> TYPE: PRT
<213> ORGANISM: Artificial Sequence
<220> FEATURE:
<223> OTHER INFORMATION: Synthesized

<400> SEQUENCE: 103

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Asp Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 104
<211> LENGTH: 117
<212> TYPE: PRT
<213> ORGANISM: Artificial Sequence
<220> FEATURE:

<223> OTHER INFORMATION: Synthesized

<400> SEQUENCE: 104

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
            115

<210> SEQ ID NO 105
<211> LENGTH: 117
<212> TYPE: PRT
<213> ORGANISM: Artificial Sequence
<220> FEATURE:
<223> OTHER INFORMATION: Synthesized

<400> SEQUENCE: 105

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
            115

<210> SEQ ID NO 106
<211> LENGTH: 117
<212> TYPE: PRT
<213> ORGANISM: Artificial Sequence
<220> FEATURE:
<223> OTHER INFORMATION: Synthesized

<400> SEQUENCE: 106

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr

```
                    35                  40                  45

Leu Leu Tyr Tyr Tyr Gln Asp Ser His Lys Gly Gln Gly Ser Gly Val
         50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 107
<211> LENGTH: 117
<212> TYPE: PRT
<213> ORGANISM: Artificial Sequence
<220> FEATURE:
<223> OTHER INFORMATION: Synthesized

<400> SEQUENCE: 107

Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Arg Ser
             20                  25                  30

Tyr Asn Ile Tyr Trp Tyr Gln Gln Lys Pro Gly Ser Pro Pro Arg Tyr
             35                  40                  45

Leu Leu Tyr Tyr Tyr Gln Asp Ser His Lys Gly Gln Gly Ser Gly Val
         50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 108
<211> LENGTH: 117
<212> TYPE: PRT
<213> ORGANISM: Artificial Sequence
<220> FEATURE:
<223> OTHER INFORMATION: Synthesized

<400> SEQUENCE: 108

Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Gly Ser
             20                  25                  30

Tyr Asn Ile Tyr Trp Tyr Gln Gln Lys Pro Gly Ser Pro Pro Arg Tyr
             35                  40                  45

Leu Leu Tyr Tyr Tyr Gln Asp Ser His Lys Gly Gln Gly Ser Gly Val
         50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95
```

Leu Thr Trp Ser Ser Gln Gly Ser Gly Val Phe Gly Gly Thr Gln
                100                 105                 110

Leu Thr Val Leu Gly
        115

<210> SEQ ID NO 109
<211> LENGTH: 117
<212> TYPE: PRT
<213> ORGANISM: Artificial Sequence
<220> FEATURE:
<223> OTHER INFORMATION: Synthesized

<400> SEQUENCE: 109

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Thr Gln
                100                 105                 110

Leu Thr Val Leu Gly
        115

<210> SEQ ID NO 110
<211> LENGTH: 117
<212> TYPE: PRT
<213> ORGANISM: Artificial Sequence
<220> FEATURE:
<223> OTHER INFORMATION: Synthesized

<400> SEQUENCE: 110

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Thr Gln
                100                 105                 110

Leu Thr Val Leu Gly
        115

<210> SEQ ID NO 111
<211> LENGTH: 116
<212> TYPE: PRT
<213> ORGANISM: Artificial Sequence
<220> FEATURE:
<223> OTHER INFORMATION: Synthesized

<400> SEQUENCE: 111

Ala Val Leu Thr Gln Pro Ala Ser Leu Ser Ala Ser Pro Gly Glu Ser
1               5                   10                  15

Ala Arg Leu Thr Cys Thr Leu Pro Ser Asp Ile Asn Val Arg Ser Tyr
            20                  25                  30

Asn Ile Tyr Trp Tyr Gln Gln Lys Pro Gly Ser Pro Pro Arg Tyr Leu
        35                  40                  45

Leu Tyr Tyr Tyr Glu Asp Ser His Lys Gly Gln Gly Ser Gly Val Pro
    50                  55                  60

Ser Arg Phe Ser Gly Ser Lys Asp Val Ser Thr Asn Ser Gly Ile Leu
65                  70                  75                  80

Leu Ile Ser Gly Leu Gln Ser Glu Asp Ile Ala Thr Tyr Tyr Cys Leu
                85                  90                  95

Thr Trp Ser Ser Glu Gly Ser Gly Val Phe Gly Gly Gly Thr Gln Leu
            100                 105                 110

Thr Val Leu Gly
        115

<210> SEQ ID NO 112
<211> LENGTH: 117
<212> TYPE: PRT
<213> ORGANISM: Artificial Sequence
<220> FEATURE:
<223> OTHER INFORMATION: Synthesized

<400> SEQUENCE: 112

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 113
<211> LENGTH: 117
<212> TYPE: PRT
<213> ORGANISM: Artificial Sequence
<220> FEATURE:
<223> OTHER INFORMATION: Synthesized

<400> SEQUENCE: 113

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

```
Tyr Asn Ile Tyr Trp Tyr Gln Gln Lys Pro Gly Ser Pro Pro Arg Tyr
            35                  40                  45

Leu Leu Tyr Tyr Tyr Glu Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Leu Thr Trp Ser Ser Gln Gly Ser Gly Val Phe Gly Gly Gly Thr Gln
                100                 105                 110

Leu Thr Val Leu Gly
            115

<210> SEQ ID NO 114
<211> LENGTH: 117
<212> TYPE: PRT
<213> ORGANISM: Artificial Sequence
<220> FEATURE:
<223> OTHER INFORMATION: Synthesized

<400> SEQUENCE: 114

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Gly Ser
                 20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
 50                  55                  60

Pro Ser Arg Phe Ser Gly Ser Lys Asp Val Ser Thr Gln Ser Gly Ile
 65                  70                  75                  80

Leu Leu Ile Ser Gly Leu Gln Ser Glu Asp Ile Ala Thr Tyr Tyr Cys
                 85                  90                  95

Leu Thr Trp Ser Ser Glu Gly Ser Gly Val Phe Gly Gly Gly Thr Gln
                100                 105                 110

Leu Thr Val Leu Gly
            115

<210> SEQ ID NO 115
<211> LENGTH: 117
<212> TYPE: PRT
<213> ORGANISM: Artificial Sequence
<220> FEATURE:
<223> OTHER INFORMATION: Synthesized

<400> SEQUENCE: 115

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Ser
                 20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
 50                  55                  60

Pro Ser Arg Phe Ser Gly Ser Lys Asp Val Ser Thr Gln Ser Gly Ile
 65                  70                  75                  80

Leu Leu Ile Ser Gly Leu Gln Ser Glu Asp Ile Ala Thr Tyr Tyr Cys
                 85                  90                  95
```

```
Leu Thr Trp Ser Ser Glu Gly Ser Gly Val Phe Gly Gly Gly Thr Gln
                100                 105                 110

Leu Thr Val Leu Gly
        115

<210> SEQ ID NO 116
<211> LENGTH: 117
<212> TYPE: PRT
<213> ORGANISM: Artificial Sequence
<220> FEATURE:
<223> OTHER INFORMATION: Synthesized

<400> SEQUENCE: 116

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
                100                 105                 110

Leu Thr Val Leu Gly
        115

<210> SEQ ID NO 117
<211> LENGTH: 117
<212> TYPE: PRT
<213> ORGANISM: Artificial Sequence
<220> FEATURE:
<223> OTHER INFORMATION: Synthesized

<400> SEQUENCE: 117

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
                100                 105                 110

Leu Thr Val Leu Gly
        115

<210> SEQ ID NO 118
<211> LENGTH: 117
<212> TYPE: PRT
```

<213> ORGANISM: Artificial Sequence
<220> FEATURE:
<223> OTHER INFORMATION: Synthesized

<400> SEQUENCE: 118

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 119
<211> LENGTH: 117
<212> TYPE: PRT
<213> ORGANISM: Artificial Sequence
<220> FEATURE:
<223> OTHER INFORMATION: Synthesized

<400> SEQUENCE: 119

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 120
<211> LENGTH: 117
<212> TYPE: PRT
<213> ORGANISM: Artificial Sequence
<220> FEATURE:
<223> OTHER INFORMATION: Synthesized

<400> SEQUENCE: 120

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

```
Tyr Asn Ile Tyr Trp Tyr Gln Gln Lys Pro Gly Ser Pro Pro Arg Tyr
            35                  40                  45

Leu Leu Tyr Tyr Tyr Glu Asp Ser His Lys Gly Gln Gly Ser Gly Val
 50                      55                  60

Pro Ser Arg Phe Ser Gly Ser Lys Asp Val Ser Thr Gln Ser Gly Ile
 65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
                100                 105                 110

Leu Thr Val Leu Gly
            115

<210> SEQ ID NO 121
<211> LENGTH: 117
<212> TYPE: PRT
<213> ORGANISM: Artificial Sequence
<220> FEATURE:
<223> OTHER INFORMATION: Synthesized

<400> SEQUENCE: 121

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Glu Asp Ser His Lys Gly Gln Gly Ser Gly Val
 50                      55                  60

Pro Ser Arg Phe Ser Gly Ser Lys Asp Val Ser Thr Gln Ser Gly Ile
 65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
                100                 105                 110

Leu Thr Val Leu Gly
            115

<210> SEQ ID NO 122
<211> LENGTH: 117
<212> TYPE: PRT
<213> ORGANISM: Homo sapiens

<400> SEQUENCE: 122

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Asp Gln Gly Ser Gly Val
 50                      55                  60

Pro Ser Arg Phe Ser Gly Ser Lys Asp Thr Ser Ala Asn Thr Gly Ile
 65                  70                  75                  80

Leu Leu Ile Ser Gly Leu Gln Ser Glu Asp Glu Ala Asp Tyr Tyr Cys
                85                  90                  95
```

```
Met Ile Trp Ala Ser Asn Gly Ser Gly Val Leu Gly Gly Thr Gln
            100                 105                 110
Leu Thr Val Leu Gly
        115

<210> SEQ ID NO 123
<211> LENGTH: 117
<212> TYPE: PRT
<213> ORGANISM: Homo sapiens

<400> SEQUENCE: 123

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

His Asn Ile Tyr Trp Tyr Gln Glu Lys Pro Gly Ser Pro Pro Arg Tyr
        35                  40                  45

Leu Leu Tyr Tyr Tyr Ser Asp Ser Ser Lys Gln Gly Ser Gly Val
    50                  55                  60

Pro Ser Arg Phe Ser Gly Ser Lys Asp Val Ser Thr Asn Thr Gly Ile
65                  70                  75                  80

Leu Val Ile Ser Gly Leu Gln Ser Glu Asp Glu Ala Glu Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 124
<211> LENGTH: 117
<212> TYPE: PRT
<213> ORGANISM: Artificial Sequence
<220> FEATURE:
<223> OTHER INFORMATION: Synthesized

<400> SEQUENCE: 124

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 125
<211> LENGTH: 117
<212> TYPE: PRT
<213> ORGANISM: Artificial Sequence
<220> FEATURE:
<223> OTHER INFORMATION: Synthesized
```

<400> SEQUENCE: 125

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 126
<211> LENGTH: 117
<212> TYPE: PRT
<213> ORGANISM: Artificial Sequence
<220> FEATURE:
<223> OTHER INFORMATION: Synthesized

<400> SEQUENCE: 126

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 127
<211> LENGTH: 117
<212> TYPE: PRT
<213> ORGANISM: Artificial Sequence
<220> FEATURE:
<223> OTHER INFORMATION: Synthesized

<400> SEQUENCE: 127

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

```
Leu Leu Tyr Tyr Tyr Gln Asp Ser His Lys Gly Gln Gly Ser Gly Val
            50                  55                  60

Pro Ser Arg Phe Ser Gly Ser Lys Asp Val Ser Thr Thr Ser Gly Ile
 65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
               100                 105                 110

Leu Thr Val Leu Gly
            115

<210> SEQ ID NO 128
<211> LENGTH: 117
<212> TYPE: PRT
<213> ORGANISM: Artificial Sequence
<220> FEATURE:
<223> OTHER INFORMATION: Synthesized

<400> SEQUENCE: 128

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
            50                  55                  60

Pro Ser Arg Phe Ser Gly Ser Lys Asp Val Ser Thr Thr Ser Gly Ile
 65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
               100                 105                 110

Leu Thr Val Leu Gly
            115

<210> SEQ ID NO 129
<211> LENGTH: 117
<212> TYPE: PRT
<213> ORGANISM: Artificial Sequence
<220> FEATURE:
<223> OTHER INFORMATION: Synthesized

<400> SEQUENCE: 129

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
            50                  55                  60

Pro Ser Arg Phe Ser Gly Ser Lys Asp Val Ser Thr Thr Ser Gly Ile
 65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
```

Leu Thr Val Leu Gly
        115

<210> SEQ ID NO 130
<211> LENGTH: 122
<212> TYPE: PRT
<213> ORGANISM: Homo sapiens

<400> SEQUENCE: 130

Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Asn Gly Val Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Asp Thr Ala Val Tyr Phe Cys
                85                  90                  95

Ala Arg Asp Ile Arg Met Ser Gly Trp Leu Ala Pro Phe Asp Tyr Trp
            100                 105                 110

Gly Gln Gly Thr Leu Val Thr Val Ser Ser
        115                 120

<210> SEQ ID NO 131
<211> LENGTH: 120
<212> TYPE: PRT
<213> ORGANISM: Homo sapiens

<400> SEQUENCE: 131

Gln Val Gln Leu Val Glu Ser Gly Gly Val Val Gln Gly Gly Gly
1               5                   10                  15

Ser Leu Arg Leu Ser Cys Ala Ala Ser Gly Phe Thr Val Arg Ser Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Val Thr Thr Gly Trp Tyr Phe Asp Leu Trp Gly Arg
            100                 105                 110

Gly Thr Leu Val Thr Val Ser Ser
        115                 120

<210> SEQ ID NO 132
<211> LENGTH: 120
<212> TYPE: PRT
<213> ORGANISM: Rattus norvegicus

<400> SEQUENCE: 132

Glu Val Gln Leu Gln Gln Ser Gly Pro Glu Val Gly Arg Pro Gly Ser
1               5                   10                  15

```
Ser Val Lys Ile Ser Cys Lys Ala Ser Gly Tyr Thr Phe Thr Asp Ser
            20                  25                  30

Val Met Asn Trp Val Lys Gln Ser Pro Gly Gln Gly Leu Glu Trp Ile
        35                  40                  45

Gly Trp Ile Asp Pro Glu Tyr Gly Arg Thr Asp Val Ala Glu Lys Phe
    50                  55                  60

Lys Lys Lys Ala Thr Leu Thr Ala Asp Ser Ser Ser Thr Ala Tyr
65                  70                  75                  80

Ile Tyr Leu Ser Gly Leu Thr Ser Glu Asp Thr Ala Thr Tyr Phe Cys
                85                  90                  95

Ala Arg Thr Lys Tyr Asn Ser Gly Tyr Gly Phe Pro Tyr Trp Gly Gln
                100                 105                 110

Gly Ser Leu Val Thr Val Ser Ser
            115                 120

<210> SEQ ID NO 133
<211> LENGTH: 120
<212> TYPE: PRT
<213> ORGANISM: Artificial Sequence
<220> FEATURE:
<223> OTHER INFORMATION: Synthesized

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Lys Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 134
<211> LENGTH: 120
<212> TYPE: PRT
<213> ORGANISM: Artificial Sequence
<220> FEATURE:
<223> OTHER INFORMATION: Synthesized

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
```

Met Glu Leu Ser Ser Leu Arg Ser Glu Asp Thr Ala Val Tyr Tyr Cys
            85                  90                  95

Ala Thr Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 135
<211> LENGTH: 120
<212> TYPE: PRT
<213> ORGANISM: Artificial Sequence
<220> FEATURE:
<223> OTHER INFORMATION: Synthesized

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
            35                  40                  45

Gly Trp Ile Asp Pro Glu Tyr Gly Arg Thr Asp Val Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 136
<211> LENGTH: 120
<212> TYPE: PRT
<213> ORGANISM: Artificial Sequence
<220> FEATURE:
<223> OTHER INFORMATION: Synthesized

<400> SEQUENCE: 136

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Ser
            20                  25                  30

Val Met Asn Trp Val Arg Gln Ala Pro Gly Gln Ala Leu Glu Trp Met
            35                  40                  45

Gly Trp Ile Asp Pro Glu Tyr Gly Arg Thr Asp Val Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
            85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 137
<211> LENGTH: 120
<212> TYPE: PRT
<213> ORGANISM: Artificial Sequence
<220> FEATURE:
<223> OTHER INFORMATION: Synthesized

<400> SEQUENCE: 137

```
Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Ser
            20                  25                  30

Val Met Asn Trp Val Arg Gln Ala Pro Gly Gln Ala Leu Glu Trp Met
        35                  40                  45

Gly Trp Ile Asp Pro Glu Tyr Gly Arg Thr Asp Val Ala Gln Lys Phe
    50                  55                  60

Gln Asp Arg Val Thr Ile Thr Ala Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120
```

<210> SEQ ID NO 138
<211> LENGTH: 120
<212> TYPE: PRT
<213> ORGANISM: Artificial Sequence
<220> FEATURE:
<223> OTHER INFORMATION: Synthesized

<400> SEQUENCE: 138

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Lys Tyr Asn Ser Gly Tyr Gly Phe Pro Tyr Trp Gly Gln
            100                 105                 110

Gly Thr Thr Val Thr Val Ser Ser
        115                 120
```

<210> SEQ ID NO 139
<211> LENGTH: 120
<212> TYPE: PRT
<213> ORGANISM: Artificial Sequence
<220> FEATURE:
<223> OTHER INFORMATION: Synthesized

<400> SEQUENCE: 139

Glu Val Gln Leu Val Gln Ser Gly Ala Glu Val Lys Lys Pro Gly Ala

```
                1               5                   10                  15
            Thr Val Lys Ile Ser Cys Lys Val Ser Gly Tyr Thr Phe Thr Asp Ser
                            20                  25                  30

Val Met Asn Trp Val Gln Gln Glu Pro Gly Lys Gly Leu Glu Trp Met
                        35                  40                  45

Gly Trp Ile Asp Pro Glu Tyr Gly Arg Thr Asp Val Ala Glu Lys Phe
                    50                  55                  60

Gln Gly Arg Val Thr Ile Thr Ala Asp Thr Ser Thr Asp Thr Ala Tyr
            65                  70                  75                  80

Met Glu Leu Ser Ser Leu Arg Ser Glu Asp Thr Ala Val Tyr Tyr Cys
                            85                  90                  95

Ala Arg Thr Lys Tyr Asn Ser Gly Tyr Gly Phe Pro Tyr Trp Gly Gln
                            100                 105                 110

Gly Thr Thr Val Thr Val Ser Ser
                            115                 120

<210> SEQ ID NO 140
<211> LENGTH: 120
<212> TYPE: PRT
<213> ORGANISM: Artificial Sequence
<220> FEATURE:
<223> OTHER INFORMATION: Synthesized

<400> SEQUENCE: 140

Glu Val Gln Leu Val Gln Ser Gly Ala Glu Val Lys Lys Pro Gly Ala
            1               5                   10                  15

Thr Val Lys Ile Ser Cys Lys Val Ser Gly Tyr Thr Phe Thr Asp Ser
                            20                  25                  30

Val Met Asn Trp Val Gln Gln Gly Pro Gly Lys Gly Leu Glu Trp Met
                        35                  40                  45

Gly Trp Ile Asp Pro Glu Tyr Gly Arg Thr Asp Val Ala Glu Lys Phe
                    50                  55                  60

Gln Gly Arg Val Thr Ile Thr Ala Asp Thr Ser Thr Asp Thr Ala Tyr
            65                  70                  75                  80

Met Glu Leu Ser Ser Leu Arg Ser Glu Asp Thr Ala Val Tyr Tyr Cys
                            85                  90                  95

Ala Arg Thr Lys Tyr Asn Ser Gly Tyr Gly Phe Pro Tyr Trp Gly Gln
                            100                 105                 110

Gly Thr Thr Val Thr Val Ser Ser
                            115                 120

<210> SEQ ID NO 141
<211> LENGTH: 120
<212> TYPE: PRT
<213> ORGANISM: Artificial Sequence
<220> FEATURE:
<223> OTHER INFORMATION: Synthesized

<400> SEQUENCE: 141

Glu Val Gln Leu Val Gln Ser Gly Ala Glu Val Lys Lys Pro Gly Ala
            1               5                   10                  15

Thr Val Lys Ile Ser Cys Lys Val Ser Gly Tyr Thr Phe Thr Asp Ser
                            20                  25                  30

Val Met Asn Trp Val Gln Gln Gln Pro Gly Lys Gly Leu Glu Trp Met
                        35                  40                  45

Gly Trp Ile Asp Pro Glu Tyr Gly Arg Thr Asp Val Ala Glu Lys Phe
                    50                  55                  60
```

```
Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 142
<211> LENGTH: 120
<212> TYPE: PRT
<213> ORGANISM: Artificial Sequence
<220> FEATURE:
<223> OTHER INFORMATION: Synthesized

<400> SEQUENCE: 142

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Ser Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 143
<211> LENGTH: 120
<212> TYPE: PRT
<213> ORGANISM: Artificial Sequence
<220> FEATURE:
<223> OTHER INFORMATION: Synthesized

<400> SEQUENCE: 143

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Val Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120
```

<210> SEQ ID NO 144
<211> LENGTH: 120
<212> TYPE: PRT
<213> ORGANISM: Artificial Sequence
<220> FEATURE:
<223> OTHER INFORMATION: Synthesized

<400> SEQUENCE: 144

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Glu Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 145
<211> LENGTH: 120
<212> TYPE: PRT
<213> ORGANISM: Artificial Sequence
<220> FEATURE:
<223> OTHER INFORMATION: Synthesized

<400> SEQUENCE: 145

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Pro Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 146
<211> LENGTH: 120
<212> TYPE: PRT
<213> ORGANISM: Artificial Sequence
<220> FEATURE:
<223> OTHER INFORMATION: Synthesized

<400> SEQUENCE: 146

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Gln Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 147
<211> LENGTH: 120
<212> TYPE: PRT
<213> ORGANISM: Artificial Sequence
<220> FEATURE:
<223> OTHER INFORMATION: Synthesized

<400> SEQUENCE: 147

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Ser Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 148
<211> LENGTH: 120
<212> TYPE: PRT
<213> ORGANISM: Artificial Sequence
<220> FEATURE:
<223> OTHER INFORMATION: Synthesized

<400> SEQUENCE: 148

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Asp Thr Ala Tyr
65                  70                  75                  80

Met Glu Leu Ser Ser Leu Arg Ser Glu Asp Thr Ala Val Tyr Tyr Cys
                85                  90                  95

Ala Glu Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 149
<211> LENGTH: 120
<212> TYPE: PRT
<213> ORGANISM: Artificial Sequence
<220> FEATURE:
<223> OTHER INFORMATION: Synthesized

<400> SEQUENCE: 149

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Asp Thr Ala Tyr
65                  70                  75                  80

Met Glu Leu Ser Ser Leu Arg Ser Glu Asp Thr Ala Val Tyr Tyr Cys
                85                  90                  95

Ala Gly Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 150
<211> LENGTH: 120
<212> TYPE: PRT
<213> ORGANISM: Artificial Sequence
<220> FEATURE:
<223> OTHER INFORMATION: Synthesized

<400> SEQUENCE: 150

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Asp Thr Ala Tyr
65                  70                  75                  80

Met Glu Leu Ser Ser Leu Arg Ser Glu Asp Thr Ala Val Tyr Tyr Cys
                85                  90                  95

Ala Pro Thr Lys Tyr Asn Ser Gly Tyr Gly Phe Pro Tyr Trp Gly Gln
            100                 105                 110

Gly Thr Thr Val Thr Val Ser Ser

<210> SEQ ID NO 151
<211> LENGTH: 120
<212> TYPE: PRT
<213> ORGANISM: Artificial Sequence
<220> FEATURE:
<223> OTHER INFORMATION: Synthesized

<400> SEQUENCE: 151

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Lys Tyr Asn Ser Gly Tyr Gly Phe Pro Tyr Trp Gly Gln
            100                 105                 110

Gly Thr Thr Val Thr Val Ser Ser
        115                 120
```

<210> SEQ ID NO 152
<211> LENGTH: 120
<212> TYPE: PRT
<213> ORGANISM: Artificial Sequence
<220> FEATURE:
<223> OTHER INFORMATION: Synthesized

<400> SEQUENCE: 152

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Asn Ser Gly Tyr Gly Phe Pro Tyr Trp Gly Gln
            100                 105                 110

Gly Thr Thr Val Thr Val Ser Ser
        115                 120
```

<210> SEQ ID NO 153
<211> LENGTH: 120
<212> TYPE: PRT
<213> ORGANISM: Artificial Sequence
<220> FEATURE:
<223> OTHER INFORMATION: Synthesized

<400> SEQUENCE: 153

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Asn Trp Val Gln Ala Pro Gly Lys Gly Leu Glu Trp Met
            35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Thr Tyr Asn Ser Gly Tyr Gly Phe Pro Tyr Trp Gly Gln
                100                 105                 110

Gly Thr Thr Val Thr Val Ser Ser
            115                 120
```

<210> SEQ ID NO 154
<211> LENGTH: 120
<212> TYPE: PRT
<213> ORGANISM: Artificial Sequence
<220> FEATURE:
<223> OTHER INFORMATION: Synthesized

<400> SEQUENCE: 154

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Asn Trp Val Gln Ala Pro Gly Lys Gly Leu Glu Trp Met
            35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Gln Ser Gly Tyr Gly Phe Pro Tyr Trp Gly Gln
                100                 105                 110

Gly Thr Thr Val Thr Val Ser Ser
            115                 120
```

<210> SEQ ID NO 155
<211> LENGTH: 120
<212> TYPE: PRT
<213> ORGANISM: Artificial Sequence
<220> FEATURE:
<223> OTHER INFORMATION: Synthesized

<400> SEQUENCE: 155

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
                20                  25                  30

Val Met Asn Trp Val Arg Gln Gly Pro Gly Lys Gly Leu Glu Trp Met
            35                  40                  45

Gly Trp Ile Asp Pro Glu Tyr Gly Arg Thr Asp Val Ala Gln Lys Phe
```

```
                50                  55                  60
Gln Gly Arg Val Thr Met Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Gly Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 156
<211> LENGTH: 120
<212> TYPE: PRT
<213> ORGANISM: Artificial Sequence
<220> FEATURE:
<223> OTHER INFORMATION: Synthesized

<400> SEQUENCE: 156

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Asp Ser
                 20                  25                  30

Val Met Asn Trp Val Arg Gln His Pro Gly Lys Gly Leu Glu Trp Met
             35                  40                  45

Gly Trp Ile Asp Pro Glu Tyr Gly Arg Thr Asp Val Ala Gln Lys Phe
         50                  55                  60

Gln Gly Arg Val Thr Met Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Gly Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 157
<211> LENGTH: 120
<212> TYPE: PRT
<213> ORGANISM: Artificial Sequence
<220> FEATURE:
<223> OTHER INFORMATION: Synthesized

<400> SEQUENCE: 157

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Asp Ser
                 20                  25                  30

Val Met Asn Trp Val Arg Gln Gly Pro Gly Lys Gly Leu Glu Trp Met
             35                  40                  45

Gly Trp Ile Asp Pro Glu Tyr Gly Arg Thr Asp Val Ala Gln Lys Phe
         50                  55                  60

Gln Gly Arg Val Thr Met Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Gly Tyr Gln Ser Gly Tyr Gly Phe Pro Tyr Trp Gly Gln
                100                 105                 110
```

Gly Thr Thr Val Thr Val Ser Ser
            115                 120

<210> SEQ ID NO 158
<211> LENGTH: 120
<212> TYPE: PRT
<213> ORGANISM: Artificial Sequence
<220> FEATURE:
<223> OTHER INFORMATION: Synthesized

<400> SEQUENCE: 158

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln His Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Gln Ser Gly Tyr Gly Phe Pro Tyr Trp Gly Gln
            100                 105                 110

Gly Thr Thr Val Thr Val Ser Ser
            115                 120

<210> SEQ ID NO 159
<211> LENGTH: 120
<212> TYPE: PRT
<213> ORGANISM: Artificial Sequence
<220> FEATURE:
<223> OTHER INFORMATION: Synthesized

<400> SEQUENCE: 159

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gly Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 160
<211> LENGTH: 120
<212> TYPE: PRT
<213> ORGANISM: Artificial Sequence
<220> FEATURE:
<223> OTHER INFORMATION: Synthesized

```
<400> SEQUENCE: 160

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln His Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 161
<211> LENGTH: 120
<212> TYPE: PRT
<213> ORGANISM: Artificial Sequence
<220> FEATURE:
<223> OTHER INFORMATION: Synthesized

<400> SEQUENCE: 161

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Gly Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Gln Ser Gly Tyr Gly Phe Pro Tyr Trp Gly Gln
                100                 105                 110

Gly Thr Thr Val Thr Val Ser Ser
            115                 120

<210> SEQ ID NO 162
<211> LENGTH: 120
<212> TYPE: PRT
<213> ORGANISM: Artificial Sequence
<220> FEATURE:
<223> OTHER INFORMATION: Synthesized

<400> SEQUENCE: 162

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln His Pro Gly Lys Gly Leu Glu Trp Met
        35                  40                  45
```

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Gln Ser Gly Tyr Gly Phe Pro Tyr Trp Gly Gln
            100                 105                 110

Gly Thr Thr Val Thr Val Ser Ser
            115                 120

<210> SEQ ID NO 163
<211> LENGTH: 108
<212> TYPE: PRT
<213> ORGANISM: Rattus norvegicus

<400> SEQUENCE: 163

Asp Ile Val Met Thr Gln Ser Pro Thr Ser Ile Ser Ile Ser Val Gly
1               5                   10                  15

Glu Arg Val Thr Met Asn Cys Lys Ala Ser Gln Asn Val Asp Ser Asp
            20                  25                  30

Val Asp Trp Tyr Gln Gln Lys Thr Gly Gln Ser Pro Lys Leu Leu Ile
        35                  40                  45

Tyr Lys Ala Ser Asn Arg Tyr Thr Gly Val Pro Asp Arg Phe Thr Gly
    50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Thr His Pro Arg
                85                  90                  95

Thr Phe Gly Gly Gly Thr Lys Leu Glu Leu Lys Arg
            100                 105

<210> SEQ ID NO 164
<211> LENGTH: 108
<212> TYPE: PRT
<213> ORGANISM: Artificial Sequence
<220> FEATURE:
<223> OTHER INFORMATION: Synthesized

<400> SEQUENCE: 164

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 165
<211> LENGTH: 108
<212> TYPE: PRT

<213> ORGANISM: Artificial Sequence
<220> FEATURE:
<223> OTHER INFORMATION: Synthesized

<400> SEQUENCE: 165

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 166
<211> LENGTH: 108
<212> TYPE: PRT
<213> ORGANISM: Artificial Sequence
<220> FEATURE:
<223> OTHER INFORMATION: Synthesized

<400> SEQUENCE: 166

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 167
<211> LENGTH: 108
<212> TYPE: PRT
<213> ORGANISM: Artificial Sequence
<220> FEATURE:
<223> OTHER INFORMATION: Synthesized

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 168
<211> LENGTH: 108
<212> TYPE: PRT
<213> ORGANISM: Artificial Sequence
<220> FEATURE:
<223> OTHER INFORMATION: Synthesized

<400> SEQUENCE: 168

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asn Val Asp Ser Asp
                20                  25                  30

Val Asp Trp Tyr Gln Gln Lys Pro Gly Gln Ala Pro Arg Leu Leu Ile
            35                  40                  45

Tyr Lys Ala Ser Asn Arg Tyr Thr Gly Ile Pro Ala Arg Phe Ser Gly
        50                  55                  60

Ser Gly Ser Gly Arg Asp Phe Thr Leu Thr Ile Ser Ser Leu Glu Pro
65                  70                  75                  80

Glu Asp Phe Ala Val Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 169
<211> LENGTH: 108
<212> TYPE: PRT
<213> ORGANISM: Artificial Sequence
<220> FEATURE:
<223> OTHER INFORMATION: Synthesized

<400> SEQUENCE: 169

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Asp Ser Asp
                20                  25                  30

Val Asp Trp Tyr Gln Gln Lys Pro Gly Gln Ala Pro Arg Leu Leu Ile
            35                  40                  45

Tyr Lys Ala Ser Asn Arg Tyr Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 170
<211> LENGTH: 108
<212> TYPE: PRT
<213> ORGANISM: Artificial Sequence
<220> FEATURE:
<223> OTHER INFORMATION: Synthesized

```
<400> SEQUENCE: 170

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asn Val Asp Ser Asp
            20                  25                  30

Val Asp Trp Tyr Gln Gln Lys Pro Asp Gln Ser Pro Lys Leu Leu Ile
        35                  40                  45

Lys Lys Ala Ser Asn Arg Tyr Thr Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 171
<211> LENGTH: 108
<212> TYPE: PRT
<213> ORGANISM: Artificial Sequence
<220> FEATURE:
<223> OTHER INFORMATION: Synthesized

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Glu Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 172
<211> LENGTH: 108
<212> TYPE: PRT
<213> ORGANISM: Artificial Sequence
<220> FEATURE:
<223> OTHER INFORMATION: Synthesized

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 173
<211> LENGTH: 108
<212> TYPE: PRT
<213> ORGANISM: Artificial Sequence
<220> FEATURE:
<223> OTHER INFORMATION: Synthesized

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Pro Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 174
<211> LENGTH: 108
<212> TYPE: PRT
<213> ORGANISM: Artificial Sequence
<220> FEATURE:
<223> OTHER INFORMATION: Synthesized

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 175
<211> LENGTH: 108
<212> TYPE: PRT
<213> ORGANISM: Artificial Sequence
<220> FEATURE:
<223> OTHER INFORMATION: Synthesized

<400> SEQUENCE: 175

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Asp
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105
```

<210> SEQ ID NO 176
<211> LENGTH: 108
<212> TYPE: PRT
<213> ORGANISM: Artificial Sequence
<220> FEATURE:
<223> OTHER INFORMATION: Synthesized

<400> SEQUENCE: 176

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Glu Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105
```

<210> SEQ ID NO 177
<211> LENGTH: 108
<212> TYPE: PRT
<213> ORGANISM: Artificial Sequence
<220> FEATURE:
<223> OTHER INFORMATION: Synthesized

<400> SEQUENCE: 177

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95
```

```
Thr Phe Gly Gly Gly Thr Lys Val Glu Ile Lys Arg
            100                 105
```

<210> SEQ ID NO 178
<211> LENGTH: 108
<212> TYPE: PRT
<213> ORGANISM: Artificial Sequence
<220> FEATURE:
<223> OTHER INFORMATION: Synthesized

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Glu Gln Ser Asn Thr His Pro Arg
                85                  90                  95

Thr Phe Gly Gly Gly Thr Lys Val Glu Ile Lys Arg
            100                 105
```

<210> SEQ ID NO 179
<211> LENGTH: 108
<212> TYPE: PRT
<213> ORGANISM: Artificial Sequence
<220> FEATURE:
<223> OTHER INFORMATION: Synthesized

<400> SEQUENCE: 179

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Ser Asn Thr His Pro Arg
                85                  90                  95

Thr Phe Gly Gly Gly Thr Lys Val Glu Ile Lys Arg
            100                 105
```

<210> SEQ ID NO 180
<211> LENGTH: 108
<212> TYPE: PRT
<213> ORGANISM: Artificial Sequence
<220> FEATURE:
<223> OTHER INFORMATION: Synthesized

<400> SEQUENCE: 180

```
Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Lys Gln Ser Asn Thr His Pro Arg
                85                  90                  95

Thr Phe Gly Gly Gly Thr Lys Val Glu Ile Lys Arg
            100                 105

<210> SEQ ID NO 181
<211> LENGTH: 108
<212> TYPE: PRT
<213> ORGANISM: Artificial Sequence
<220> FEATURE:
<223> OTHER INFORMATION: Synthesized

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Pro Gln Ser Asn Thr His Pro Arg
                85                  90                  95

Thr Phe Gly Gly Gly Thr Lys Val Glu Ile Lys Arg
            100                 105

<210> SEQ ID NO 182
<211> LENGTH: 108
<212> TYPE: PRT
<213> ORGANISM: Artificial Sequence
<220> FEATURE:
<223> OTHER INFORMATION: Synthesized

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asn Thr His Pro Arg
                85                  90                  95

Thr Phe Gly Gly Gly Thr Lys Val Glu Ile Lys Arg
            100                 105

<210> SEQ ID NO 183
<211> LENGTH: 108
<212> TYPE: PRT
<213> ORGANISM: Artificial Sequence
<220> FEATURE:
<223> OTHER INFORMATION: Synthesized

<400> SEQUENCE: 183

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ser Gln Ser Asn Thr His Pro Arg
                85                  90                  95

Thr Phe Gly Gly Gly Thr Lys Val Glu Ile Lys Arg
            100                 105
```

<210> SEQ ID NO 184
<211> LENGTH: 108
<212> TYPE: PRT
<213> ORGANISM: Artificial Sequence
<220> FEATURE:
<223> OTHER INFORMATION: Synthesized

<400> SEQUENCE: 184

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Val Gln Ser Asn Thr His Pro Arg
                85                  90                  95

Thr Phe Gly Gly Gly Thr Lys Val Glu Ile Lys Arg
            100                 105
```

<210> SEQ ID NO 185
<211> LENGTH: 108
<212> TYPE: PRT
<213> ORGANISM: Artificial Sequence
<220> FEATURE:
<223> OTHER INFORMATION: Synthesized

<400> SEQUENCE: 185

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30
```

```
Val Asp Trp Tyr Gln Gln Lys Pro Gly Lys Ala Pro Lys Leu Leu Ile
         35                  40                  45

Tyr Lys Ala Ser Asn Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Met Asp Ser Asn Thr His Pro Arg
                 85                  90                  95

Thr Phe Gly Gly Gly Thr Lys Val Glu Ile Lys Arg
            100                 105
```

<210> SEQ ID NO 186
<211> LENGTH: 108
<212> TYPE: PRT
<213> ORGANISM: Artificial Sequence
<220> FEATURE:
<223> OTHER INFORMATION: Synthesized

<400> SEQUENCE: 186

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Asp Ser Asp
             20                  25                  30

Val Asp Trp Tyr Gln Gln Lys Pro Gly Lys Ala Pro Lys Leu Leu Ile
         35                  40                  45

Tyr Lys Ala Ser Gln Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Met Gln Ser Asn Thr His Pro Arg
                 85                  90                  95

Thr Phe Gly Gly Gly Thr Lys Val Glu Ile Lys Arg
            100                 105
```

<210> SEQ ID NO 187
<211> LENGTH: 108
<212> TYPE: PRT
<213> ORGANISM: Artificial Sequence
<220> FEATURE:
<223> OTHER INFORMATION: Synthesized

<400> SEQUENCE: 187

```
Asp Ile Gln Met Thr Gln Ser Pro Ser Ser Leu Ser Ala Ser Val Gly
 1               5                  10                  15

Asp Arg Val Thr Ile Thr Cys Gly Ala Ser Gln Asn Val Asp Ser Asp
             20                  25                  30

Val Asp Trp Tyr Gln Gln Lys Pro Gly Lys Ala Pro Lys Leu Leu Ile
         35                  40                  45

Tyr Lys Ala Ser Asn Asp Tyr Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Ala Gln Ser Asn Thr His Pro Arg
                 85                  90                  95

Thr Phe Gly Gly Gly Thr Lys Val Glu Ile Lys Arg
            100                 105
```

<210> SEQ ID NO 188

```
<211> LENGTH: 108
<212> TYPE: PRT
<213> ORGANISM: Artificial Sequence
<220> FEATURE:
<223> OTHER INFORMATION: Synthesized

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105

<210> SEQ ID NO 189
<211> LENGTH: 108
<212> TYPE: PRT
<213> ORGANISM: Artificial Sequence
<220> FEATURE:
<223> OTHER INFORMATION: Synthesized

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105

<210> SEQ ID NO 190
<211> LENGTH: 108
<212> TYPE: PRT
<213> ORGANISM: Artificial Sequence
<220> FEATURE:
<223> OTHER INFORMATION: Synthesized

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45
```

Tyr Lys Ala Ser Gln Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105

<210> SEQ ID NO 191
<211> LENGTH: 108
<212> TYPE: PRT
<213> ORGANISM: Artificial Sequence
<220> FEATURE:
<223> OTHER INFORMATION: Synthesized

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asn Val Asp Ser Asp
                20                  25                  30

Val Asp Trp Tyr Gln Gln Lys Pro Gly Lys Ala Pro Lys Leu Leu Ile
            35                  40                  45

Tyr Lys Ala Ser Gln Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105

<210> SEQ ID NO 192
<211> LENGTH: 108
<212> TYPE: PRT
<213> ORGANISM: Artificial Sequence
<220> FEATURE:
<223> OTHER INFORMATION: Synthesized

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
                20                  25                  30

Val Asp Trp Tyr Gln Gln Lys Pro Gly Lys Ala Pro Lys Leu Leu Ile
            35                  40                  45

Tyr Lys Ala Ser Gln Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105

<210> SEQ ID NO 193
<211> LENGTH: 108
<212> TYPE: PRT
<213> ORGANISM: Artificial Sequence

```
<220> FEATURE:
<223> OTHER INFORMATION: Synthesized

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Gln Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105

<210> SEQ ID NO 194
<211> LENGTH: 121
<212> TYPE: PRT
<213> ORGANISM: Homo sapiens

<400> SEQUENCE: 194

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 195
<211> LENGTH: 327
<212> TYPE: PRT
<213> ORGANISM: Homo sapiens

<400> SEQUENCE: 195

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
```

```
                65                  70                  75                  80
Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 196
<211> LENGTH: 330
<212> TYPE: PRT
<213> ORGANISM: Homo sapiens

<400> SEQUENCE: 196

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 197
<211> LENGTH: 106
<212> TYPE: PRT
<213> ORGANISM: Homo sapiens

<400> SEQUENCE: 197

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 198
<211> LENGTH: 105
<212> TYPE: PRT
<213> ORGANISM: Homo sapiens

<400> SEQUENCE: 198
```

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
50                      55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 199
<211> LENGTH: 492
<212> TYPE: PRT
<213> ORGANISM: Homo sapiens

<400> SEQUENCE: 199

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
            325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
            355                 360                 365

Glu Phe Gly Asn Gln Phe Gln Lys Ala Glu Thr Ile Pro Val Leu His
            370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
            405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
            435                 440                 445

Tyr Phe Gln Arg Ile Thr Leu Tyr Leu Lys Glu Lys Lys Tyr Ser Pro
            450                 455                 460

Cys Ala Trp Glu Val Val Arg Asp Glu Ile Met Arg Ser Phe Ser Leu
465                 470                 475                 480

Ser Thr Asn Leu Gln Glu Ser Leu Arg Ser Lys Glu
            485                 490

<210> SEQ ID NO 200
<211> LENGTH: 495
<212> TYPE: PRT
<213> ORGANISM: Homo sapiens

<400> SEQUENCE: 200

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp

```
                145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Cys Asp Leu Pro Gln Thr
                325                 330                 335

His Ser Leu Gly Ser Arg Arg Thr Leu Met Leu Leu Ala Gln Met Arg
            340                 345                 350

Arg Ile Ser Leu Phe Ser Cys Leu Lys Asp Arg His Asp Phe Gly Phe
        355                 360                 365

Pro Gln Glu Glu Phe Gly Asn Gln Phe Gln Lys Ala Glu Thr Ile Pro
    370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
                405                 410                 415

Glu Leu Tyr Gln Gln Leu Asn Asp Leu Glu Ala Cys Val Ile Gln Gly
            420                 425                 430

Val Gly Val Thr Glu Thr Pro Leu Met Lys Glu Asp Ser Ile Leu Ala
        435                 440                 445

Val Arg Lys Tyr Phe Gln Arg Ile Thr Leu Tyr Leu Lys Glu Lys Lys
    450                 455                 460

Tyr Ser Pro Cys Ala Trp Glu Val Val Arg Asp Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 201
<211> LENGTH: 5
<212> TYPE: PRT
<213> ORGANISM: Artificial Sequence
<220> FEATURE:
<223> OTHER INFORMATION: Synthesized

<400> SEQUENCE: 201

Gly Gly Gly Gly Ser
1               5
```

```
<210> SEQ ID NO 202
<211> LENGTH: 10
<212> TYPE: PRT
<213> ORGANISM: Artificial Sequence
<220> FEATURE:
<223> OTHER INFORMATION: Synthesized

<400> SEQUENCE: 202

Gly Gly Gly Gly Ser Gly Gly Gly Gly Ser
1               5                   10

<210> SEQ ID NO 203
<211> LENGTH: 15
<212> TYPE: PRT
<213> ORGANISM: Artificial Sequence
<220> FEATURE:
<223> OTHER INFORMATION: Synthesized

<400> SEQUENCE: 203

Gly Gly Gly Gly Ser Gly Gly Gly Gly Ser Gly Gly Gly Gly Ser
1               5                   10                  15

<210> SEQ ID NO 204
<211> LENGTH: 20
<212> TYPE: PRT
<213> ORGANISM: Artificial Sequence
<220> FEATURE:
<223> OTHER INFORMATION: Synthesized

<400> SEQUENCE: 204

Gly Gly Gly Gly Ser Gly Gly Gly Gly Ser Gly Gly Gly Gly Ser Gly
1               5                   10                  15

Gly Gly Gly Ser
            20

<210> SEQ ID NO 205
<211> LENGTH: 25
<212> TYPE: PRT
<213> ORGANISM: Artificial Sequence
<220> FEATURE:
<223> OTHER INFORMATION: Synthesized

<400> SEQUENCE: 205

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 206
<211> LENGTH: 121
<212> TYPE: PRT
<213> ORGANISM: Artificial Sequence
<220> FEATURE:
<223> OTHER INFORMATION: Synthesized

<400> SEQUENCE: 206

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60
```

```
Leu Lys Ser Arg Val Thr Ile Ser Val Asp Thr Ser Lys Asn Gln Ile
 65                  70                  75                  80

Ser Leu Arg Leu Thr Ser Val Thr Ala Ala Asp Thr Ala Val Tyr Tyr
                 85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120
```

<210> SEQ ID NO 207
<211> LENGTH: 121
<212> TYPE: PRT
<213> ORGANISM: Artificial Sequence
<220> FEATURE:
<223> OTHER INFORMATION: Synthesized

<400> SEQUENCE: 207

```
Gln Leu Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Ser
             20                  25                  30

Ser Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Thr Asn Tyr Asn Pro Ser
     50                  55                  60

Leu Lys Ser Arg Val Thr Ile Ser Val Asp Thr Leu Lys Asn Gln Ile
 65                  70                  75                  80

Ser Leu Arg Leu Thr Ser Val Thr Ala Ala Asp Thr Ala Val Tyr Tyr
                 85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120
```

<210> SEQ ID NO 208
<211> LENGTH: 121
<212> TYPE: PRT
<213> ORGANISM: Artificial Sequence
<220> FEATURE:
<223> OTHER INFORMATION: Synthesized

<400> SEQUENCE: 208

```
Gln Leu Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Ser
             20                  25                  30

Ser Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Asn Tyr Asn Pro Ser
     50                  55                  60

Leu Lys Ser Arg Val Thr Ile Ser Val Asp Thr Leu Lys Asn Gln Ile
 65                  70                  75                  80

Ser Leu Arg Leu Ser Ser Val Thr Ala Ala Asp Thr Ala Val Tyr Tyr
                 85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120
```

<210> SEQ ID NO 209
<211> LENGTH: 121
<212> TYPE: PRT
<213> ORGANISM: Artificial Sequence
<220> FEATURE:
<223> OTHER INFORMATION: Synthesized

<400> SEQUENCE: 209

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120
```

<210> SEQ ID NO 210
<211> LENGTH: 121
<212> TYPE: PRT
<213> ORGANISM: Artificial Sequence
<220> FEATURE:
<223> OTHER INFORMATION: Synthesized

<400> SEQUENCE: 210

```
Gln Leu Gln Leu Gln Glu Ser Gly Pro Gly Leu Val Lys Pro Ser Glu
1               5                   10                  15

Thr Leu Ser Leu Thr Cys Lys Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120
```

<210> SEQ ID NO 211
<211> LENGTH: 165
<212> TYPE: PRT
<213> ORGANISM: Homo sapiens

<400> SEQUENCE: 211

```
Cys Asp Leu Pro Gln Thr His Ser Leu Gly Ser Arg Arg Thr Leu Met
1               5                   10                  15
```

-continued

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                      55                  60

Asn Leu Phe Ser Thr Met Asp Ser Ser Ala Ala Trp Asp Glu Thr Leu
65                      70                  75                  80

Leu Asp Lys Phe Tyr Thr Glu Leu Tyr Gln Gln Leu Asn Asp Leu Glu
                    85                  90                  95

Ala Cys Val Ile Gln Gly Val Gly Val Ala Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                         140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 212
<211> LENGTH: 165
<212> TYPE: PRT
<213> ORGANISM: Homo sapiens

<400> SEQUENCE: 212

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                      55                  60

Asn Leu Phe Ser Thr Met Asp Ser Ser Ala Ala Trp Asp Glu Thr Leu
65                      70                  75                  80

Leu Asp Lys Phe Tyr Thr Glu Leu Tyr Gln Gln Leu Asn Asp Leu Glu
                    85                  90                  95

Ala Cys Val Ile Gln Gly Val Gly Val Ala Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                         140

Asp Glu Ile Met Arg Ser Phe Ser Leu Ser Thr Asn Leu Gln Glu Ser
145                 150                 155                 160

Leu Arg Ser Lys Glu
                165

<210> SEQ ID NO 213
<211> LENGTH: 165
<212> TYPE: PRT
<213> ORGANISM: Homo sapiens

<400> SEQUENCE: 213

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Met Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Gly Glu Ile Met Arg Ser Phe Ser Leu Ser Thr Asn Leu Gln Glu Ser
145                 150                 155                 160

Leu Arg Ser Lys Glu
                165

<210> SEQ ID NO 214
<211> LENGTH: 165
<212> TYPE: PRT
<213> ORGANISM: Homo sapiens
<220> FEATURE:
<221> NAME/KEY: MISC_FEATURE
<222> LOCATION: (106)..(106)
<223> OTHER INFORMATION: Xaa = A, C, D, E, F, G, H, I, K, L, M, N, P, Q,
      R, S, V, W, or Y

<400> SEQUENCE: 214

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Xaa Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Gln Ser
145                 150                 155                 160

Leu Arg Ser Lys Glu
                165
```

<210> SEQ ID NO 215
<211> LENGTH: 164
<212> TYPE: PRT
<213> ORGANISM: Homo sapiens

<400> SEQUENCE: 215

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Glu Thr Pro Leu Met Lys Glu
            100                 105                 110

Asp Ser Ile Leu Ala Val Arg Lys Tyr Phe Gln Arg Ile Thr Leu Tyr
        115                 120                 125

Leu Lys Glu Lys Lys Tyr Ser Pro Cys Ala Trp Glu Val Val Arg Ala
    130                 135                 140

Glu Ile Met Arg Ser Phe Ser Leu Ser Thr Asn Leu Gln Gln Ser Leu
145                 150                 155                 160

Arg Ser Lys Glu

<210> SEQ ID NO 216
<211> LENGTH: 637
<212> TYPE: PRT
<213> ORGANISM: Homo sapiens

<400> SEQUENCE: 216

Lys Leu Arg Thr Ala Thr Met Asp Cys Thr Trp Arg Ile Leu Phe Leu
1               5                   10                  15

Val Ala Ala Ala Thr Gly Thr His Ala Glu Val Gln Leu Val Gln Ser
            20                  25                  30

Gly Ala Glu Val Lys Lys Pro Gly Ala Thr Val Lys Ile Ser Cys Lys
        35                  40                  45

Val Ser Gly Tyr Thr Phe Thr Asp Ser Val Met Asn Trp Val Gln Gln
    50                  55                  60

Ala Pro Gly Lys Gly Leu Glu Trp Met Gly Trp Ile Asp Pro Glu Tyr
65                  70                  75                  80

Gly Arg Thr Asp Val Ala Glu Lys Phe Gln Gly Arg Val Thr Ile Thr
                85                  90                  95

Ala Asp Thr Ser Thr Asp Thr Ala Tyr Met Glu Leu Ser Ser Leu Arg
            100                 105                 110

Ser Glu Asp Thr Ala Val Tyr Tyr Cys Ala Arg Thr Lys Tyr Asn Ser
        115                 120                 125

Gly Tyr Gly Phe Pro Tyr Trp Gly Gln Gly Thr Thr Val Thr Val Ser
    130                 135                 140

Ser Ala Ser Thr Lys Gly Pro Ser Val Phe Pro Leu Ala Pro Cys Ser
145                 150                 155                 160

```
Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Lys
            210                 215                 220

Thr Tyr Thr Cys Asn Val Asp His Lys Pro Ser Asn Thr Lys Val Asp
225                 230                 235                 240

Lys Arg Val Glu Ser Lys Tyr Gly Pro Pro Cys Pro Pro Cys Pro Ala
                245                 250                 255

Pro Glu Phe Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser Gln Glu Asp Pro Glu Val Gln Phe Asn Trp Tyr Val
            290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
            355                 360                 365

Arg Glu Pro Gln Val Tyr Thr Leu Pro Pro Ser Gln Glu Glu Met Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
            435                 440                 445

Ser Cys Ser Val Met His Glu Ala Leu His Asn His Tyr Thr Gln Lys
            450                 455                 460

Ser Leu Ser Leu Ser Leu Gly Lys Cys Asp Leu Pro Gln Thr His Ser
465                 470                 475                 480

Leu Gly Ser Arg Arg Thr Leu Met Leu Leu Ala Gln Met Arg Arg Ile
                485                 490                 495

Ser Leu Phe Ser Cys Leu Lys Asp Arg His Asp Phe Gly Phe Pro Gln
            500                 505                 510

Glu Glu Phe Gly Asn Gln Phe Gln Lys Ala Glu Thr Ile Pro Val Leu
            515                 520                 525

His Glu Met Ile Gln Gln Ile Phe Asn Leu Phe Ser Thr Lys Asp Ser
            530                 535                 540

Ser Ala Ala Trp Asp Glu Thr Leu Leu Asp Lys Phe Tyr Thr Glu Leu
545                 550                 555                 560

Tyr Gln Gln Leu Asn Asp Leu Glu Ala Cys Val Ile Gln Gly Val Gly
                565                 570                 575

Val Ala Glu Thr Pro Leu Met Lys Glu Asp Ser Ile Leu Ala Val Arg
```

```
<210> SEQ ID NO 217
<211> LENGTH: 214
<212> TYPE: PRT
<213> ORGANISM: Homo sapiens

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```